(12) United States Patent
Gabriele et al.

(10) Patent No.: US 8,470,779 B2
(45) Date of Patent: Jun. 25, 2013

(54) CATECHOLAMINE REGULATED PROTEIN

(75) Inventors: Joseph Gabriele, Stoney Creek (CA); Ram Mishra, Dundas (CA); Zdenek Pristupa, Caledon (CA)

(73) Assignee: CRP40 Inc., Ottawa, Ontario (CA)

( * ) Notice: Subject to any disclaimer, the term of this patent is extended or adjusted under 35 U.S.C. 154(b) by 0 days.

(21) Appl. No.: 13/042,343

(22) Filed: Mar. 7, 2011

(65) Prior Publication Data
US 2011/0257101 A1  Oct. 20, 2011

Related U.S. Application Data

(63) Continuation-in-part of application No. 12/158,359, filed as application No. PCT/CA2006/002089 on Dec. 21, 2006, now Pat. No. 7,902,336.

(60) Provisional application No. 60/752,018, filed on Dec. 21, 2005.

(51) Int. Cl.
*A01N 37/18* (2006.01)
*A61K 38/00* (2006.01)

(52) U.S. Cl.
USPC .................. 514/17.7; 514/18.1; 514/21.2

(58) Field of Classification Search
None
See application file for complete search history.

(56) References Cited

U.S. PATENT DOCUMENTS
5,627,039 A  5/1997  Pereira-Smith
7,078,375 B1  7/2006  Larsen

FOREIGN PATENT DOCUMENTS
WO  WO03087768 A2  * 10/2003

OTHER PUBLICATIONS

Gabriele, et al., "Cloning, characterization, and functional studies of a human 40-kDa catecholamine-regulated protein: implications in central nervous system disorders", Cell Stress and Chaperones, Mar. 12, 2009, vol. 14(6), pp. 555-567.

Wadhwa, et al., "Identification of a Novel Member of Mouse hsp70 Family, its association with cellular mortal phenotype", The Journal of Biological Chemistry, vol. 268, No. 9, Issue of Mar. 25, 1993, pp. 6615-6621.

Domanico et al., Cloning of the Gene Encoding Peptide-Binding Protein 74 Shows that it is a New Member of the Heat Shock Protein 70 Family, Molecular and Cellular Biology, Jun. 1993, vol. 13, No. 6, pp. 3598-3610.

Ben-Zvi, et al., "Review: Mechanisms of Disaggregation and Refolding of Stable Protein Aggregates by Molecular Chaperones", Journal of Structural Biology, vol. 135, No. 2, Jul. 25, 2001, pp. 84-93.

Crowe, et al., "Report of the Chromosome 5 Workshop of the Sixth World Congress on Psychiatric Genetics", American Journal of Medical Genetics (Neuropsychiatric Genetics) vol. 88, No. 3, May 10, 1999, pp. 229-232.

Gabriele et al., "Asymmetric Modulation of a Catecholamine-regulated Protein in the Rat Brain, Following Quinpirole Administration", Synapse, vol. 49, No. 4, Jun. 20, 2003, pp. 261-269.

Gabriele et al., "Modulation of a 40-kDa Catecholamine-regulated Protein Following D-amphetamine Treatment in Discrete Brain Regions", European Journal of Pharmacology, vol. 453, No. 1, Oct. 18, 2002, p. 13-19.

(Continued)

*Primary Examiner* — Olga N Chernyshev
(74) *Attorney, Agent, or Firm* — Borden Ladner Gervais LLP

(57) ABSTRACT

A novel mammalian catecholamine-regulated protein called CRP40 is identified. This protein, and nucleic acid encoding same, is useful in methods of diagnosing and treating hypodopaminergic neurological disease, such as Parkinson's disease, multisystem atrophy, lewy body dementia, schizophrenia, and bipolar disease.

4 Claims, 28 Drawing Sheets

OTHER PUBLICATIONS

Gabriele et al., "Decreased Expression of a 40-kDa Catecholamine-regulated Protein in the Ventral Striatum of Schizophrenic Brain Specimens From the Stanley Foundation Neuropathology Consortium", Schizophrenia Research, vol. 74, No. 1, Apr. 1, 2005, pp. 111-119.
Giffard et al., "Chaperones, Protein Aggregation, and Brain Protection From Hypoxic/ischemic Injury", The Journal of Experimental Biology 207, Aug. 6, 2004, pp. 3213-3220.
Goto et al., "Immunohistochemical Localization of a 40-kDa Catecholamine Regulated Protein in the Nigrostriatal Pathway", Brain Research, vol. 900, No. 2, May 11, 2001, pp. 314-319.
Grover, "Molecular Biology of Stress Responses", Cell Stress & Chaperones, vol. 7, No. 1, Jan. 2002, pp. 1-5.
Kaul et al., "Mortalin: Present and Prospective", Experimental Gerontology, vol. 37, No. 10-11, Oct.-Nov. 2002, pp. 1157-1164.
Knable, "Schizophrenia and Bipolar Disorder: Findings From Studies of the Stanley Foundation Brain Collection", Schizophrenia Research, vol. 39, No. 2, Jun. 3, 1999, pp. 149-152.
Knable et al., "Multivariate Analysis of Prefrontal Cortical Data from the Stanley Foundation Neuropathology Consortium", Brain Research Bulletin, vol. 55, No. 5, Jul. 15, 2001, pp. 651-659.
Lewis et al., "Genome Scan Meta-analysis of Schizophrenia and Bipolar Disorder Part II:Schizophrenia", American Journal Human Genetics 73, Jul. 2003, pp. 34-48.
Macario et al., "Sick Chaperones and Ageing: A Perspective", Ageing Research Reviews 1, Apr. 2002, pp. 295-311.
Modi et al., "Modulation of Brain Catecholamine Absorbing Proteins by Dopaminergic Agents", European Journal Pharmacology 299, Mar. 1996, pp. 213-220.
Modrek et al., "Alternative Splicing in the Human, Mouse, and Rat Genomes is Associated with an Increased Frequency of Exon Creation and/or Loss", Nature Genetics, vol. 34, No. 2, Jun. 2003, pp. 177-180.
Muchowski et al., "Modulation of Neurodegeneration by Molecular Chaperones", Nature Reviews, Neuroscience, vol. 6, Jan. 2005, pp. 11-22.
Nair et al., "Molecular Cloning, Localization and Characterization of a 40-kDa Catecholamine-regulated Protein", Journal Neurochemistry 76, Oct. 19, 2001, pp. 1142-1152.
Perlman et al., "Postmortem Investigations of the Pathophysiology of Schizophrenia: The Role of Susceptibility Genes", Journal Psychiatry Neuroscience, vol. 29, No. 4, Feb. 17, 2004, pp. 287-293.
Pira et al., "The Atypical Antipsychotic Quetiapine Increases Both Noradrenaline and Dopamine Release in the Rat Prefrontal Cortex", European Journal of Pharmacology 504, Sep. 21, 2004, pp. 61-64.
Ross et al., "Covalent Affinity Labeling of Brain Catecholamine-absorbing Proteins Using a High-specific-activity Substituted Tetrahydronaphthalene", Journal of Neurochemistry 65, Jun. 29, 1995, pp. 2783-2789.
Ross et al., "Identification of Novel Catecholamine Absorbing Proteins in the Central Nervous System", Journal of Molecular Neuroscience, vol. 4, Sep. 1993, pp. 141-148.
Seamans et al., "The principal features and mechanisms of dopamine modulation in the prefrontal cortex", Progress in Neurobiology 74, May 4, 2004, pp. 1-57.
Seeman et al., "Schizophrenia: more dopamine, more D2 receptors", Proc Natl Acad Sci, vol. 97, No. 14, Jul. 5, 2000, pp. 7673-7675.
Selemon et al., "Cellular pathology in the dorsolateral prefrontal cortex distinguishes schizophrenia from bipolar disorder". Current Molecular Medicine, vol. 3, No. 5, Aug. 2003, 427-436.
Sharan, et al., "Cocaine treatment increases expression of a 40 kDa catecholamine-regulated protein in discrete brain regions", Synapse, vol. 47, No. 1, Oct. 30, 2002, pp. 33-44.
Sharan et al., "Modulation of a 40-kDa catecholamine regulated protein by dopamine receptor antagonists", European Journal of Pharmacology, vol. 413, No. 1, Feb. 9, 2001, pp. 73-79.
Sherman et al., "Cellular defenses against unfolded proteins: a cell biologist thinks about neurodegenerative diseases", Neuron, vol. 29, Jan. 2001, pp. 15-32.
Sklar et al., "Genome-wide scan in Portuguese Island families identifies 5q31-5q35 as a susceptibility locus for schizophrenia and psychosis", Molecular Psychiatry, 9, Dec. 2003, 213-218.
Soti et al., "Chaperones and aging: role in neurodegeneration and in other civilizational diseases", Neurochemistry International, 41, Jan. 7, 2002, pp. 383-389.
Soti et al., "Chaperones come of age", Cell Stress & Chaperones, vol. 7, No. 2, Jan. 16, 2002, pp. 186-190.
Svensson, "Alpha-adrenoceptor modulation hypothesis of antipsychotic atypicality", Progress in Neuro-psychopharmacoly & Biological Psychiatry, 27, Sep. 9, 2003, pp. 1145-1158.
Wadhwa et al., "Protein markers for cellular mortality and immortality", Mutatation Research, 256, Jul. 1, 1991, pp. 243-254.
Wadhwa et al., "An Hsp70 family chaperone, mortalin/mthsp70/PBP74/Grp75: what, when, and where?", Cell Stress & Chaperones, vol. 7, No. 3, Apr. 16, 2002, pp. 309-316.
Weinberger, "Schizophrenia and the frontal lobe", Trends Neuroscience, vol. 11, No. 8, Aug. 1988, 367-370.
Weinberger et al., "Prefrontal neurons and the genetics of schizophrenia", Biol Psychiatry, 50, Jul. 20, 2001, pp. 825-844.
Xie et al. "Human mortalin (HSPA9): a candidate for the myeloid leukemia tumor suppressor gene on 5q31", Leukemia, 14, Aug. 1, 2000, pp. 2128-2134.
Graveley, "Alternative Splicing: Increasing Diversity in the Proteomic World", Trends in Genetics, vol. 17, No. 2, Feb. 2001, pp. 100-107.
Hong et al., "Genetic Mapping Using Haplotype and Model-Free Linkage Analysis Supports Previous Evidence for a Locus Predisposing to Severe Bipolar Disorder at 5q31-33", American Journal of Medical Genetics Part B (Neuropsychiatric Genetics) 125B, Feb. 2004, pp. 83-86.
Kaul et al., "Overexpressed Mortalin (mot-2)/mthsp70/GRP75 and hTERT Cooperate to Extend the in vitro Lifespan of Human Fibroblasts", Experimental Cell Research, vol. 286, No. 1, May 15, 2003, pp. 96-101.
Matsumoto et al., "Catechol O-methyltransferase (COMT) mRNA Expression in the Dorsolateral Prefontal Cortex of Patients with Schizophrenia", Neuropsychopharmacology 28, Apr. 23, 2003, pp. 1521-1530.
Ohtsuka et al., "Roles of Molecular Chaperones in the Nervous System", Brain Research Bulletin, vol. 53, No. 2, Jun. 15, 2000, pp. 141-146.
Benes, "Emerging Principles of Altered Neural Circuitry in Schizophrenia", Brain Research Reviews, vol. 31, No. 2-3, Mar. 13, 2000, pp. 251-269.
Bradford, "A Rapid and Sensitive Method for the Quantitation of Microgram Quantities of Protein Utilizing the Principle of Protein-Dye Binding", Analytical Biochemistry, vol. 72, Jan. 29, 1976, pp. 248-254.
Gabriele et al., "Knockdown of Mortalin Within the Medial Prefrontal Cortex Impairs Normal Sensorimotor Gating", Synapse, New York, Nov. 2010, vol. 64, No. 11, pp. 808-813.
Gabriele et al., "Antipsychotic drug use is correlated with CRP40/mortalin mRNA expression in the dorsolateral prefrontal cortex of human postmortem brain specimens", Schizophrenia Research, Jun., 2010, vol. 119, No. 1-3, pp. 228-231.
European Patent Application No. 06840516.6, European Examination Report dated Mar. 27, 2013.

* cited by examiner

Human CRP 40 amino acid sequence

MDSSGPKHLNMKLTR
AQFEGIVTDLIRRTI
APCQKAMQDAEVSKS
DIGEVILVGGMTRMP
KVQQTVQDLFGRAPS
KAVNPDEAVAIGAAI
QGGVLAGDVTDVLLL
DVTPLSLGIETLGGV
FTKLINRNTTIPTKK
SQVFSTAADGQTQVE
IKVCQGEREMAGDNK
LLGQFTLIGIPPAPR
GVPQIEVTFDIDANG
IVHVSAKDKGTGREQ
QIVIQSSGGLSKDDI
ENMVKNAEKYAEEDR
RKKERVEAVNMAEGI
IHDTETKMEEFKDQL
PADECNKLKEEISKM
RELLARKDSETGENI
RQAASSLQQASLKLF
EMAYKKMASEREGSG
SSGTGEQKEDQKEEK
Q

FIGURE 13A

Human CRP 40 nucleotide sequence

```
   1 atg gat tct tct gga ccc aag cat ttg aat atg aag ttg acc cgt
  46 gct caa ttt gaa ggg att gtc act gat cta atc aga agg act atc
  91 gct cca tgc caa aaa gct atg caa gat gca gaa gtc agc aag agt
 136 gac ata gga gaa gtg att ctt gtg ggt ggc atg act agg atg ccc
 181 aag gtt cag cag act gta cag gat ctt ttt ggc aga ccc cca agt
 226 aaa gct gtc aat cct gat gag gct gtg gcc att gga gct gcc att
 271 cag gga ggt gtg ttg gcc ggc gat gtc acg gat gtg ctg ctc ctt
 316 gat gtc act ccc ctg tct ctg ggt att gaa act cta gga ggt gtc
 361 ttt acc aaa ctt att aat agg aat acc act att cca acc aag aag
 406 agc cag cta ttc tct act gcc gct gat ggt caa acg caa gtg gaa
 451 att aaa gtg tgt cag ggt gaa aga gag atg gct gga gac aac aaa
 496 ctc ctt gga cag ttt act ttg att gga att cca cca gcc cct cgt
 541 gga gtt cct cag att gaa gtt aca ttt gac att gat gcc aat ggg
 586 ata gta cat gtt tct gct aaa gat aaa ggc aca gga cgt gag cag
 631 cag att gta atc cag tct tct ggt gga tta agc aaa gat gat att
 676 gaa aat atg gtt aaa aat gca gag aaa tat gct gaa gaa gac cgg
 721 cga aag aag gaa cga gtt gaa gca gtt aat atg gct gaa gga atc
 766 att cac gac aca gaa acc aag atg gaa gaa ttc aag gac caa tta
 811 cct gct gat gag tgc aac aag ctg aaa gaa gag att tcc aaa atg
 856 agg gag ctc ctg gct aga aaa gac agc gaa aca gga gaa aat att
 901 aga cag gca gca tcc tct ctt cag cag gca tca ctg aag ctg ttc
 946 gaa atg gca tac aaa aag atg gca tct gag cga gaa ggc tct gga
 991 agt tct ggc act ggg gaa caa aag gaa gat caa aag gag gaa aaa
1036 cag
```

FIGURE 13B

SEQUENCE LISTING

```
<160> NUMBER OF SEQ ID NOS: 8

<210> SEQ ID NO 1
<211> LENGTH: 33
<212> TYPE: DNA
<213> ORGANISM: Artificial Sequence
<220> FEATURE:
<223> OTHER INFORMATION: primer

<400> SEQUENCE: 1
tagggatcca tgattcttc tggacccaag cat                                    33

<210> SEQ ID NO 2
<211> LENGTH: 36
<212> TYPE: DNA
<213> ORGANISM: Artificial Sequence
<220> FEATURE:
<223> OTHER INFORMATION: primer

<400> SEQUENCE: 2
ctagaattct catcgttcct tctttggccg gttttt                                36

<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
atggattctt ctggacccaa gcat                                             24

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
tcgttccttc tttggccggt ttttt                                            25
```

```
<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
ttggccggcg atgtcacgga tgtg                                              24

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
acacacttta atttccactt gcgt                                              24

<210> SEQ ID NO 7
<211> LENGTH: 1038
<212> TYPE: DNA
<213> ORGANISM: Homo sapiens

<400> SEQUENCE: 7
atggattctt ctggacccaa gcatttgaat atgaagttga cccgtgctca atttgaaggg       60
attgtcactg atctaatcag aaggactatc gctccatgcc aaaaagctat gcaagatgca      120
gaagtcagca agagtgacat aggagaagtg attcttgtgg gtggcatgac taggatgccc      180
aaggttcagc agactgtaca ggatcttttt ggcagagccc aagtaaagc tgtcaatcct       240 gatgaggctg tggccattgg agctgccatt cagggaggtg tgttggccgg cgatgtcacg      300
gatgtgctgc tccttgatgt cactcccctg tctctgggta ttgaaactct aggaggtgtc      360
tttaccaaac ttattaatag aataccact attccaacca agaagagcca ggtattctct       420
actgccgctg atggtcaaac gcaagtggaa attaaagtgt gtcagggtga agagagatg       480 gctggagaca caaaactcct tggacagttt actttgattg gaattccacc agcccctcgt      540
ggagttcctc agattgaagt tacatttgac attgatgcca atgggatagt acatgtttct      600
gctaaagata aaggcacagg acgtgagcag cagattgtaa tccagtcttc tggtggatta      660
agcaaagatg atattgaaaa tatggttaaa aatgcagaga atatgctga gaagaccgg       720 cgaaagaagg aacgagttga agcagttaat atggctgaag gaatcattca cgacacagaa      780
accaagatgg aagaattcaa ggaccaatta cctgctgatg agtgcaacaa gctgaaagaa      840
gagatttcca aaatgagggaa gctcctggct agaaaagaca gcgaaacagg agaaaatatt      900
agacaggcag catcctctct tcagcaggca tcactgaagc tgttcgaaat ggcatacaaa      960
aagatggcat ctgagcgaga aggctctgga agttctggca ctggggaaca aaggaagat     1020 caaaaggagg aaaaacag                                                    1038

<210> SEQ ID NO 8
<211> LENGTH: 346
<212> TYPE: PRT
<213> ORGANISM: Homo sapiens

<400> SEQUENCE: 8

Met Asp Ser Ser Gly Pro Lys His Leu Asn Met Lys Leu Thr Arg Ala
1               5                   10                  15
```

-continued

```
Gln Phe Glu Gly Ile Val Thr Asp Leu Ile Arg Arg Thr Ile Ala Pro
             20                  25                  30

Cys Gln Lys Ala Met Gln Asp Ala Glu Val Ser Lys Ser Asp Ile Gly
             35                  40                  45

Glu Val Ile Leu Val Gly Gly Met Thr Arg Met Pro Lys Val Gln Gln
 50                      55                  60

Thr Val Gln Asp Leu Phe Gly Arg Ala Pro Ser Lys Ala Val Asn Pro
 65                      70                  75                  80

Asp Glu Ala Val Ala Ile Gly Ala Ala Ile Gln Gly Gly Val Leu Ala
                 85                  90                  95

Gly Asp Val Thr Asp Val Leu Leu Leu Asp Val Thr Pro Leu Ser Leu
             100                 105                 110

Gly Ile Glu Thr Leu Gly Gly Val Phe Thr Lys Leu Ile Asn Arg Asn
             115                 120                 125

Thr Thr Ile Pro Thr Lys Lys Ser Gln Val Phe Ser Thr Ala Ala Asp
130                      135                 140

Gly Gln Thr Gln Val Glu Ile Lys Val Cys Gln Gly Glu Arg Glu Met
145                 150                 155                 160

Ala Gly Asp Asn Lys Leu Leu Gly Gln Phe Thr Leu Ile Gly Ile Pro
                 165                 170                 175

Pro Ala Pro Arg Gly Val Pro Gln Ile Glu Val Thr Phe Asp Ile Asp
             180                 185                 190

Ala Asn Gly Ile Val His Val Ser Ala Lys Asp Lys Gly Thr Gly Arg
             195                 200                 205

Glu Gln Gln Ile Val Ile Gln Ser Ser Gly Gly Leu Ser Lys Asp Asp
             210                 215                 220

Ile Glu Asn Met Val Lys Asn Ala Glu Lys Tyr Ala Glu Glu Asp Arg
225                 230                 235                 240

Arg Lys Lys Glu Arg Val Glu Ala Val Asn Met Ala Glu Gly Ile Ile
                 245                 250                 255

His Asp Thr Glu Thr Lys Met Glu Glu Phe Lys Asp Gln Leu Pro Ala
             260                 265                 270

Asp Glu Cys Asn Lys Leu Lys Glu Glu Ile Ser Lys Met Arg Glu Leu
             275                 280                 285

Leu Ala Arg Lys Asp Ser Glu Thr Gly Glu Asn Ile Arg Gln Ala Ala
290                 295                 300

Ser Ser Leu Gln Gln Ala Ser Leu Lys Leu Phe Glu Met Ala Tyr Lys
305                 310                 315                 320

Lys Met Ala Ser Glu Arg Glu Gly Ser Gly Ser Ser Gly Thr Gly Glu
                 325                 330                 335

Gln Lys Glu Asp Gln Lys Glu Glu Lys Gln
             340                 345
```

CATECHOLAMINE REGULATED PROTEIN

CROSS-REFERENCE TO RELATED APPLICATIONS

This application is a continuation-in-part of U.S. patent application Ser. No. 12/158,359 filed Jun. 20, 2008, which is a national phase entry of PCT/CA2006/002089, filed Dec. 21, 2006, which claims full benefit of priority from U.S. provisional patent application Ser. No. 60/752,018, filed Dec. 21, 2005, both of which are herein incorporated by reference in their entirety.

TECHNICAL FIELD

The present disclosure relates to catecholamine-regulated proteins, which are useful as a biomarker and therapeutic for neurological disease, including neurodevelopmental and neurodegenerative diseases.

BACKGROUND

Molecular chaperone proteins also referred to as heat shock proteins, are ubiquitous highly conserved proteins that bind to unstable proteins and aid in their refolding to maintain proper and stable conformation (Macario and Conway 2002; Ohtsuka and Suzuki 2000; Sherman and Goldberg 2001; Soti and Csermely 2002b; Soti and Csermely 2002a). Furthermore, molecular chaperone proteins have additional functions such as: (1) shuttling proteins to the nucleus; (2) acting as a transcriptional factor in cell regulation; (3) and providing weak binding abilities to normal proteins within the cell in order to maintain elements of cellular networks (Sherman and Goldberg 2001; Soti and Csermely 2002b; Soti and Csermely 2002a). Environmental and oxidative stresses lead to the expression of molecular chaperone proteins, which bind to the hydrophobic surfaces of damaged and denatured proteins, allowing for their proper folding and prevention of precipitation and aggregation of these proteins, ultimately preventing cell death (Macario and Conway 2002).

As the organism ages, cells are prone to mutations, post-translational aberrations, increased oxidative and environmental stresses, resulting in greater aggregation of proteins (Giffard et al. 2004; Muchowski and Wacker 2005). Ageing of the organism may also lead to deficiencies in the anti-stress mechanism such as decreased molecular chaperone synthesis and inefficiencies in the ubiquitin-proteosome and lysosome-mediated autophagy degradation pathways (Muchowski and Wacker 2005). Recent reports have implicated deficiencies in molecular chaperone recruitment to the progression of many neurodegenerative and neurodevelopmental diseases such as: Parkinsons, Alzheimers and schizophrenia (Ohtsuka and Suzuki 2000; Sherman and Goldberg 2001; Soti and Csermely 2002a). This concept is especially important in post-mitotic cells such as neurons, which leads to massive accumulation of aggregated proteins (Soti and Csermely 2002a).

The presence of a unique class of brain-specific proteins, which bind to DA and structurally related catecholamines has recently been reported. These proteins have been termed catecholamine-regulated proteins (CRPs) (Ross et al. 1993; Ross et al. 1995). Three species of CRP (with molecular weights of 26, 40, and 47-kDa, respectively) have been isolated. Pharmacological and biochemical studies have shown no similarity between these particular proteins, known catecholamine binding proteins, or receptors present in the brain (Modi et al. 1996; Ross et al. 1993; Ross et al. 1995). However, these particular proteins have high homology with the heat shock protein family. For example, molecular cloning of bovine brain CRP40 (Genbank #AF047009) revealed that this protein is related to the heat shock protein 70 kDa (Hsp70) family. As discussed earlier, heat shock proteins act as molecular chaperones and protect the cell from oxidative and other types of stresses (Ben Zvi and Goloubinoff 2001; Grover 2002; Soti and Csermely 2002b; Soti and Csermely 2002a).

Mortalin is a mitochondrial heat shock protein that was discovered in 1991 as a 66 kDa protein in mouse embryonic fibroblasts (Wadhwa et al. 1991). In order to trace molecular mechanisms of cell immortalization, studies using mouse embryonic fibroblasts identified mortalin as a mortality marker. The protein was cloned and characterized as Mortalin-1 (mot-1) in the cytoplasm of murine fibroblast cells (Wadhwa et al. 1991). Transfected mot-1 cDNA in NIH3T3 cells was distributed in the cytoplasm and resulted in cell senescence. In contrast, the mot-2 cDNA isoform was encoded in the perinuclear region and resulted in the malignant transformation of NIH 3T3 cells ultimately inducing cell immortalization in normal human fibroblasts (Kaul et al. 2003). Interestingly, the mot-1 and mot-2 proteins differ from each other by only 2 amino acid residues and the 2 murine mortalin isoforms come from two separate genes (Xie et al. 2000).

The mot-2 protein has been described as a multifunctional protein due to its diverse functions (chaperone, anchoring protein and signal transduction). Recent reports have shown that the N-terminus of the mot-2 protein binds to the carboxyl end of the tumor suppressor gene p53 (Kaul et al. 2002; Wadhwa et al. 2002). This binding property inhibits the transactivation of p53 to the nucleus, resulting in cell immortalization. Mot-2 has been recognized as an important biological marker in cancer tumor research.

The human genome project has discovered approximately 32000 genes in the human species (Human Genome Sequencing Consortium, Nature, 2000). With the use of high-throughput techniques of sequencing the human genome and Established Sequence Tags (EST's), the complexity of the human genome has increased dramatically (Graveley 2001; Modrek and Lee 2003; Wadhwa et al. 2002). EST's are derived from fully processed mRNA, which occur following the introduction of the 5' capping, splicing, and polyadenylation of the 3' end (Modrek and Lee 2003; Wadhwa et al. 2002). Alternate splicing involves the exon skipping of particular exons within a gene, which results in the generation of multiple transcripts encoding different proteins, with possibly different functions in 70-88% of the studies reported (Graveley 2001; Wadhwa et al. 2002). Alternate splicing occurs in the human genome with a frequency between 35-59%, which results in at least one splice alternative for each gene reported (Modrek and Lee 2003; Wadhwa et al. 2002).

With the aid of information gathered from the human genome project, it would be desirable to identify biomarkers effective to diagnose disease, such as neurological disease, particularly since access to neuronal tissue to obtain this information is not generally available. Furthermore, it is desirable to identify new treatments for devastating neurological diseases.

SUMMARY

A novel catecholamine regulated protein, referred to herein as CRP40, has been identified and determined to be useful in the diagnosis and treatment of neurological disease, in particular, hypodopaminergic neurological disease.

Thus, in one aspect of the present disclosure, an isolated human CRP40 protein is provided or a functionally equivalent variant thereof.

In another aspect, there is provided an isolated nucleic acid molecule encoding a human CRP40 protein or a functionally equivalent variant thereof.

In another aspect, there is provided a method of treating a hypodopaminergic neurological disease in a patient in need thereof comprising administering to the patient a therapeutically effective amount of a human CRP40 protein comprising the amino acid sequence as defined in SEQ ID NO: 8, or a functionally equivalent variant thereof exhibiting at least about 90% sequence homology with the amino acid sequence of SEQ ID NO: 8, or a nucleic acid encoding said CRP40 protein or functionally equivalent variant.

In some embodiments, the protein or functionally equivalent variant thereof exhibits at least about 98% sequence homology with the amino acid sequence of SEQ ID NO: 8.

In some embodiments, the step of administering comprises administering to the patient a therapeutically effective amount of CRP40 protein comprising an amino acid sequence as set out in SEQ ID NO:8 or a functionally equivalent variant thereof.

In some embodiments, the step of administering comprises administering to the patient a therapeutically effective amount of CRP40 protein comprising an amino acid sequence as set out in SEQ ID NO:8.

In some embodiments, the step of administering comprises administering to the patient a therapeutically effective amount of a nucleic acid encoding a human CRP40 protein comprising the amino acid sequence as defined in SEQ ID NO: 8, or a functionally equivalent variant thereof exhibiting at least about 90% sequence homology with the amino acid sequence of SEQ ID NO: 8.

In some embodiments, the step of administering comprises administering to the patient a therapeutically effective amount of a nucleic acid encoding a human CRP40 protein comprising the amino acid sequence as defined in SEQ ID NO: 8.

In some embodiments, the step of administering comprises administering to the patient a therapeutically effective amount of a nucleic acid comprising the nucleic acid sequence as defined in SEQ ID NO: 7.

In some embodiments, the step of administering comprises administering the CRP40 protein or nucleic acid encoding same directly to a desired region of the brain of the patient.

In some embodiments, the step of administering comprises administering the CRP40 protein or nucleic acid encoding same directly to the central nervous system.

In some embodiments, the hypodopaminergic neurological disease is selected from Parkinson's disease, Lewy body dementia, multisystem atrophy, schizophrenia, and bipolar disorder.

In another aspect, there is provided a pharmaceutical composition comprising:

(a) an isolated human CRP40 protein comprising the amino acid sequence as defined in SEQ ID NO: 8, or a functionally equivalent variant thereof exhibiting at least about 90% sequence homology with the amino acid sequence of SEQ ID NO: 8, or a nucleic acid encoding said CRP40 protein or functionally equivalent variant thereof; and (b) a pharmaceutically effective carrier.

In another aspect, there is provided a plasmid encoding a human CRP40 protein comprising the amino acid sequence as defined in SEQ ID NO: 8, or functionally equivalent variant thereof exhibiting at least about 90% sequence homology with the amino acid sequence of SEQ ID NO: 8.

In another aspect of the disclosure, a method of diagnosing neurological disease is provided which includes the steps of:
(a) obtaining a biological sample from a patient; and
(b) determining the amount of at least one of CRP40 and mortalin-2 protein present in the sample, wherein a decrease of at least about 10% in the amount of the protein as compared to a control amount present in a non-diseased patient is indicative of a neurological disease.

In another aspect of the disclosure, a method of diagnosing neurological disease is provided which includes the steps of:
(a) obtaining a biological sample from a patient; and
(b) determining the amount of nucleic acid encoding at least one of CRP40 and mortalin-2 protein present in the sample, wherein a decrease of at least about 10% in the amount of CRP40 or mortalin-2 nucleic acid as compared to a control amount present in a non-diseased patient is indicative of disease.

An article of manufacture is provided in another aspect of the disclosure. The article of manufacture includes a composition and packaging containing the composition. The composition includes at least one of CRP40 and mortalin-2, or a functionally equivalent fragment thereof, in combination with a pharmaceutically acceptable carrier. The packaging is labeled to indicate that the composition is effective to treat neurological disease.

These and other aspects of the disclosure will become apparent by reference to the accompanying description and drawings in which:

BRIEF DESCRIPTION OF THE DRAWINGS

FIG. 13A illustrates the amino acid sequence of human CRP40 (SEQ ID No:8);

FIG. 13B illustrates the nucleic acid sequence of human CRP40 (SEQ ID No:7);

DETAILED DESCRIPTION

Figure 1:
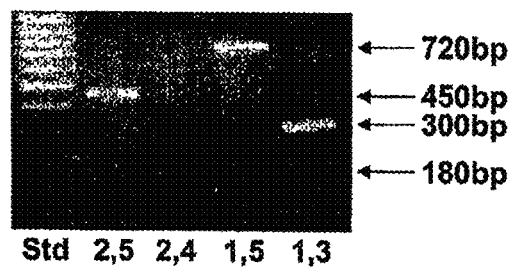
FIG. 1 illustrates the agarose gel electrophoresis results of a reverse transcriptase chain reaction performed with three combinations of forward and reverse primers generated from the BQ224193 EST.

A novel isolated catecholamine-regulated protein, referred to herein as human CRP40 or CRP40, is provided. CRP40 proteins, which include CRP40 and functionally equivalent variants thereof, are useful as both biomarkers in the diagnosis of neurological disease and as therapeutic agents in the treatment of such diseases.

The term "isolated" is used herein to refer to CRP40 proteins which are essentially pure and free from extraneous cellular material including other cellular proteins.

As used herein, the term "neurological disease" is meant to encompass neurodevelopmental disease (such as schizophrenia, bipolar disease and autism), as well as neurodegenerative disease (such as Parkinson's disease (PD) and Alzheimer's disease (AD), and other autoimmune diseases and genetic diseases such as multiple sclerosis, amyotrophic lateral sclerosis, Huntington disease, Creutzfeldt-Jakob, ADHD, Tourettes Syndrome, Rett Syndrome, minimal brain dysfunction in children and related neurological and psychiatric disorders). In particular, "nerological disease" is meant to encompass diseases characterized by dysregulated dopamine function and, more particularly, diseases characterized by hypo-dopamine function. Hypodopaminergic diseases include, for example, schizophrenia, bipolar disease, and Parkinson's disease, including Lewy body dementia (LB), and multisystem atrophy, which are generally considered to fall within the milieu of Parkinson's disease. While these diseases present with different symptoms, they are all linked by dysregulated dopamine function. For instance, Parkinson's and schizophrenia are known to involve the A9 and A10 pathways of the dopanigergic system, respectively, which interact and overlap. Thus, correction of function in these dopaminergic pathways can correct symptoms of these hypodopaminergic diseases.

CRP40 is a 346 amino acid catecholamine-regulated protein, the specific amino acid sequence of which is identified in FIG. 13A. The expression of CRP40 is inversely linked to neurological disease in mammals, such that a decrease of at least about 10% in the expression of CRP40 is indicative of neurological disease. Thus, CRP40 is useful as a biomarker for neurological disease, in particular, neurological disease associated with dysregulated dopamine function. In addition, given that this protein is decreased in these diseases, CRP40, functionally equivalent variants of CRP40, and nucleic acid encoding these, are useful in the treatment of such diseases.

Mortalin-2 or mot-2 was determined to be related to CRP40, with CRP40 being a novel spliced variant of mortalin-2. Mortalin-2 contains 679 amino acids. Mortalin-2 was also found to have utility as a biomarker of neurological disease, and to have therapeutic utility. Although the overlapping regions of mot-2 and CRP40 are at least 98% homologous, the diagnostic and therapeutic utilities of mot-2 were not previously known. Given this functional overlap, reference to "CRP40/mortalin-2" is made to refer to either CRP40 or mortalin-2.

Although utility has been demonstrated for mortalin-2, CRP40 is generally preferred over mortalin-2 as both a diagnostic agent and a therapeutic agent, since it is not ubiquitously expressed. CRP40 expression is limited and appears to be predominantly expressed in the CNS and certain blood components.

As will be appreciated by those of skill in the art, modified forms of CRP40 or mortalin-2, herein termed "functionally equivalent variants", may exist or may be prepared which retain CRP40 function and, thus, retain utility for use as a biomarker for neurological disease, and for the treatment of neurological disease. The variant need not exhibit identical activity, but exhibit sufficient activity to be useful as a biomarker and/or therapeutic agent.

Functionally equivalent variants may include, for example, variants having at least about 80%, 85%, 90%, 95%, 96%, 97%, 98% or 99% sequence identity to the sequence to which it is being compared. For example, a functionally equivalent variant of CRP40 may include variants having at least about 80%, 85%, 90%, 95%, 96%, 97%, 98% or 99% sequence identity to an amino acid sequence as defined in SEQ ID NO: 8. Also included is nucleic acid encoding said functionally equivalent variants.

Homology may be measured along the entire length of a molecule to which the sequence is being compared, or a portion of the molecule. For example, homology may be measured along a stretch of about 50, 100, 150, 200, 250, 300 or 350 amino acids, e.g. beginning from the C-terminus or N-terminus. For a nucleic acid, homology may be measured along a stretch of about 100, 150, 200, 300, 400, 500, 600 or more nucleotides.

Such modifications may, for example, result naturally from alternative splicing during transcription or from genetic coding differences. Such variants can readily be identified using established cloning techniques, as described in more detail in the specific examples that follow, employing primers derived from CRP40/mortalin-2. Additionally, such modifications may result from non-naturally occurring synthetic alterations made to CRP40/mortalin-2 to render a functionally equivalent variant which may have more desirable characteristics for use as a therapeutic, for example, increased activity or stability. Non-naturally occurring variants of CRP40 include analogues, fragments and derivatives thereof.

A functionally equivalent analogue of CRP40/mortalin-2 in accordance with the present disclosure incorporates 1 or more amino acid substitutions, additions or deletions. Commonly, amino acid additions or deletions are terminal additions or deletions at either end of the peptide to yield a functionally equivalent peptide; however, analogues incorporating internal amino acid insertion or deletion are within the scope of the present disclosure. Amino acid substitutions within CRP40/mortalin-2, particularly conservative amino acid substitutions, may also generate functionally equivalent analogues thereof. Examples of conservative substitutions include the substitution of one non-polar (hydrophobic) residue such as alanine, isoleucine, valine, leucine or methionine for another; the substitution of one polar (hydrophilic) residue for another such as between arginine and lysine, between glutamine and asparagine, between glutamine and glutamic acid, between asparagine and aspartic acid, and between glycine and serine; the substitution of one basic residue such as lysine, arginine or histidine for another; or the substitution of one acidic residue, such as aspartic acid or glutamic acid for another.

A functionally equivalent fragment in accordance with the present disclosure comprises a portion of the CRP40/mortalin-2 sequence. The fragment may comprise an interior portion of the CRP40/mortalin-2 sequence, or may comprise a terminal portion thereof.

A functionally equivalent CRP40 derivative in accordance with the present disclosure is CRP40/mortalin-2, or an analogue or fragment thereof, in which one or more of the amino acid residues therein is chemically derivatized. The amino acids may be derivatized at the amino or carboxy groups, or alternatively, at the side "R" groups thereof. Derivatization of amino acids within the peptide may render a peptide having more desirable characteristics such as increased stability or activity. Such derivatized molecules include for example, those molecules in which free amino groups have been derivatized to form, for example, amine hydrochlorides, p-toluene sulfonyl groups, carbobenzoxy groups, t-butyloxycarbonyl groups, chloroacetyl groups or formyl groups. Free carboxyl groups may be derivatized to form, for example, salts, methyl and ethyl esters or other types of esters or hydrazides. Free hydroxyl groups may be derivatized to form, for example, O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids, for example: 4-hydroxyproline may be substituted for proline; 5-hydroxylysine may be substituted for lysine; 3-methylhistidine may be substituted for histidine; homoserine may be substituted for serine; and ornithine may be substituted for lysine. Terminal modification of a peptide to protect against chemical or enzymatic degradation may also include acetylation at the N-terminus and amidation at the C-terminus of the peptide.

In the diagnostic aspects of the disclosure, a biological sample is obtained that is suitable to quantify either the level of CRP40/mortalin-2 protein (CRP40, mortalin-2 or a naturally occurring variant thereof) or the level of CRP40- or mortalin-2-encoding nucleic acid therein. Suitable biological samples for this purpose include blood (e.g. platelets and lymphocytes), saliva, urine, semen, hair, skin and cerebrospinal fluid. Where CRP40 is being measured, a preferred biological sample is blood, either whole blood or a blood component such as platelets or lymphocytes, etc. The sample is obtained from the mammal using methods conventional for the sample type. Many of these samples can readily be obtained in a non-invasive manner. Cerebrospinal fluid is obtained using the spinal tap procedure. The amount of biological sample required must be sufficient to allow quantitation of CRP40 protein or CRP40-encoding nucleic acid therein. For example, an amount of about 5 µg protein is generally needed for CRP40/mortalin-2 quantitation, while about 10 ng nucleic acid is generally needed for CRP40/mortalin-2 nucleic acid quantification.

In order to quantify CRP40/mortalin-2 protein content in a biological sample, the protein fraction is first isolated therefrom using standard isolation and fractionation techniques including lysis/centrifugation, precipitation and separation using, for example, electrophoresis and chromatography such as HPLC and affinity. Quantification of CRP40/mortalin-2 is then conducted in a number of ways as will be appreciated by one of skill in the art. CRP40/mortalin-2 can be isolated using a separation method and then quantified against standards. Immunological techniques, for example, can also be employed to identify and quantify CRP40/mortalin-2 either on its own or in conjunction with a separation technique. A CRP40/mortalin-2 primary antibody can be used in an affinity column to separate CRP40/mortalin-2 from a sample and a detectably labeled secondary antibody can be used for identification purposes. Also, detectably labeled (e.g. fluorescent, colorimetric, radioactive) CRP40/mortalin-2 antibody, or a related compound, can be linked to CRP40/mortalin-2 exposed in the sample or separated from a sample and quantified. Methods of making antibodies for use in the diagnostic methods are detailed below.

In another embodiment, CRP40/mortalin-2 in a sample can be quantified by measuring the amount of CRP40/mortalin-2 nucleic acid within the sample. For example, mRNA copy number can be measured by known techniques as described in detail in the examples that follow. Briefly, mRNA copy number can be determined using PCR, and specifically, the one-step real-time PCR protocol in which human CRP40/mortalin-2 forward and reverse primers were used in the protocol to amplify CRP40/mortalin-2 mRNA for quantity determination against pure CRP40/mortalin-2 mRNA standards.

Having determined the amount of CRP40/mortalin-2 in a biological sample obtained from a mammal, a comparison with a control value, determined to exist in a normal, undiseased state, is made. It has been determined that a decrease of at least about 10% in the amount of either of CRP40 or mortalin-2 protein or nucleic acid from normal is indicative of neurological disease. In some embodiments the measured decrease is at least about 15%, 20%, 25%, 30%, 40%, 50%, 60%, 70%, 80%, 90%, or 95% compared to normal controls.

In some embodiments, the biological sample is blood or a blood-derived sample. For instance, the biological sample may be a blood-derived sample comprising white blood cells, such as platelets and/or lymphocytes. In some embodiments, the biological sample is platelets. Platelets are developmentally related to the brain and therefore may be utilized as model to investigate neurological disorders.

In some embodiments, a decrease in either of CRP40 or mortalin-2 protein, or nucleic acid encoding same, compared to a normal control sample is indicative of schizophrenia, bipolar disorder, Parkinson's disease, Lewy body dementia, or multisystem atrophy.

In some embodiments, one or more additional indicators of the neurological disease may also be assessed, for example, a biological marker, or a behavioural, cognitive or neurological indicator. These will be well known to those skilled in the art and are dependent on the neurological disease being diagnosed.

For use as a therapeutic, CRP40/mortalin-2 in accordance with the present disclosure may be made using standard, well-established solid-phase peptide synthesis methods (SPPS). Two methods of solid phase peptide synthesis include the BOC and FMOC methods.

CRP40/mortalin-2 may also be made using any one of a number of suitable techniques based on recombinant technology. It will be appreciated that such techniques are well-established by those skilled in the art, and involve the expression of the CRP40/mortalin-2 encoding nucleic acid in a genetically engineered host cell.

Isolated nucleic acid encoding CRP40/mortalin-2, and variants thereof in accordance with the present disclosure, is also encompassed by the disclosure. Thus, nucleic acid, including DNA and RNA, encoding CRP40 having the amino acid sequence set out in FIG. 13A is provided. It will be appreciated that more than one nucleic acid sequence will encode CRP40 and its variants given the degeneracy that exists in the genetic code. A CRP40 coding sequence is provided in FIG. 13B. The amino acid sequence of mortalin-2 is as set out in the Gen Bank under deposit ABF 50973, while the nucleotide gene sequence is as set out in deposit NM 004134 and the complete cDNA sequence is set out in deposit DQ 531046.

DNA encoding a CRP40/mortalin-2 protein may be synthesized de novo by automated techniques well-known in the art. Generally, gene synthesis may be conducted by the successive 3' to 5' coupling of appropriately protected nucleotide reagents in an automated synthesizer, followed by recovery of the deprotected polynucleotide. Alternatively, the block ligation methodology may be employed whereby oligonucleotide "blocks", including up to about 80 nucleotides, are ligated by overhang complementarity as described in Wosnick et al. in Gene, 1989, 76:153. Sequences obtained by de novo synthesis may be amplified using the polymerase chain reaction as described in U.S. Pat. No. 4,683,195.

Upon obtaining CRP40 or mortalin-2-encoding DNA, recombinant techniques for producing CRP40/mortalin-2 therefrom generally involve insertion of the DNA sequence into a suitable expression vector which is subsequently introduced into an appropriate host cell (such as Chinese hamster ovary cells (CHO cells) for example of KI lineage (ATCC CCL 61), murine 3T3 cells (ATCC CRL 1658) or human embryonic kidney cells of the 293 lineage (ATCC CRL 1573)) for expression. Such transformed host cells are herein characterized as having the CRP40 DNA incorporated "expressibly" therein. Suitable expression vectors are those vectors which will drive expression of the inserted DNA in the selected host. Typically, expression vectors are prepared by site-directed insertion of a DNA construct therein. The DNA construct is prepared by replacing a coding region, or a portion thereof, within a gene native to the selected host, or in a gene originating from a virus infectious to the host, with CRP40/mortalin-2 DNA. In this way, regions required to control expression of the CRP40/mortalin-2 DNA, which are recognized by the host, including a region 5' of the PMCA CRP40 DNA to drive expression and a 3' region to terminate expression, are inherent in the DNA construct. To allow selection of host cells stably transformed with the expression vector, a selection marker is generally included in the vector which takes the form of a gene conferring some survival advantage on the transformants such as antibiotic resistance.

Cells stably transformed with a CRP40/mortalin-2 DNA-containing vector are grown in culture media and under growth conditions that facilitate the growth of the particular host cell used. One of skill in the art would be familiar with the media and other growth conditions required by the particular host cell chosen, as such information is well-documented in the art. Recombinant CRP40/mortalin-2 protein may be isolated from the host culture media by any one of a number of acceptable methods, such as the use of affinity columns or immunogenic methods using antibodies directed specifically to CRP40/mortalin-2, and then purified using techniques also well-known in the art such as gel electrophoresis. For therapeutic use, the oligopeptide compounds of the disclosure are desirably of "pharmaceutical grade" purity, a term used herein to denote an oligopeptide preparation which has been shown to migrate as a single peak on HPLC, to exhibit uniform and authentic amino acid composition and sequence upon analysis thereof, and which otherwise meets standards set by the various national bodies which regulate quality of pharmaceutical products.

Once prepared and suitably purified, CRP40, mortalin-2 and functional variants thereof in accordance with the disclosure, may be utilized to treat neurological disease. Generally, a pharmaceutical composition comprising the CRP40/mortalin-2 protein and at least one pharmaceutically acceptable adjuvant is used. The expression "pharmaceutically acceptable" means acceptable for use in the pharmaceutical and veterinary arts, i.e. not being unacceptably toxic or otherwise unsuitable. Examples of pharmaceutically acceptable adjuvants are those used conventionally with peptide-based drugs, such as diluents, excipients and the like. Reference may be made to "Remington's: The Science and Practice of Pharmacy", 21st Ed., Lippincott Williams & Wilkins, 2005, for guidance on drug formulations generally. The selection of adjuvant depends on the intended mode of administration of the composition. In one embodiment of the disclosure, the compounds are formulated for administration by infusion, or by injection either subcutaneously or intravenously, and are accordingly utilized as aqueous solutions in sterile and pyrogen-free form and optionally buffered or made isotonic. Thus, the compounds may be administered in distilled water or, more desirably, in saline, phosphate-buffered saline or 5% dextrose solution. Compositions for oral administration via tablet, capsule or suspension are prepared using adjuvants including sugars, such as lactose, glucose and sucrose; starches such as corn starch and potato starch; cellulose and derivatives thereof, including sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil and corn oil; polyols such as propylene glycol, glycerine, sorbital, mannitol and polyethylene glycol; agar; alginic acids; water; isotonic saline and phosphate buffer solutions. Wetting agents, lubricants such as sodium lauryl sulfate, stabilizers, tableting agents, anti-oxidants, preservatives, colouring agents and flavouring agents may also be present. Creams, lotions and ointments may be prepared for topical application using an appropriate base such as a triglyceride base. Such creams, lotions and ointments may also contain a surface active agent. Aerosol formulations, for example, for nasal delivery, may also be prepared in which suitable propellant adjuvants are used. Other adjuvants may also be added to the composition regardless of how it is to be administered, for example, anti-microbial agents may be added to the composition to prevent microbial growth over prolonged storage periods.

The active ingredients or compositions disclosed herein may be administered by any suitable route of administration, for example, topical, enteral, parenteral or cranial. Parenteral may, for example, include intravenous, intraarterial, intraosseous or intramuscular. Administration may be directly to the central nervous system, for example, epidural, intracerebral, or intracerebroventricular administration.

Preferred compositions and routes of administration are those that can deliver the active ingredient to a desired location in the brain of a patient to be treated. This may, in accordance with some routes of administration, involve crossing the blood brain barrier (BBB). Pharmacological means may be used for delivering biological molecules (e.g. proteins, peptides and nucleic acids) across the BBB, for example, by conjugating water soluble molecules to lipid carriers. Endogenous administration involving carrier mediated transport (CMT) or receptor mediated transport (RMT) of macromolecules to the desired target area in the brain may also be employed. As well, biological molecules may be directly administered into a desired region of the brain of a patient to be treated. Such delivery methods may, for example, include cerebral or ventricular infusion from implants, pumps or catheters, or the like. Invasive delivery methods such as these are typically reserved for debilitating diseases where quality of life is severely impaired or where life expectancy is decreased, such as Parkinson's disease, schizophrenia, bipolar disorder, Alzheimer's disease, ALS, and the like. For further discussion on drug delivery to the brain, see for example, Linninger et al., Drug Delivery into the Human Brain, 2005; Bobo et al., 1991; Pardridge, 1999; Pardridge, 2002; Kalyanasundaram et al., 1997; Morrison et al., 1994; Reisfeld et al, 1995; Sarntinoranont et al., 2003; Wang et al, 2003.

In some embodiments, a CRP40 protein or nucleic acid encoding same (including functionally equivalent variants) may be administered directly to a desired region of the brain of a patient to be treated.

In accordance with the disclosure, a therapeutically effective amount of a CRP40/mortalin-2 protein is administered to a mammal in the treatment of a neurological disease. As used herein, the term "mammal" is meant to encompass, without limitation, humans, domestic animals such as dogs, cats, horses, cattle, swine, sheep, goats and the like, as well as wild animals. A "patient" may be any mammal in need of treatment, but is most typically a human. The term "therapeutically effective amount" is an amount of the CRP40 or mortalin-2 protein, or nucleic acid encoding same (including functionally equivalent variants), indicated for treatment of the neurological disease while not exceeding an amount which may cause significant adverse effects. Treatment is intended to indicate that at least one symptom of the neurological disease is alleviated such that the patient can enjoy an improved quality of life compared to the absence of treatment. In this regard, treatment may also include prevention of undesirable symptoms. Dosages of the CRP40 or mortalin-2 protein will vary with many factors including the condition and individual being treated and may be determined by those of skill, for example, by starting at a lower than effective dose and titrating up to an effective dose. In some embodiments, appropriate dosages are in the range of about 1 µg-100 mg.

In another aspect of the present disclosure, an article of manufacture is provided. The article of manufacture comprises packaging material and a pharmaceutical composition. The composition comprises a pharmaceutically acceptable adjuvant and a therapeutically effective amount of a CRP40 or mortalin-2 protein, wherein the packaging material is labeled to indicate that the composition is useful to treat a neurological disease.

The packaging material may be any suitable material generally used to package pharmaceutical agents including, for example, glass, plastic, foil and cardboard.

Antibodies to CRP40 proteins are also provided in another aspect of the disclosure. The antibodies are useful in the diagnostic method of the disclosure as described above. Conventional methods can be used to prepare the antibodies including polyclonal antisera or monoclonal antibodies. To produce polyclonal antibodies, a mammal, (e.g. a mouse, hamster, or rabbit) can be immunized with an immunogenic form of the protein which elicits an antibody response in the mammal. Techniques for conferring immunogenicity on a peptide are well known in the art and include, for example, conjugation to carriers. The peptide can be administered in the presence of adjuvant. The progress of immunization can be monitored by detection of antibody titers in plasma or serum. Standard ELISA or other immunoassay procedures can be used with the immunogen as antigen to assess antibody levels. Following immunization, antisera can be obtained and, if desired, polyclonal antibodies isolated from the sera.

To produce monoclonal antibodies, antibody-producing cells (lymphocytes) are harvested from an immunized animal and fused with myeloma cells by standard somatic cell fusion procedures to form immortal hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al., Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with a selected CRP40 peptide and the monoclonal antibodies can be isolated.

The term "antibody" as used herein is intended to include fragments thereof which also specifically react with a CRP40 protein according to the disclosure. Antibodies can be fragmented using conventional techniques and the fragments screened for utility in the same manner as described above. For example, fragments can be generated by treating an antibody with pepsin. The resulting fragment can be further treated to reduce disulfide bridges.

Chimeric antibody derivatives, i.e., antibody molecules resulting from the combination of a variable non-human animal peptide region and a constant human peptide region are also contemplated within the scope of the disclosure. Chimeric antibody molecules can include, for example, the antigen binding domain from an antibody of a mouse, rat, or other species with a constant human peptide region. Conventional methods may be used to make chimeric antibodies containing the immunoglobulin variable region which recognizes a CRP40 protein of the disclosure (See, for example, Morrison et al., Proc. Natl. Acad. Sci. U.S.A. 81, 6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a CRP40 protein of the disclosure as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al, Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great. Britain).

CRP40 or mortalin-2-encoding nucleic acid molecules or oligonucleotide may also be used in a gene therapy method of treating a neurological disease. Administration of oligonucleotide that encodes CRP40/mortalin-2 to a patient suffering from such a disease will function to increase cellular CRP40/mortalin-2, thereby alleviating, at least in part, symptoms of the disease.

The term "oligonucleotide" refers to an oligomer or polymer of nucleotide or nucleoside monomers consisting of naturally occurring bases, sugars, and intersugar (backbone) linkages. The term also includes modified or substituted oligonucleotides comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the disclosure may be joined to form a chimeric oligonucleotide.

The therapeutic oligonucleotides of the present disclosure may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydrodyl guanine and other 8-substituted guanines, other aza and deaza uracils, thymidines, cytosines, adenines, or guanines, 5-trifluoromethyl uracil and 5-trifluoro cytosine.

Other therapeutic oligonucleotides of the disclosure may contain modified phosphorous, oxygen heteroatoms in the phosphate backbone, short chain alkyl or cycloalkyl inter-sugar linages or short chain heteroatomic or heterocyclic intersugar linkages. For example, the oligonucleotides may contain phosphorothioates, phosphotriesters, methyl phosphonates, and phosphorodithioates. For example, phosphorothioate bonds may link only the four to six 3'-terminal bases, may link all the nucleotides or may link only 1 pair of bases.

The therapeutic oligonucleotides of the disclosure may also comprise nucleotide analogs that may be better suited as therapeutic or experimental reagents. An example of an oligonucleotide analogue in accordance with the disclosure is a peptide nucleic acid (PNA) in which the deoxribose (or ribose) phosphate backbone in the DNA (or RNA), is replaced with a polymide backbone which is similar to that found in peptides (P. E. Nielson, et al Science 1991, 254, 1497). PNA analogues have been shown to be resistant to degradation by enzymes and to have extended lives in vivo and in vitro. PNAs also form stronger bonds with a complementary DNA sequence due to the lack of charge repulsion between the PNA strand and the DNA strand. Other oligonucleotide analogues may contain nucleotides containing polymer backbones, cyclic backbones, or acyclic backbones. For example, the nucleotides may have morpholino backbone structures (U.S. Pat. No. 5,034,506). Oligonucleotide analogues may also contain groups such as reporter groups, a group for improving the pharmacokinetic properties of an oligonucleotide, or a group for improving the pharmacodynamic properties of an antisense oligonucleotide. Antisense oligonucleotides may also incorporate sugar mimetics as will be appreciated by one of skill in the art.

Nucleic acid molecules may be constructed using chemical synthesis and enzymatic ligation reactions using procedures known in the art as previously described. The nucleic acid molecules of the disclosure may be chemically synthesized using naturally occurring nucleotides or variously modified nucleotides designed to increase the biological stability of the molecules or to increase the physical stability of the duplex formed with mRNA or the native gene, e.g. phosphorothioate derivatives and acridine substituted nucleotides. CRP40/mortalin-2 may be produced biologically using an expression vector introduced into cells in the form of a recombinant plasmid, phagemid or attenuated virus in which the CRP40/mortalin-2 sequences are produced under the control of a high efficiency regulatory region, the activity of which may be determined by the cell type into which the vector is introduced.

Once prepared, the oligonucleotides may be introduced into tissues or cells using techniques in the art including vectors (retroviral vectors, adenoviral vectors and DNA virus vectors) or physical techniques such as microinjection. The oligonucleotides may be directly administered in vivo or may be used to transfect cells in vitro which are then administered in vivo.

In some embodiments, whether for treatment, diagnosis, or research purposes, it may be desirable to downregulate the expression of CRP40/mortalin-2. As one of skill in the art will appreciate, CRP40/mortalin-2 expression can be inhibited at either the protein or nucleic acid levels. Synthetic inhibitors of CRP40 or mortalin-2 can be determined, for example, using assays designed to detect reduced CRP40 activity such as flow cytometry for platelet aggregation as described in detail in the specific examples.

CRP40 and mortalin-2 can also be inhibited at the nucleic acid level, for example, using anti-sense, snp or siRNA technologies. CRP40/mortalin-2-encoding nucleic acid molecules may be used to prepare antisense oligonucleotides against CRP40/mortalin-2 which may be therapeutically useful to inhibit CRP40 or mortalin-2. Accordingly, antisense oligonucleotides that are complementary to a nucleic acid sequence encoding CRP40/mortalin-2 according to the disclosure are also provided. The term "antisense oligonucleotide" as used herein means a nucleotide sequence that is complementary to a target CRP40 or mortalin-2 nucleic acid sequence.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleiotides may contain at least one region of modified nucleotides that confer beneficial properties (e.g. increased nuclease resistance, increased uptake into cells), or two or more oligonucleotides of the disclosure may be joined to form a chimeric oligonucleotide.

The antisense oligonucleotides of the present disclosure may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydrodyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the disclosure may contain modified phosphorous, oxygen heteroatoms in the phosphate backbone, short chain alkyl or cycloalkyl intersugar linages or short chain heteroatomic or heterocyclic intersugar linkages. For example, the antisense oligonucleotides may contain phosphorothioates, phosphotriesters, methyl phosphonates, and phosphorodithioates. For example, phosphorothioate bonds may link only the four to six 3'-terminal bases, may link all the nucleotides or may link only 1 pair of bases.

The antisense oligonucleotides of the disclosure may also comprise nucleotide analogs that may be better suited as therapeutic or experimental reagents. An example of an oligonucleotide analogue is a peptide nucleic acid (PNA) in which the deoxribose (or ribose) phosphate backbone in the DNA (or RNA), is replaced with a polymide backbone which is similar to that found in peptides (P. E. Nielson, et al Science 1991, 254, 1497). PNA analogues have been shown to be resistant to degradation by enzymes and to have extended lives in vivo and in vitro. PNAs also form stronger bonds with a complementary DNA sequence due to the lack of charge repulsion between the PNA strand and the DNA strand. Other oligonucleotide analogues may contain nucleotides containing polymer backbones, cyclic backbones, or acyclic backbones. For example, the nucleotides may have morpholino backbone structures (U.S. Pat. No. 5,034,506). Oligonucleotide analogues may also contain groups such as reporter groups, a group for improving the pharmacokinetic properties of an oligonucleotide, or a group for improving the pharmacodynamic properties of an antisense oligonucleotide. Antisense oligonucleotides may also incorporate sugar mimetics as will be appreciated by one of skill in the art.

Antisense nucleic acid molecules may be constructed using chemical synthesis and enzymatic ligation reactions using procedures known in the art based on CRP40 amino acid sequence information such as that provided. The antisense nucleic acid molecules of the disclosure, or fragments thereof, may be chemically synthesized using naturally occurring nucleotides or variously modified nucleotides designed to increase the biological stability of the molecules or to increase the physical stability of the duplex formed with mRNA or the native gene, e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The antisense oligonucleotides may be introduced into tissues or cells using techniques in the art including vectors (retroviral vectors, adenoviral vectors and DNA virus vectors) or physical techniques such as microinjection. The antisense oligonucleotides may be directly administered in vivo or may be used to transfect cells in vitro which are then administered in vivo.

In another embodiment, siRNA technology can be applied to prevent expression of CRP40 or mortalin-2. Application of nucleic acid fragments such as siRNA fragments that correspond with regions in CRP40/mortalin-2 and which selectively target the CRP40/mortalin-2 gene may be used to block CRP40/mortalin-2 expression resulting in a reduction of platelet aggregation. Such blocking occurs when the siRNA fragments bind to the CRP40/mortalin-2 gene thereby preventing translation of the gene to yield functional CRP40/mortalin-2.

SiRNA, small interfering RNA molecules, corresponding to CRP40/mortalin-2 are made using well-established methods of nucleic acid syntheses including automated systems. Since the structure of the CRP40/mortalin-2 gene is known, fragments of RNA that correspond therewith can readily be made as outlined above with respect to antisense oligonucleotides. The effectiveness of selected siRNA to block CRP40/mortalin-2 activity can be confirmed using a CRP40/mortalin-2-expressing cell line. Briefly, selected siRNA is incubated with a CRP40/mortalin-2-expressing cell line under appropriate growth conditions. Following a sufficient reaction time, i.e. for the siRNA to bind with CRP40/mortalin-2 DNA to result in decreased expression of the CRP40/mortalin-2 DNA, the reaction mixture is tested to determine if such decreased expression has occurred. Suitable siRNA will prevent processing of the CRP40/mortalin-2 gene to yield functional CRP40/mortalin-2. This can be detected by assaying for CRP40/mortalin-2 function in the reaction mixture, for example, CREB activity.

It will be appreciated by one of skill in the art that siRNA fragments useful in the present method may be derived from specific regions of CRP40 or mortalin-2-encoding nucleic acid. Moreover, suitable modifications include, for example, addition, deletion or substitution of one or more of the nucleotide bases therein, provided that the modified siRNA retains it ability to bind to the targeted CRP40/mortalin-2 gene. Selected siRNA fragments may additionally be modified in order to yield fragments that are more desirable for use. For example, siRNA fragments may be modified to attain increased stability in a manner similar to that described for antisense oligonucleotides.

Embodiments of the present disclosure are described by reference to the following specific examples which are not to be construed as limiting.

The following experimental work is described by reference to the methods and materials used, as well as by reference to the results obtained.

Example 1

Characterization of Human CRP40

Methods and Materials
Generation of BQ224193 primers synthesized by MOBIX, McMaster University:

Human Brain RNA (Ambion) was reverse transcribed using MuLV Reverse Transcriptase (Applied Biosystems) and a fragment of 720 base pairs (Genbank #BQ224193) was amplified using 5' atg gat tct tct gga ccc aag cat 3' (Sense primer) (SEQ ID NO:3) and 5' tcg ttc ctt ctt tgg ccg gtt ttt t 3' (Antisense primer) (SEQ ID NO:4) designed by MOBIX, McMaster University. The conditions used were: 95° C., 2.25 minutes (min), 95° C.-15 sec, 60° C.-30-sec, 72° C.-55-sec, 40 cycles 72° C.-7.0-min. The PCR product was run on a 1% agarose gel with 1×TAE and 0.05% ethidium bromide (EtBr). The band at 720 relative to a 100 bp marker (Biorad) was cut out, purified using a Qiagen gel extraction kit, and sequenced.
Cloning BQ224193

Bam HI and EcoRI restriction enzyme sites were introduced 5' of sense and antisense primers, respectively, to facilitate cloning. Subsequent RT-PCR and analysis of the products revealed a 740 bp fragment, which was purified from an agarose gel as described above. The PGEX-2T vector (Invitrogen) and the 740 bp fragment were digested using the restriction enzymes as below: 0.5 µg (1 µl of 500 µg/µl) vector, 4.0 µl of 10×Y+/Tango buffer, 1.0 µl BamHI (5 U), EcoRI, 1.0 µl (5.0 U), 13.0 µl DH2O, 32 µl BQ224193-740 bp fragment (0.6 µg), 8 µl 10×Y+/Tango buffer, 2.0 µl BamHI (10 U), 2.0 µl EcoRI (10 U); mixed and incubated at 37° C. for 1 hour (h) and enzymes were inactivated at 75° C., 15 min. The digested vector and human CRP40 fragments were run on a 0.7% agarose gel with 0.05% EtBr in separate lanes with 1 KB ladder as marker. The bands at 1.8 Kb and 740 bp were cut out separately and purified using gel Extraction kit. (Qiagen). The 740 bp fragment was ligated to PGEX-2T vector as follows: cut 740 bp BQ224193 DNA, 14.0 µl, cut pGEX-2T, 2.0 µl, 10× ligase buffer, 2.0 µl, T4 DNA ligase (Fermentas), mixed and incubated at 22° C. for 1 h, and enzyme inactivated at 65° C. for 10 min. The products were frozen at −20° C. until transformation.
Preparation of BL21 E. coli cells and Transformation Competent cells were prepared as follows. BL-21 E. coli (Invitrogen) lypholized powder was resuspeneded in 1.0 ml LB medium in a shaker at 37° C., 250 rpm overnight. The E. coli was then plated on LB agar plates. Following a 24 hr incubation, 1 ml of LB was inoculated using a single colony in a 15 ml Falcon tube and incubated overnight at 37° C., 250 rpm (New Brunswick Scientific Co. Inc, Series 25D). Following an 18 hr incubation, 100 ml of LB medium was inoculated with 200 µl of overnight culture and incubated at 37° C. at 200 rpm till OD 600 was 0.4-0.5 (approx-3.5 hrs). The culture was spun down at 2000 rpm for 5 min and the pellet was re-suspended in 1.0 ml Of CaCl2 solution (50 mM CaCl2, 10 mM Tris-HCL, pH 8.0) and 24 ml CaCl2 solution. The solution was then incubated on ice for 15 min, spun at 2000 rpm for 5 min and the pellet re-suspended in 3 ml of CaCl2 solution. The competent cells were used fresh for subsequent transformation. Transformation: 20 µl ligated mix was mixed with 200 µl competent cells, incubated on ice for 45 min, then in a 42° C. water-bath for 2 min. and chilled briefly on ice. Transformed cells (100 µl) were mixed with 900 µl LBG (20 mM glucose in LB medium) and incubated at 37° C. for 1 hr without shaking. Uncut vector was also transformed side by side. Following 1 hr, 100 µl of BQ transformed cells, 100 µl of uncut vector transformed cells and competent cells were plated on LB agar plates with ampicillin and incubated overnight at 37° C.
Preparation of BQ Protein:

The following day, colonies were picked, inoculated (1.5 ml eppendorf tubes) and placed on a shaker (250 rpm) and the next day, 3.0 ml LB ampicillin media were mixed with 50 µl of overnight grown culture until OD600 was 0.5. IPTG (100 mM) was added to each tube which were then incubated for 22 hrs h at 14° C. and spun down at 13000 rpm for 30 sec. The supernatant was discarded. The pellet was re-suspended in 300 µl of IX-PBS and centrifuged at 13000 rpm for 30 sec. It was then washed with IX-PBS 2×. Glutathione elution buffer (10 µl) was added to the beads, incubated for 5 min, centrifuged 13000 rpm, 5 min. The supernatant was transferred to fresh tubes to which was added 10 µl of loading buffer. All above fractions were loaded on SDS-PAGE.
Sodium Dodecyl Sulfate Polyacrylamide Gel Electrophoresis (SDS-PAGE)

Protein concentration was determined using the Bradford method. Briefly, IO µg of protein was mixed with sample buffer (0.625 M Tris, 2% SDS, 0.05% β-mercaptoethanol, 10% glycerol, 0.01% bromophenol blue, pH 6.8) and boiled for 4 min (Bradford 1976). SDS-PAGE (12% acryl amide) was used with the following procedure: running buffer (0.025 M Tris, pH 8.3, 0.3 M glycine, 0.1% SDS) and 65V was applied. The pellet was re-suspended in 20 µl IX-PBS for SDS-PAGE analysis. The supernatant was mixed with 50 µl of 50% Glutathione Sepharose 4B at room temperature for 5 min. 100 µl IX-PBS was added and then the mixture was centrifuged at 13000 rpm, 30 sec. The pellet was washed with IX-PBS 2× and Glutathione elution buffer (10 µl) was added to the beads, incubated for 5 min, centrifuged 13000 rpm, 5 min. Lastly, the supernatant was transferred to fresh tubes and 10 µl of loading buffer was added. AU above fractions were then loaded onto SDS-PAGE.
Production of Polyclonal Antibody Using BQ Fusion Protein 0.5 µg of the pure BQ protein was run in each lane of 10% acrylamide gel and transferred onto a nitrocellulose filter paper (binding capacity of 26 µg/cm2). Ponceau-S stained BQ bands were cut out and stored at −20° C. Approximately 30 µg BQ protein was homogenized and required for the first injection. Two New Zealand rabbits were used and the following protocol was employed: injected BQ slurry subcutaneously (s.c.) on the nape of the neck at 4 injection sites (250 µg each injection site) on the following injection days, 0, 14, 42, 134 and bleeds were performed on days 13, 32, 50, 89, and 146. Approximately 100 ml of blood was collected from each rabbit and the serum was collected and centrifuged and 0.2% sodium azide was added to the aliquots.
Purification of BQ antibody Protein A antibody purification kit from Sigma was used and is briefly described. 10 ml of the crude BQ serum was used for antibody purification. 10 fractions of 1.0 ml were collected from the column, checked OD 28 OnM and purified BQ antibody was aliquoted and stored at −80° C.

Functional Studies—Protein-Binding Assays

Tritiated N-propylnorapomorphine ([3H]-NPA) binding was performed with BQ-fusion protein in the presence of cold dopamine (DA). Briefly, the assays were performed in triplicate and consisted of the following solutions and protocol: 50 mM TRIS, 5.0 mM mgCl2, 1.0 mM EDTA, 0.lmM DTT, 0.lmM PMSF, 100 mg/ml Bacitracin and 5.0 mg/ml soybean trypsin; DA (mw=189.6) was dissolved in 0.1% ascorbic acid; each tube was vortexed briefly and incubated in a shaking water bath at 37° C., for 2 h; receptor binding equipment (Brandel, U.S.A.) washed 3 times with distilled water; then repeated washes in assay buffer, 50 nM TRIS, 1 mM EDTA, pH 7.4; 18 test-tubes were set on the binding platform and fiberglass filter paper was put on the platform. The samples were passed through the filter paper with 3 consecutive washes; placed in the scintillation tubes and 5.0 ml Biodegradable Counting Scintillant was added and radioactive counts were measured (Amersham, U.S.A.).

Studies on DRD2 Transfected SH-SY5Y Human Neuroblastoma Cells

The SH-SY5Y cell line (obtained from ATCC) used in this study has been extensively characterized. This cell line does not express endogenous dopamine receptors, therefore the cells were transfected with dopamine D2 long isoform using the following method. The dopamine DRD2 receptor was subcloned into a mammalian expression vector (pcDNA 3.1 (+)), which was generously donated by Guthrie cDNA Resource centre (Pennsylvania, U.S.A.). This plasmid DNA was prepared in bulk using TOPOIO chemically competent *E. coli* from Invitrogen. Briefly, 1 colony was inoculated with 5 ml of LB Ampicillin and incubated at 37° C., at 250 rpm for 8 h. Culture (0.5 ml) was transferred to 250 ml LB Ampicillin in 500 ml flasks, incubated at 37° C. in shaker unit (275 rpm, 24 h) (New Brunswick Scientific Co. Inc, Series 25D). Culture was removed, transferred and centrifuged and remaining pellet was processed for the extraction of DNA as previously described (QIAGEN Plasmid Purification Protocol). The DNA was quantified by spectrophometry (Beckman 640), aliquoted and stored at −80° C.

Transfection of SH-SY5Y Cells

The pcDNA 3.1(+) vector was introduced into SH-SY5Y cells by lipofection method (Invitrogen Life Science technology. U.S.A.). Briefly, 24 µg of DRD2 plasmid DNA was mixed with 1.5 ml of Opti MEM media and 60 µl of lipofectamine 2000 reagent was added and mixed with 1.5 ml of Opti MEM media and SH-SY5Y cells. Geneticin-resistant clones stably expressing the D2L receptor were screened by a [3H] spirerone-binding assay and was maintained in RPMI medium (RPMI contained 10% fetal bovine serum, 1 mM glutamate, 50 U/ml of penicillin, and 50 U/ml of streptomycin) with 200 µg/ml of geneticin. Cells were grown to confluency (5-6 days following sub-culturing) in fresh RPMI medium.

Homogenizing Subcellular Fractions: Nucleus, Mitochondria, Supernatant (Cytosol)

SH-SY5Y cells were scraped off and this procedure was repeated a second time. The cells were incubated 5 min, centrifuged at 2000 rpm for 5 min and the supernatant was discarded. The pellet was re-suspended in 0.5 ml 0.35M sucrose buffer (wPMSF), homogenized and centrifuged at 1000 g for 10 min. The supernatant was centrifuged and the pellet was re-suspended in a 0.32M sucrose buffer (wPMSF), homogenized, and centrifuged. The pellet was re-suspended 0.053 ml Tris-EDTA PMSF and labeled as nuclear fraction 1. The supernatant was centrifuged and the resulting supernatant was stored and labeled cytosolic fraction 1. The remaining pellet was re-suspended in 0.150 ml Tris-EDT A-PMSF and labeled mitochondrial fraction 1.

Each cell fraction was exposed to: 1) 100 µM DA; 2) 100 µM Haloperidol; 3) both 100 µM DA and 100 µM Haloperidol; 4) and a negative control. The cells were exposed to the neurotransmitter and/or the neuroleptic (antipsychotic) and left overnight. Western immunoblotting with BQ primary antibody was performed, followed by immunoblotting with polyclonal conjugated horseradish peroxidase secondary antibody.

RNA Ligase-Mediated Rapid Amplification of 5' and 3' cDNA Ends (RLM-RACE PCR)

Total RNA from human brain was purchased from Ambion and used as the cDNA library to amplify BQ gene specific primers. The RLM-RACE-PCR kit was purchased from Invitrogen (Invitrogen life technologies, California, U.S.A.). First, human brain total RNA was treated with calf intestinal phosphatase to remove the 5' phosphates from truncated mRNA and all other non-mRNA. Briefly, 2.5 µl total RNA, 1.0 µl 10×CIP buffer, 1.0 µl RNase out, 1.0 µl CIP enzyme, and 4.5 µl DEPC water were mixed in 1.0 µl microcentrifuge tube, vortexed and centrifuged and incubated in a 50° C. water bath for 1 h, then centrifuged and put on ice; precipitated RNA, added 90 µl DEPC water and 100 µl phenolxhloroform, vortexed 30 sec, centrifuged 5 min at RT and to the transferred aqueous phase was added 2 µl 10 mg/ml mussel glycogen and 10 µl 3M sodium acetate, pH 5.2, followed by mixing. Then, 220 µl 95% ethanol was added, followed by vortexing. The mixture was placed on dry ice for 10 min, centrifuged and the supernatant was removed. Then, 500 µl 70% ethanol was added to solubilize RNA pellet. The solution was then centrifuged for 2 min, 4° C. The supernatant was removed and the pellet was re-suspended in 7 µl DEPC water. The next major step involved was to treat the dephosphorylated RNA with tobacco acid pyrophosphatase to remove the 5' cap structure from full length mRNA. Briefly, added and mixed 7 µl dephosphorylated RNA, 1 µl 10×TAP buffer (40 U/µl), 1 µl RNaseOut, 1 µl TAP (0.5 u/µl), mixed, vortexed and centrifuged, incubated at 37° C. lh. Repeated exactly as above precipitation procedure. Following decapping of the mRNA, the next step was to ligate a gene specific Gene Racer RNA Oligo to the 5' end of the Ambion human brain total RNA. Briefly, added 7 µl of the decapped RNA into a tube containing the pre-aliquoted lipophilized GeneRacer RNA Oligo (0.25 µg), mixed and centrifuged; then incubated in water bath at 65° C. and placed mixture on ice for 2 min. The following reagents were then added to the centrifuged mixture: 1 µl, 10× lysate buffer, 1 µl 10 mM ATP, 1 µl RNaseOut (40 U/µl), 1 µl T4 RNA ligase (5 U/µl), incubated for 1 h at 37° C., and briefly centrifuged and placed on ice. Repeated exactly as above precipitation procedure. The 5' ligation step provided the GeneRacer RNA Oligo ligated to the decapped mRNA, which required reverse transcription into complementary cDNA. Briefly, added 1 µl hexamer primer and 1 µl dNTP, mixed to ligate RNA, incubated at 65° C. for 5 min, followed by placing mixture on ice for 2 min and centrifuging. Next, the following reagents were added: 12 µl ligated RNA and primer mixture; 4 µl 5× First strand Buffer, 2 µl 0.1 M DTT, 1 µl RNaseOut (40 U/µl), 1 µl Superscript 111 (200 U/µl), then mixed solution and incubated at 50° C. for 50 min. RT-reaction was inactivated at 70° C., and centrifuged. Then 1 µl RNase H (2 U) was added to the RT-reaction at 37° C., 30 min. The protocol for PCR was as follows: 94° C., 2.0 min, 1 cycle; 94° C., 30 sec, 5 cycles; 72° C., 2.0 min, 5 cycles; 94° C., 30 sec, 5 cycles; 70° C., 2.0 min, 5 cycles; 94° C., 30 sec, 20 cycles; 65° C., 30 sec, 20 cycles; 68° C., 2.0 min, 1 cycle; 68° C., 10 min, 1 cycle (Invitrogen Life Science Technologies).

RNA Isolation Using TRIzol Method

Approximately 50-00 mg of bovine, rat tissue, lymphocytes and neuroblastoma SH-SY5Y cells were used in the RNA isolation. The tissue was mixed with 1000 µl Tri-pure reagent and homogenized. Next, the solution was poured into a 1.5 ml micro-centrifuge tube and incubated at room temperature for 5 min. Immediately following, 200 µl of chloroform was added, shaken vigorously for 15 sec and allowed to sit 20 min. The samples were then centrifuged 12000 for 15 min, 4° C., centrifuged and colorless phase was removed and transferred to a new tube to which was added 500 µl isopropanol. The solution was allowed to precipitate for 10 min at room temperature, then centrifuged for 10 min at 12000 g and the supernatant was discarded. The pellet was re-suspended in 75% ethanol, centrifuged 5 min and allowed to dry. It was then suspended in 30 µl DEPC-treated RNase-free H2O. The RNA was incubated for 15 min at 55° C. and analyzed with a Beckman spectrophotometer DU-640 for RNA concentration and purity.

Isolation of Poly (A)+ RNA

Bovine tissues and neuroblastoma SH-SY5Y cells were removed and treated with TRIzol reagent (as previously described) to isolate total RNA. 200 µg total RNA was used to isolate the polyA RNA with Oligo Dt cellulose containing a capacity of 10 mg RNA per gram of resin. The following reagents were used in the polyA RNA isolation: 1) Binding buffer (pH final solution to 7.5), 10 mM Tris-HCl (pH 7.5), 0.5 M NaCl, 1 mM EDTA (pH 7.5), 0.5% SDS; 2) 2× Binding Buffer (pH final solution to 7.5), 20 mM Tris-HCl (pH 7.5), 1 M NaCl, 2 mM EDTA (pH 7.5), 1% SDS; 3) Wash Buffer (pH final solution to 7.5), 10 mM Tris-HCl (pH 7.5), 0.5 M NaCl, 1 mM EDTA (pH 7.5); 4) Elution Buffer (pH final solution to 7.5), 10 mM Tris-HCl (pH 7.5), 1 mM EDTA. The eluted poly(A)+ RNA was added to five 0.5-mL aliquots elution buffer, and a Beckman U-640 spectrophotometer was used to read A260 to determine aliquot with max Poly A.

Northern Blot

Twenty micrograms of polyA RNA from neuroblastoma SH-SY5Y cells, human tissue and bovine tissue were separated on 1.0% formaldehyde agarose gels and transferred to Hybond nylon filters (Amersham Pharmacia Biotec, England) which were baked at 80° C. for 2 h. Prehybrization involved 70 µl of salmon sperm DNA at 95° C. and Express-Hyb and rotated for 2 h at 68° C. The blot was hybridized to α-32P-dCTP-labelled cDNA probes for 22 h at 45° C., and washed with 2×SSC. The blots were exposed to Kodak X-ray film. A hybrization probe was prepared from a 720 bp fragment from BQ224194 primers. The pair of primers used consisted of the forward primer: 5' atg gat tct tct gga ccc aag cat 3' (SEQ ID NO:3) and reverse primer 5' tcg ttc ctt ctt tgg ccg gtt ttt t 3' (SEQ ID NO:4). The same filters were hybridized with a β-actin probe as an internal control of both the RNA integrity and amount.

Generation of the Standard Curve For Real-Time PCR Experiments:

A standard curve was used for absolute quantification of the unknown SH-SY5Y cDNA samples with 6 concentrations (1pg-10 ag) of cDNA. The following protocol was used to produce the first and second PCR reaction to make a pure cDNA amplicon with SH-SY5Y cDNA and forward BQ primer, 2 and reverse primer, 4: 1st PCR reaction, 5O mM mgCl2, 0.75 µl, 1O× Buffer, 2.5 µl, 2.4 Primer mix, 2.0 µl, SH-SY5Y cDNA sample #1, 2.5 µl, Platinum Taq, 0.2 µl, DEPC water, 14.55 µl; 95° C., 2.25 min, 95° C., 15 sec, 60° C., 30 sec, 72° C., 1.0 min, 72° C., 7.0 min; 2nd PCR reaction, 50 mM mgCl2, 1.5 µl, 1O× Buffer, 5.0 µl, 2.4 Primer mix, 4+4 µl, SH-SY5Y cDNA sample #1, 5.0 µl, Platinum Taq, 0.4 µl, DEPC water, 29. 10 µl, and ran PCR with the same conditions. Purification of SH-S Y5Y cDNA PCR Product QIAGEN minielute PCR Purification Kit.

Calculations in Copy Number per microgram of RNA for Real-Time PCR Experiment:

The following formula was used to determine copy number for the standard curve:

$$\# \text{ Copies}/\mu l = \frac{\text{Concentration }(g/\mu l) \times 6.032 \times 10^{23}}{\text{Length in base pairs } \times 660}$$

Real-Time PCR Protocol with D2L-Transfected SH-SY5Y cDNA:

D2L-transfected SH-SY5Y cells, Haloperidol-treated were compared to the same Neuroblastoma cells not treated with HAL, which acted as a control. All samples were performed in duplicate, and samples were also prepared in duplicate, as a No Template Control (NTC) and No Reverse Transcriptase Control (NRT). The following protocol was used: 2× SYBRgreen, 10.0 µl, Forward primer, P2, 1.2 µl, Reverse primer, P4, 1.2 µl, Reverse Transcriptase Mix, 0.2 µl, DEPC H2O, 6.4 µl, SH-SY5Y cDNA, 1.0 µl; Real-Time PCR Conditions, 50° C. 30 sec (1 cycle), 95° C. 15 min (1 cycle), 95° C. 15 sec (40 cycles), 60° C. 30 sec (40 cycles), 72° C. 40 sec (40 cycles).

Localization Studies of Human CRP40—Immunohistochemistry Protocol with Post-Mortem Brain Slide Samples of the Nucleus Accumbens from The Stanley Foundation Neuropathology Consortium:

Three slides were chosen from the 60 samples generously donated by The Stanley Foundation. The slides consisted of: 1) control; 2) schizophrenia patient-drug free; 3) schizophrenic patient-15000K, HAL-treated. The slides were incubated with 4% formaldehyde and diluted in PBS for 30 min. Immediately following, washed sections 3 times with PBS for 5 min, each time and dried off each slide as close as possible to the tissue and outlined the section with the hydrophobic pen. The sections were then blocked by incubating sections with 3% normal goat serum*(NGS) (diluted in PBS containing 0.6% Triton X-100) for 1 h. Next, incubated slides with primary human CRP40 polyclonal antibody diluted in PBS containing 0.6% Triton X-100 (and 3% NGS if necessary) overnight at 4° C. (wrapped in aluminum foil). The following day, the slides were washed 3 times with PBS for 5 min, each time, and incubated slides with FITC secondary antibody diluted in PBS containing 0.6% Triton X-100 for 4 h. Next, the sections were washed 6 times in PBS and slides were mounted with appropriate cover-slips and fixed with nail polish.

Results

RT-PCR Showed Combinations of BQ224193 Primers Produced 3 Discrete Bands, all Containing Significant Homology to the mot-2 Sequence RT-PCR with Ambion human brain cDNA was performed utilizing 2 forward primers and 3 reverse primers from the BQ224193 sequence in different combinations, resulting in 3 distinct bands (see FIG. 1). The largest band consisting of 720 bp was used in the cloning part of the experiment due to the sharpness of the band and its increased size compared to other primer mixtures with 1.2% agarose gel and 15 µl EtBr (5 mg/ml). The bands were eluted out and sent for sequencing at MOBIX, McMaster University. Sequencing analysis results consistently showed 96% nucleotide homology to mot-2.

Figure 2:
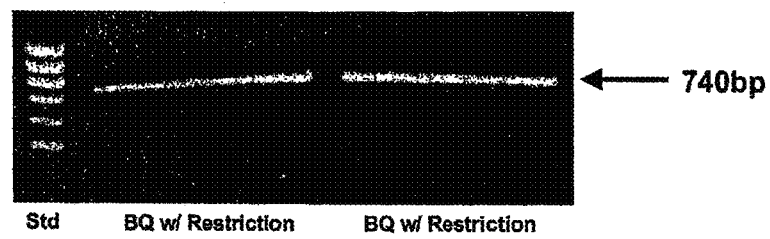
FIG. 2 illustrates that a 740 bp band was identified by gel electrophoresis on a restriction enzyme digestion of the BQ224193 forward and reverse primers (p1 and p5, respectively) which was performed prior to transfection of the BQ224193 fragment.

RT-PCR Fragment Using Modified Primers Containing Restriction Enzymes BamH 1 and EcoRI, Ligation and Transformation into BL-21 E. coli Cells The following primers were synthesized in order to incorporate the restriction enzyme sites into the known 720 bp BQ fragment, which resulted in a slightly larger nucleotide fragment of 740 bp (see FIG. 2). The following 5' primer including a BamHIsite: tag gga tcc atg gat tct tct gga ccc aag cat (SEQ ID NO: 1); and 3' primer including an EcoRI site, cta gaa ttc tca tcg ttc ctt ctt tgg ccg gtt ttt (SEQ ID NO: 2) were used to perform the RT-PCR reaction.

The glutathione S-transferase (GST) gene fusion system was used in these experiments because integration of the BQ transgene, expression, purification and detection of the fusion protein in E. coli is reliable, fast and reproducible. The pGEX plasmids function as being inducible with high expression of genes and transgene fusions with Schistosoma japonicum GST. Furthermore, the pGEX-2T vector contains a Taq promoter site in order to chemically induce high expression of the Lad gene. Isopropyl βD-thiogalactosidase (IPTG), a lactose analog, was used to induce expression of the Lac gene, ultimately translating high quantities of BQ fusion protein.

The digestion of the 740 BQ fragment and pGEX-2T was performed using the specific restriction enzymes noted above, in order to provide the sticky ends for the ligation into the vector. Following ligation and transformation into BL-21 E. coli cells, the transformants were grown on Ampicillin resistant agar plates at 37° C. overnight. The colonies were picked and grown in LB media with Ampicillin overnight. Producing fusion protein involved using 500 ml LB media, 10 ml overnight culture, 500 µl Ampicillin in baffled flask. Translation was initiated following the addition of 500 µl IPTG. The mixture was placed in a refrigerated shaker, 12° C., 250 rpm for 23 h.

Figure 3:
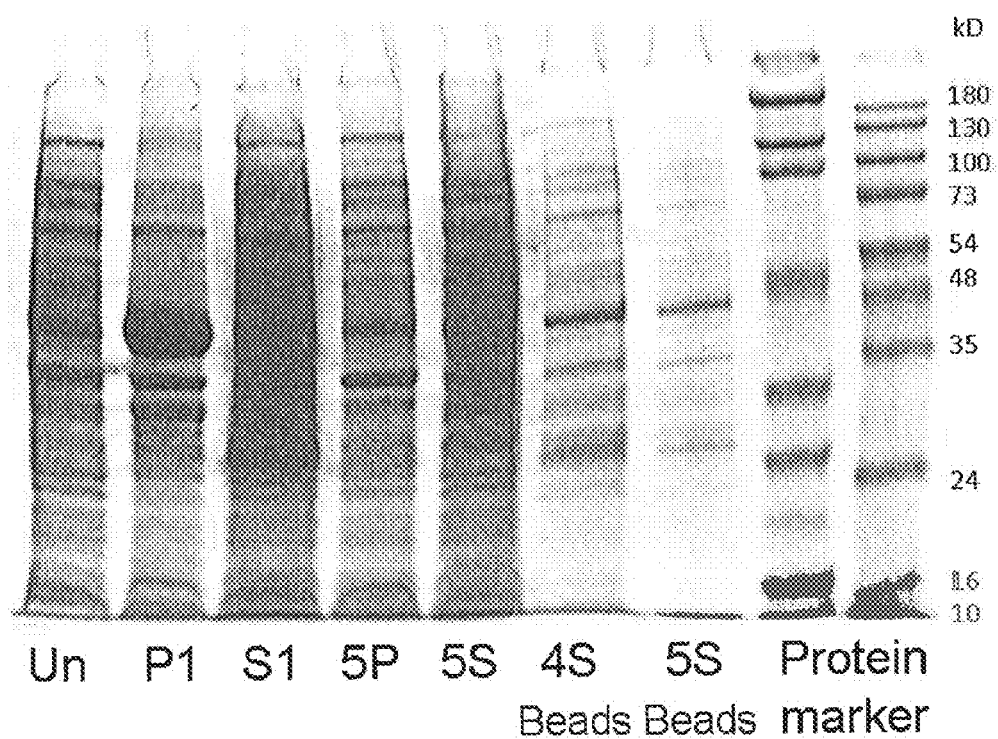
FIG. 3 illustrates by acrylamide gel electrophoresis results using Coomassie blue that, following the transformation and growth of the BQ224193 fusion protein fragment, growing the fusion protein at 12° C. resulted in the largest portion of fusion protein in the soluble state.
Figure 4:
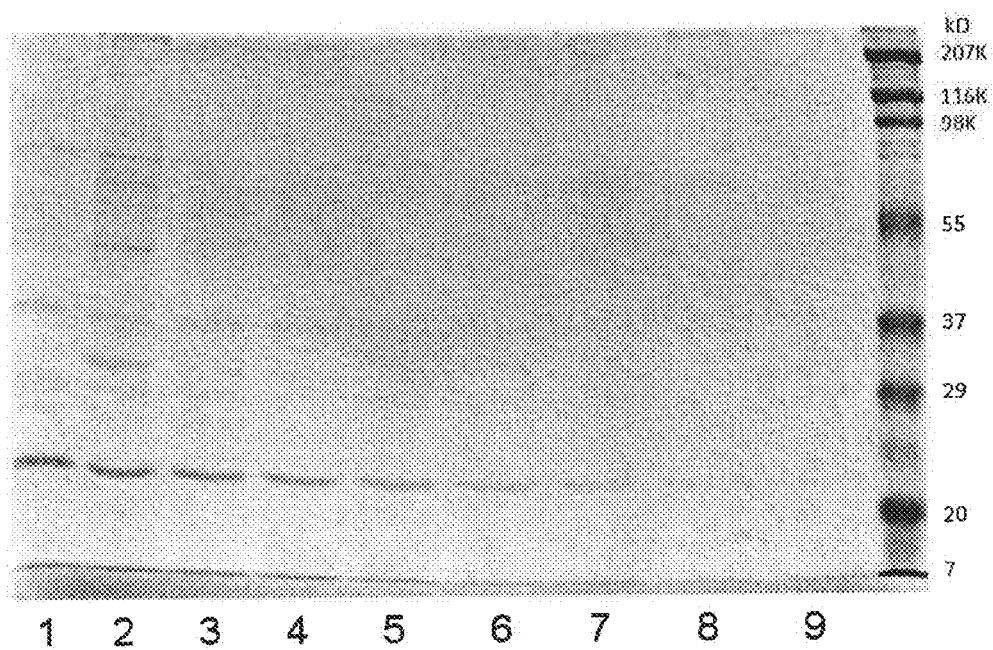
FIG. 4 illustrates that pure, isolated 23 kDa fusion protein was produced on cleavage with thrombin protease from the vector.

The optimal temperature for the BQ fusion protein was 12° C., in order to allow proper protein folding thereby allowing the fusion protein to remain in its soluble form and allowing it to be actively functional. The next day, the mixture was centrifuged and the pellet of cells was re-suspended in 1×PBS including a mini-C protease inhibitor tablet. The cells were lysed using a French press. The released fusion protein was allowed to bind to the matrix of Glutathione Sepharose 4B beads overnight. The bound fusion protein-Glutathione Sepharose matrix was added to an affinity chromatography column. As can be seen in FIG. 3, the majority of the fusion protein was in soluble form, which indicates that the protein was in its proper active state. Fractions were eluted out through the column and protein concentration was determined by spectrophotometry Following washes, the bound fusion protein was cleaved from the Glutathione Sepharose beads at specific sites by adding the enzyme thrombin protease, and SDS PAGE electrophoresis was performed on cleaved product. Coomassie staining was also performed on the gel (see FIG. 4).

Protein Binding Studies

Figure 5:
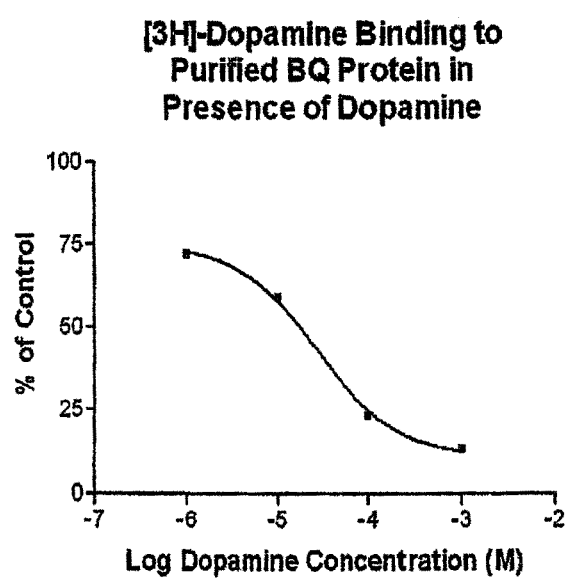
FIG. 5 graphically illustrates the results of protein binding assays which show that recombinant human CRP40 binds catecholamines in a manner similar to rat and bovine CRPs.

The first protein binding study involved [3+H]NPA and 3 different concentrations of displacement molecules (DA, NPA), 100 µM, 10 µM and 1 µM, respectively. Following protein binding, DPM counts were performed in a Beckman scintillation counter. The amount of displacement for each concentration was as follows: 100 µM DA-78.6%, 10 µM DA-74.6%, 1 µM DA-55% and 100 µM NPA-76.3%, 100 µM NPA-75%, 100 µM 64.3% (see FIG. 5).

The second binding study involved [3+H]DA and 4 different concentrations of displacement molecule DA, 1000 µM, 100 µM, 10 µM and 1 µM, respectively. Following protein binding, DPM counts were performed in a Beckman scintillation counter. The amount of displacement for each concentration was as follows: 1000 µM DA-75%, 100 µM DA-65%, 10 µM DA-60%

Production of Human CRP40 Polyclonal Antibody with BQ Fusion Protein

34 µl of pure BQ protein was loaded on a 12% acrylamide gel and electrophoresis proceeded. The protein was then transferred to nitrocellulose paper and distinct single bands at approximately 23 kDa were identified using Ponceau-S staining. The bands were carefully cut out as close to the bands as possible with sharp scissors. Next, the bands were cut into very small pieces, placed in a 1.5 ml dounce hand homogenizer and crushed in 1ml 1×PBS. The solution was a milky white mixture that was quite consistent. Approximately 30 µg was injected into each of 2 New Zealand rabbits. Following 4 injections and numerous bleeds (described in the methods and materials), the animals were sacrificed and the serum was removed and purified. Following Western immunoblotting with numerous BQ antibody concentrations, a 1:4000 BQ antibody concentration showed the best results. Western Immunoblots demonstrated a strong distinct band at approximately 40 kDa and a less distinct band at 70 kDa (see FIG. 5).

RLM-RACE PCR cDNA isolated from the human brain cDNA library (Ambion) using the Invitrogen RACE kit resulted in a successful sequencing of the 3' end of the BQ gene. Results of sequencing by MOBDC showed that this stretch of PCR product was 96% homologous with mot-2 gene. Optimization of the PCR conditions, such as: 1) decreasing annealing temperatures; 2) increasing number of cycles; 3) addition of reducing agents, DMSO; 4) addition of betaine in order to straighten out secondary structures; 5) and making RACE cDNA with a thermal reverse transcriptase (superscript III) all failed to produce a positive band for the 5' end of the BQ gene.

RLM-RACE PCR Results with BQ Primers and Hela Cells as a Positive Control.

Figure 6:
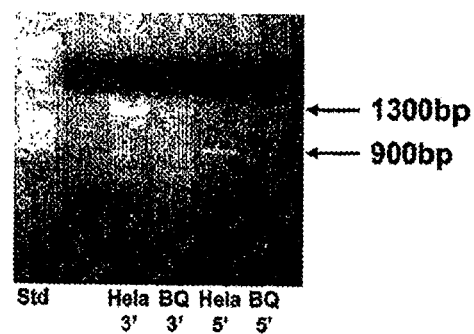
FIG. 6 shows RLM-RACE PCR results with BQ primers and Hela cells as a positive control.

The DA D2 receptor was transfected into the SH-SY5Y Neuroblastoma cells because they are not found endogenously in this particular cell-line. Addition of either 100 µM DA, 100 µM Haloperidol or a combination of both resulted in a significant increase of BQ expression compared to controls in the SH-SY5Y cells (see FIG. 6).

Northern Blot

Figure 7:
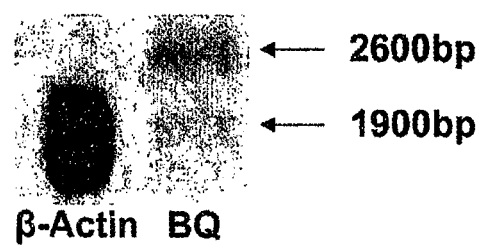
FIG. 7 illustrates the results of a Northern Blot Analysis using 50 μg SHSY5Y Neuroblastoma Poly A RNA and a P32cDNA probe with Human Ambion Brain RNA and p1, p5 primers. The blot was stripped and re-probed with Beta-Actin for proper size determination.

The first attempt of the northern blot involved the use of total RNA from: rat STR; bovine STR; human STR; human heart; human liver and SH-SY5Y cells. The subsequent blot showed a distinct band at the 2.8 kb level relative to the standard, and a slight band could be seen at the 1.9 kb level representing the BQ transcript (see FIG. 7). The northern was repeated using 20 µg polyA RNA and the results showed two distinct bands at 2.8 kb representing mortalin and 1.9 kb representing the human CRP40 protein, especially evident in SH-SY5Y cells. This was the first quantitative evidence that human CRP40 is alternative spliced variant from the mortalin gene. Furthermore, the northern provided information that the spliced variant is expressed in lower amounts than mortalin and it is specific in the CNS.

Real-Time PCR

Figure 8:
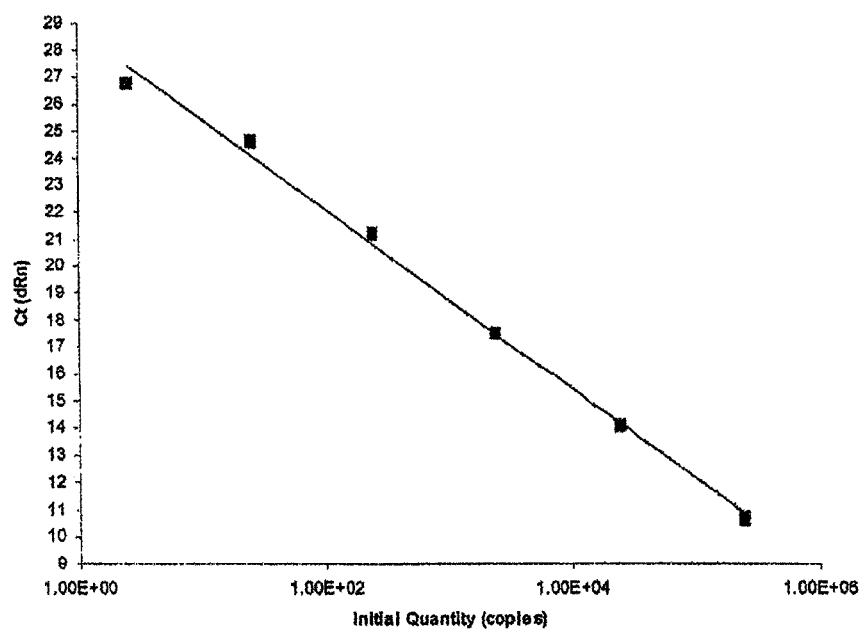
FIG. 8 is a standard curve by Real-Time PCR using BQ 2, 4 Primers, and SHSY5Y cells using Real-Time PCR.
Figure 9:
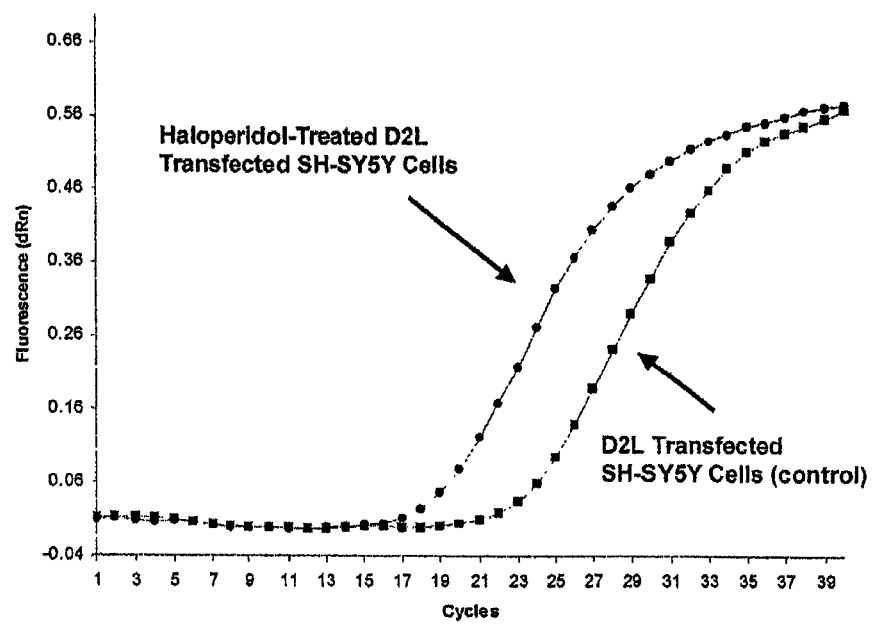
FIG. 9 is an amplication plot of SHSY5Y cells transfected with the DA D2L receptor comparing HAL-treated cells versus normal controls with Real-Time PCR.
Figure 10:
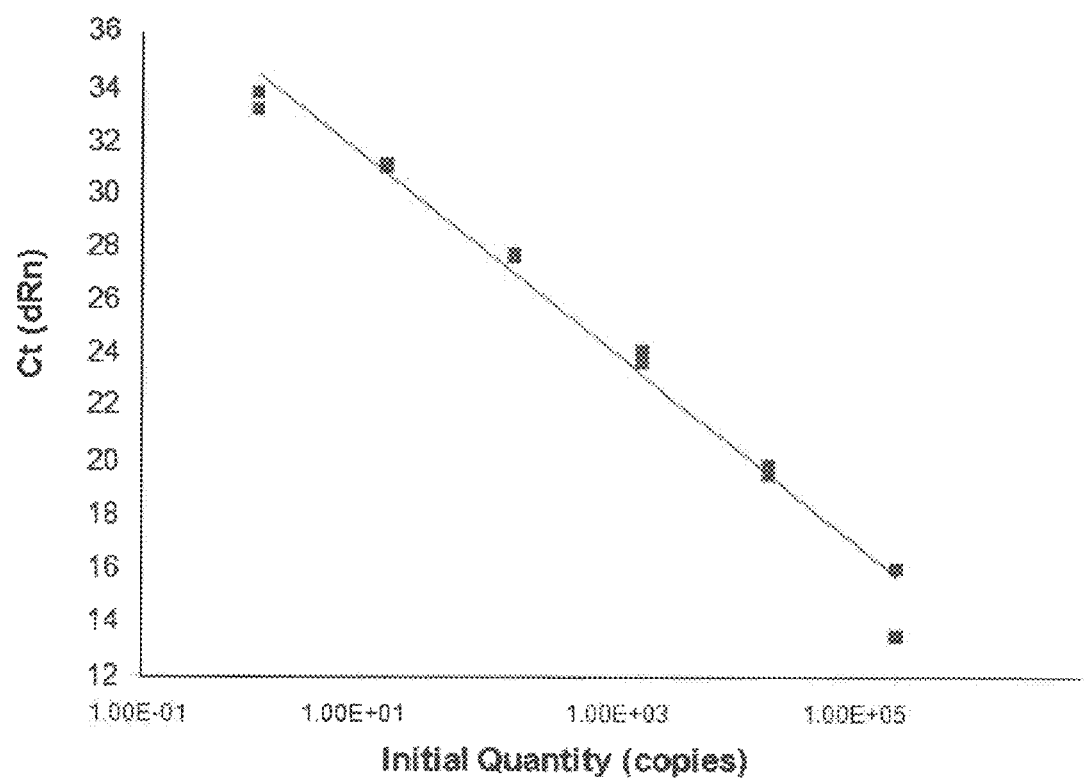
FIG. 10 graphically illustrates relative quantitation using the Housekeeping gene, human cyclophyllin with the same SHSY5Y cells.
Figure 11:
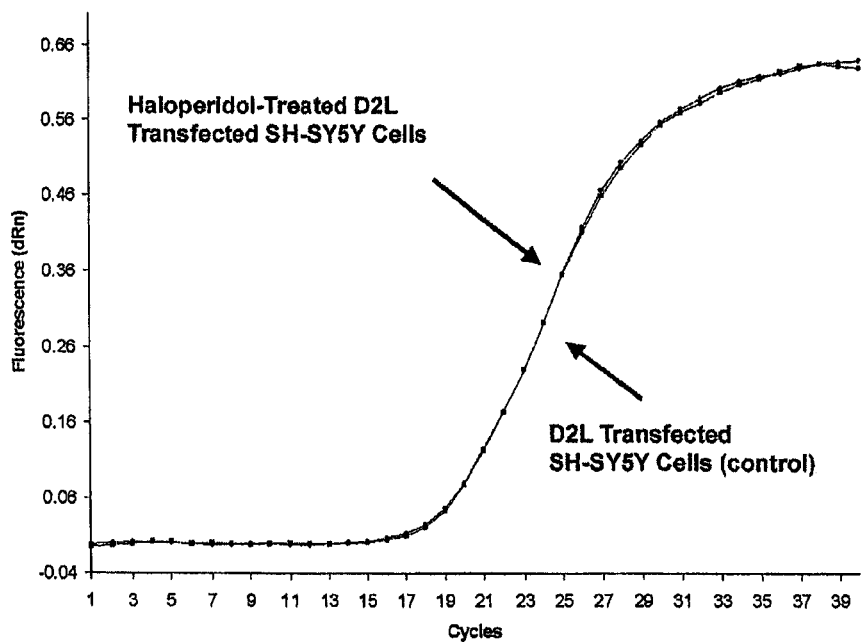
FIG. 11 is an amplification plot of Real-Time PCR using 100 ng cDNA from SHSY5Y RNA and cyclophyllin primers.

Two step Real-Time PCR (RT-PCR) was performed for quantification of mRNA in DAD2L transfected SH-SY5Y cells treated with HAL relative to normal SH-SY5Y cells. The two step RT-PCR was performed in duplicate for each sample using MX3000P Real-Time PCR (Stratagene). The primers used were forward: 5' TTGGCCGGCGATGT-CACGGATGTG-3' (SEQ ID NO:5) and reverse: 5'-ACA-CACTTTAATTTCCACTTGCGT-3' (SEQ ID NO:6) No primer dimers were detected and transcripts showed optimal PCR efficiencies. An absolute standard curve (FIG. 8) was constructed with the use of corresponding purified cDNA from control SH-SY5Y RNA sample in the range of 1pg-10 ag. MX3000P Real-Time PCR were optimized to ensure the amplifications were in the exponential phase and the efficiencies remained during the course of PCR. The results of the amplification showed that HAL-treated SH-SY5Y cells had a lower CT-value, which corresponded to approximately a 100% increase in initial template copies relative to the control cells (FIG. 9). These sensitive results show that HAL-treated cells, which result in increased DA release directly modulate the Human CRP40 transcript. Relative quantification was performed using the same SH-SY5Y cells as the previous experiment; however, human cyclophyllin was used as the housekeeping gene (FIGS. 10 and 11). The results showed that the CT-values of the DAD2L-treated SH-SY5Y RNA were the same relative to the control SH-SY5Y RNA.

Localization of Human CRP40 in Postmortem NA Brain Specimens

Figure 12:
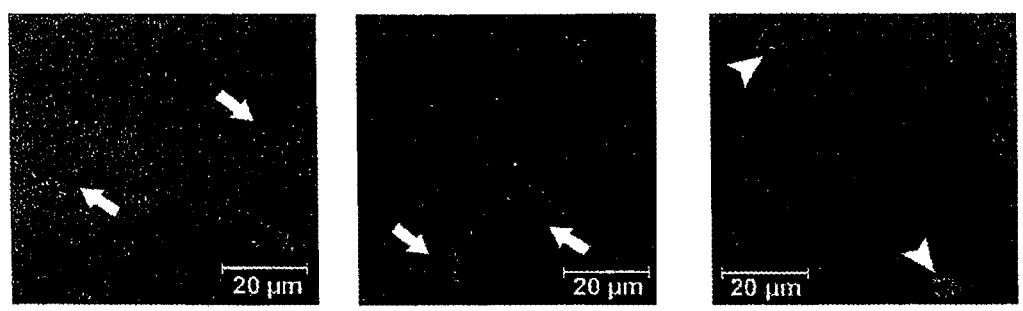
FIG. 12 graphically illustrates the results of localization studies using immunohistochemistry on postmortem brain specimens with human CRP40 as the primary antibody and FITC as the secondary florescent antibody.

Three slides containing post mortem brain specimens of the NA were used in immunohistochemistry studies. The primary antibody directed to human CRP40 was added in a dilution of 1:200 and the FITC secondary antibody was used as the fluorescent probe. The next day, the slides were analyzed using a confocal microscope (McMaster University). The results showed that human CRP40 is densely located in the perinuclear region in the control and schizophrenic specimen naive of drug treatment (FIG. 12). However, the slide containing the specimen that was treated with large doses of HAL, showed the antibody to be located almost exclusively within the nucleus.

Discussion

A human EST (Genbank Accession # BQ224193) has been used to identify a human brain CRP40 protein. Nucleic acid primers derived from this EST were used in RT-PCR to amplify a cDNA, which was cloned into the pGEX-2T bacterial expression vector. Functional studies of the recombinant fusion protein using [3H] propylnorapomorphine and [3H]DA clearly demonstrated that human CRP40 binds catecholamines. Furthermore, RACE-PCR was employed and the full-length gene sequence of this human CRP40 protein was elucidated. Northern blotting confirmed two discrete mRNA bands with human-CRP40 specific primers giving evidence that human CRP40 is an alternative spliced variant of the mot-2 gene. Real-Time PCR experiments were conducted with neuroblastoma SH-SY5Y cells treated with the typical neuroleptic, haloperidol (HAL) and CRP40 mRNA copy numbers were significantly expressed relative to normal control cells. Last, human CRP40 expression is found (at least) in both the lymphocytes and platelets of human blood.

Reverse transcriptase PCR was employed using specific BQ224193 primers with human, rat, and bovine striatal cDNA, and following agarose electrophoresis, 3 discrete bands were elucidated and sequencing analysis (MOBIX) of the PCR fragments showed 97% homology to the mitochondrial heat shock protein 70 kda, mortalin-2 (mot-2) (HSPA9) (see FIG. 1). Mot-2 is a 66 kDa protein, known to contain multifunctional properties. Most importantly, this protein is known to bind to the c-terminus of the tumor suppressor gene p53, preventing its transactivation to the nucleus, ultimately causing cell immortalization.

In order to determine if the BQ224193 fragment had catecholamine functional properties, cloning experiments were designed and performed using a pGEX-2T bacterial expression vector system, which were transformed in BL-21 *E. coli* cells. Following the production of 23 kDa recombinant fusion protein, protein sequence analysis from the University of Calgary confirmed the BQ224193 fusion protein to have 97% homology to the mot-2 protein.

Preliminary functional studies using protein binding assays were performed using [3H] propylnorapomorphine and [3H]DA with the recombinant BQ224193 fusion protein. The results in these experiments showed this novel protein fragment to significantly displace the titrated compounds with different concentrations of cold DA; giving direct evidence that this novel fusion protein fragment, referred to as human CRP40, has the ability to bind catecholamines with low affinity and with high capacity (see FIG. 5).

At this point, polyclonal antibodies were produced using the purified human CRP40 fusion protein. Following numerous injections of fusion protein and bleeds in two New Zealand rabbits, the animals were sacrificed on day 150. The polyclonal antibody produced a strong discrete band at approximately 40 kDa, and a weaker diffuse band at approximately 70 kDa in both rat and human striatal tissue, evidenced by Western immunoblotting.

Additional functional studies were conducted using DAD2L transfected SH-SY5Y cells that were homogenized in subcellular fractions, which included: 1) the cytoplasm; 2) the mitochondria; 3) and the nuclear fractions. Western blotting using SH-SY5Y tissue subtractions showed tissues exposed to elevated temperature of 42° C. resulted in a significant increase in human CRP40 levels, specifically in the nuclear fraction. The nuclear fraction tissue showed the most dramatic increase in human CRP40 protein, indicating that the CRP40 proteins translocate to the nucleus in the presence of stress such as heat or increased catecholamine exposure. Additional functional studies were conducted with SH-SY5Y cells that were exposed to 100 μM HAL and 100 μM DA, resulting in a significant increase in human CRP40 protein expression in the nuclear fraction relative to SH-SY 5Y control cells.

Following the cloning and characterization of the novel protein human CRP40, RLM-RACE PCR confirmed the complete sequence of human CRP40 protein. Initial sequencing results revealed that the entire BQ sequence to have 97% homology with the mot-2 gene at the C-terminus. From this point, it was hypothesized that human CRP40 is an alternative spliced variant from the 17 exon mot-2 gene (2.8 kb transcript). Using the Swiss-Prot ExPASy program allowed the conversion of the human CRP40 nucleotide sequence to the translated protein sequence. The results showed the novel human protein to have a molecular weight of 37.5 kDa and theoretical P.I. of 6.21. Resequencing indicated that CRP40 is at least 98% homologous, and perhaps even 100% homologous, with the C-terminal portion of the mot-2 gene. Skilled persons will appreciate that a certain degree of error exists in sequencing of nucleic acid molecules, for example, due to slippage when reading the base pairs.

Northern blotting experiments were performed using the same primers as the cloning and RACE PCR experiments utilizing different total RNA and polyA RNA samples from different species (bovine, rat, human, SHSY5Y cells), without success. It was suggested that the novel spliced variant CRP40 may be expressed in low amounts and the Northern was repeated with increased concentrations of poly A RNA and confirmation of two discrete bands were elucidated in bovine striatal tissue, human striatal tissue and SH-SY5Y cells (see FIG. 7). The bands were normalized against the beta-actin transcript and measured following gel electrophoresis. The Northern blot demonstrated 2 discrete bands at approximately 2.8 kb and 1.9 kb, corresponding to the 66 kDa mortalin protein and Human CRP40 (40 kDa) protein, respectively.

Additional functional studies were conducted at a transcriptional level with the neuroblastoma SHSY5Y cells, due to its extensive characterization in CNS function. The DA-D2L receptor was transfected in the SHSY5Y by lipofection. The typical antipsychotic, HAL, was added to the cell culture and the RNA was extracted from these cells along with SH-SY5Y control cells. Real-Time PCR using Human CRP40 primers revealed this novel alternative spliced variant of mortalin is differentially up-regulated in the HAL-treated cells versus control cells, by absolute quantitation. Furthermore, relative quantitation and normalization was used with the housekeeping gene, human cyclophyllin, which showed no significant change between the treated and un-treated cells.

Localization studies were also conducted using immunohistochemistry on postmortem brain samples of the Nucleus Accumbens (NA) from the Stanley Foundation Consortium (SFNC). The results demonstrated that human CRP40 antibody was localized in the perinuclear region of neurons within the NA region in normal controls. Furthermore, similar staining was seen in schizophrenia specimen slides that were drug naive. However, immunostaining in HAL-treated schizophrenia postmortem samples showed that the human CRP40 antibody was clearly seen within the nuclear region.

Real-Time PCR was performed on 105 Postmortem Brain RNA brain samples of the prefrontal cortex (PFC) region, that were generously donated from SFNC in a coded fashion, and on 50 ng DNase-treated RNA using the QIAGEN one-step method in a double paradigm approach. This study showed that ANOVA examination indicated age, sex and PMI had no significant effects on the PFC Human CRP40 expression among the SFNC. However, a significant decrease in Human CRP40 mRNA copy numbers was seen in bipolar patients (n=35), relative to control specimens (n=35). Furthermore, dividing the groups according to amounts of lifetime antipsychotic treatment, showed that a significant decrease in human CRP40 mRNA copy numbers was seen between control specimens and specimens that had a history of consuming the lowest doses of neuroleptics (0-50K). In addition, an increased trend in human CRP40 mRNA expression was seen in patients that consumed the largest lifetime dose of antipsychotics (>400K) versus specimens with the lowest antipsychotic use (0-50K), showing a human CRP40 mRNA normalizing effect with larger antispsychotic use. The above results demonstrate that human CRP40 mRNA expression behaves dysfunctionally in both schizophrenic and bipolar patients within the PFC brain region and this novel protein is differentially modulated by DA-activity. Genetic mapping studies have shown that mot-2 and human CRP40 are on chromosome 5 band q31, which has been shown to be a putative susceptible schizophrenia and bipolar gene locus.

Human CRP40 primers were used with cDNA made from both lymphocytes and platelets, and RT-PCR was performed. The experiment demonstrated distinct bands in both lymphocytes and platelets and sequencing revealed the exact human CRP40 sequence. This finding is important for the use of CRP40 as a biomarker since access to neuronal tissue to study the pathophysiological changes in psychiatric disorders is not possible.

In summary, the cloning, characterization, and localization of human CRP40 protein have demonstrated that this novel protein has catecholamine-regulated functions. Human CRP40 is an alternative spliced variant from the mot-2 gene and has been shown to be down-regulated in neurological disease states.

Example 2

Utility of CRP40 as Biomarker in Neurological Diseases

The present study was undertaken to examine human CRP40 expression in healthy control, schizophrenic and bipolar postmortem brain specimens. A similar study was conducted using primers directed to mortalin-2 and the results were similar.

Methods and Materials

Post-Mortem RNA PFC Sample

Post-mortem DNase-treated RNA specimens of the prefrontal cortex were provided by the Stanley Foundation Neuropathology Consortium. Microscopic examination was performed on all samples by 2 independent neuropathologists trained at the Stanley Foundation in order to provide consistent results. Extensive records of patients were available and were reviewed by two psychiatrists. Diagnoses were established using DSM-IV (Diagnostic and Statistical Manual of Mental Disorders, 4th Edition) criteria (demographics shown in Table 1) as follows. The control patients were confirmed to be free of psychiatric illness and free of substance abuse, and were assessed by the same method.

TABLE 1

Overview of Stanley Foundation Patient Profile

| Characteristics | Bipolar (n = 35) | | Normal (n = 35) | | Schizophrenia (n = 35) | |
|---|---|---|---|---|---|---|
| | Male | Female | Male | Female | Male | Female |
| Sex | 17 | 18 | 26 | 9 | 26 | 9 |
| Age (mean ± S.D., years) | 44 ± 11.7 (range 19-64) | 48.5 ± 9.29 (range 26-63) | 47 ± 7.82 (range 31-60) | 39 ± 5.10 (range 33-49) | 42.5 ± 8.2 (range 19-53) | 47 ± 8.54 (range 32-59) |
| Race | | | | | | |
| white | 15 | 18 | 26 | 9 | 25 | 9 |
| native america | 1 | 0 | 0 | 0 | 0 | 0 |
| black | 1 | 0 | 0 | 0 | 0 | 0 |
| hispanic | 0 | 0 | 0 | 0 | 1 | 0 |
| Lifetime Antipsychotics (mean ± S.D., h) | 1600 ± 32336.2 (range 0-130000) | 3500 ± 8881.3 (range 0-30000) | 0 (range 0-0) | 0 (range 0-0) | 65000 ± 91937.9 (range 50-350000) | 20000 ± 126622.6 (range 600-400000) |
| PMI (mean ± S.D., h) | 32 ± 19.9 (range 12-84) | 37.5 ± 17.2 (range 17-77) | 27 ± 12.1 (range 9-52) | 29 ± 14.7 (range 10-58) | 29.5 ± 17.0 (range 9-80) | 35 ± 11.0 (range 13-52) |

Abbreviations: PMI Postmortem interval

Data regarding cause of death, substance abuse history, antipsychotic intake data and other medication intake at time of death were also provided (Tables 2-5). Matched set RNA brain specimens from 105 patients were obtained, 35 being diagnosed with schizophrenia, 35 being diagnosed with familial bipolar disorder, and 35 being normal controls, and immediately stored under dry ice. Each sample was matched for patient age, gender, mRNA quality and brain pH.

TABLE 2

Subject Profile for Normal Control Subjects From Stanley Foundation

| Age (years/sex) | PMI (h) | CNS medications at time of death |
|---|---|---|
| 31/M | 11 | N/A |
| 32/M | 13 | N/A |
| 34/M | 22 | N/A |
| 35/M | 52 | N/A |
| 35/M | 24 | N/A |
| 37/M | 13 | N/A |
| 40/M | 38 | N/A |
| 42/M | 37 | N/A |
| 45/M | 29 | N/A |
| 45/M | 18 | N/A |
| 46/M | 31 | N/A |
| 47/M | 21 | N/A |
| 47/M | 11 | N/A |
| 47/M | 36 | N/A |
| 48/M | 31 | N/A |
| 48/M | 24 | N/A |
| 49/M | 46 | N/A |
| 49/M | 23 | N/A |
| 50/M | 49 | N/A |
| 51/M | 31 | N/A |
| 51/M | 22 | N/A |
| 53/M | 9 | N/A |
| 53/M | 28 | N/A |
| 55/M | 31 | N/A |
| 57/M | 26 | N/A |
| 60/M | 47 | N/A |
| 33/F | 29 | N/A |
| 34/F | 24 | N/A |
| 38/F | 33 | N/A |
| 38/F | 28 | N/A |
| 39/F | 58 | N/A |
| 41/F | 50 | N/A |
| 44/F | 28 | N/A |
| 44/F | 10 | N/A |
| 49/F | 45 | N/A |

Abbreviations: M, male; F, female

TABLE 3

Subject Profile for Bipolar Subjects From Stanley Foundation

| Age (years/sex) | PMI (h) | CNS medications at time of death |
|---|---|---|
| 19/M | 12 | Quetiapine, Topiramate |
| 29/M | 48 | Risperidone, Lithium |
| 29/M | 60 | None |
| 35/M | 35 | Haloperidol, Lithium |
| 35/M | 22 | None |
| 41/M | 39 | None |
| 41/M | 70 | Lithium, Valproate |
| 42/M | 32 | None |
| 44/M | 19 | Valproate, Thioridazine, Risperidone, Lithium, Valproate, Paroxetine |
| 45/M | 28 | Benztropine |
| 45/M | 35 | Thioridazine, Olanzapine, Gabapentin |
| 48/M | 23 | Lithium, Fluoxetine |
| 51/M | 23 | Lithium, Carbamazepine & Valproate |
| 54/M | 44 | Valproate, Paroxetine |
| 56/M | 23 | Olanzapine, Carbamazepine, Fluoxetine, Doxepin |
| 59/M | 84 | Valproate, Gabapentin, Trazodone, Zolpidem |
| 64/M | 16 | Clozapine, Valproate |
| 29/F | 62 | Trazodone |
| 33/F | 24 | Risperidone, Lithium, Fluoxetine |
| 35/F | 17 | Olanzapine, Amitriptyline |
| 41/F | 28 | Risperidone, Valproate, Trazodone |
| 42/F | 49 | Risperidone, Trazodone |
| 43/F | 39 | Quetiapine, Carbamazepine, Gabapentin, Venlafaxine |
| 43/F | 57 | Quetiapine, Carbamazepine, Fluoxetine, Venlafaxine |

TABLE 3-continued

Subject Profile for Bipolar Subjects From Stanley Foundation

| Age (years/sex) | PMI (h) | CNS medications at time of death |
|---|---|---|
| 44/F | 37 | Quetiapine, Olanzapine, Valproate, Venlafaxine |
| 48/F | 18 | Fluoxetine & Trazodone, Doxepin |
| 49/F | 19 | Perphenazine, Lithium |
| 49/F | 39 | Amitriptyline, Venlafaxine |
| 50/F | 62 | Amitriptyline |
| 51/F | 77 | Risperidone, Valproate, Paroxetine |
| 55/F | 41 | Thiothixene |
| 56/F | 26 | Valproate, Gabapentin, Trazodone, Sertraline |
| 58/F | 35 | Haloperidol, Lithium |
| 59/F | 53 | Valproate, Paroxetine, Trazodone |
| 63/F | 32 | Mirtazapine |

Abbreviations: M, male; F, female

TABLE 4

Subject Profile for Patients With Schizophrenia from The Stanley Foundation

| Age (years/sex) | PMI (h) | CNS medications at time of death |
|---|---|---|
| 19/M | 28 | Thioridazine, Olanzapine, Valproate |
| 24/M | 15 | Olanzapine, Valproate |
| 31/M | 33 | Clozapine, Benztropine |
| 33/M | 29 | Haloperidol, Lithium |
| 35/M | 47 | Fluphenazine, Trihexyphenidyl |
| 37/M | 30 | Thioridazine, Thiothixene, Fluoxetine |
| 38/M | 35 | Quetiapine, Haloperidol, Gabapentin, Trazodone |
| 39/M | 80 | Fluphenazine, Benztropine |
| 39/M | 26 | Ziprasidone, Risperidone, Olanzapine, Haloperidol |
| 40/M | 34 | Thiothixene, Clozapine, Valproate, Benztropine |
| 41/M | 54 | Risperidone, Quetiapine, Lithium, Procyclidine |
| 42/M | 26 | Olanzapine, Paroxetine, Buspirone, Clonazepam |
| 42/M | 19 | Fluphenazine |
| 43/M | 26 | Fluphenazine, Valproate, Benztropine |
| 43/M | 18 | Haloperidol, Benztropine |
| 43/M | 65 | Haloperidol |
| 44/M | 9 | Haloperidol |
| 44/M | 32 | Risperidone, Fluvoxamine |
| 45/M | 35 | None |
| 46/M | 30 | Haloperidol, Risperidone, Carbamazepine |
| 47/M | 13 | Haloperidol, Olanzapine, Valproate |
| 50/M | 9 | Thiothixene |
| 51/M | 43 | Fluphenazine |
| 52/M | 10 | Haloperidol, Benztropine, Diphenhydramine |
| 52/M | 16 | Thiothixene, Fluoxetine, Benztropine |
| 53/M | 38 | Risperidone |
| 32/F | 36 | Risperidone |
| 36/F | 27 | Risperidone, Paroxetine, Trihexyphenidyl |
| 44/F | 26 | Thiothixene |
| 45/F | 52 | None |
| 47/F | 30 | Quetiapine, Valproate, Mirtazapine, Buproprion, Amitriptyline |
| 47/F | 35 | Risperidone, Haloperidol |
| 53/F | 13 | Haloperidol, Lithium |
| 54/F | 42 | Haloperidol, Chlorpromazine, Benztropine |
| 59/F | 38 | Risperidone, Trazodone |

Abbreviations: M, male; F, female

TABLE 5

Categorical Summary of Data used in Statistical Analysis

| Age (years) | Sex | Race | PMI (h) | Disease | CNS medications at time of death (Schizophrenic subjects only) |
|---|---|---|---|---|---|
| 19-28 | Male | White | 9-18 | Normal Control | Psychotic |
| 29-38 | Female | Black | 19-38 | Bipolar | Antipsychotic |

TABLE 5-continued

Categorical Summary of Data used in Statistical Analysis

| Age (years) | Sex | Race | PMI (h) | Disease | CNS medications at time of death (Schizophrenic subjects only) |
|---|---|---|---|---|---|
| 39-48 | | Hispanic | 39-48 | Schizophrenia | |
| 49-58 | | Asian | 49-58 | | |
| 59-68 | | Native American | 59-68 | | |
| | | Mixed Race | 69-78 | | |
| | | | 79-88 | | |

One-Step Real-Time PCR Protocol with Human Post-Mortem Brain RNA Samples in the PFC Region:

The RNA samples consisted of 10 µg DNase-treated RNA, and the concentration and purity (260/280) of each sample was also provided. Real-Time RT-PCR was performed in triplicate for each sample using 50 ng RNA in an MX-3000P Real-Time PCR Machine (Stratagene, U.S.A.). The following Human CRP40 primers were used for all Real-Time PCR experiments: 5'-TTGGCCGGCGATGTCACGGATGTG-5' (Forward, sense primer) (SEQ ID NO: 5) and 5'-ACA-CACTTTAATTTCCACTTGCGT-3' (Reverse, antisense primer) (SEQ ID NO: 6). Previous studies using these primers with human RNA samples demonstrated no primer-dimers, and the transcripts showed optimal Real-Time RT-PCR efficiencies. An absolute standard curve was run along with sample using purified DNA fragment (Sample #1 from The Stanley Foundation) in the range of 1pg-10 pg, and initial template copy numbers were calculated. MX-3000P Real-Time RT-PCR conditions were optimized to ensure that amplifications were in the exponential phase and that efficiencies remained constant during the course of the Real-Time RT-PCR reaction. This experiment was conducted using the QIAGEN One-step RT-PCR method, which contained the QuantiTect SYBR Green with the QuantiTect RT-mix in one tube. Advantages of the One-step method, versus the Two-step method are as follows: 1) fewer pipetting steps minimizing error and contamination; 2) improved sensitivity and specificity at higher temperatures to eliminate problems with secondary RNA structures; 3) and minimal time requirements. All samples were performed in triplicate and a NRT and NTC were also run as controls. The experiment was repeated with the same samples in duplicate using Human Cyclophyllin, a house-keeping gene, to normalize the samples in relative quantitation. The components used in the Real-Time RT-PCR were as follows: 2× SYBRgreen, 10 µl; Forward primer (300 nM), P2, 1.2 µl (5 µM); Reverse primer, (300 nM), P4, 1.2 µl (5 µM); Reverse Transcriptase Mix, 0.2 µl; DEPC H2O, 6.4 µl; Coded Stanley RNA, 1 µl (50 ng). The Real-Time PCR conditions were as follows: 5O° C. 30 sec (1 cycle); 95° C. 15 min (1 cycle); 95° C. 15 sec (40 cycles); 60° C. 30 sec (40 cycles); 72° C. 40 sec (40 cycles).

Statistical Analyses

GraphPad Prism, SPSS and miniTab softwares were used for statistical analyses. Pearson product moment correlation coefficients were determined for all pairs of the measured variables (i.e. mRNA copy numbers, age, sex, post mortem interval (PMI), disease and drug type) and two-tailed tests of the correlations were performed to measure degrees of linear relationships. Statistical analysis was carried out on copy numbers of RNA molecules with respect to the other variables (see Table 1-5) using analysis of variance (ANOVA) methods followed by Tukey's post hoc comparison test.

Figure 14:
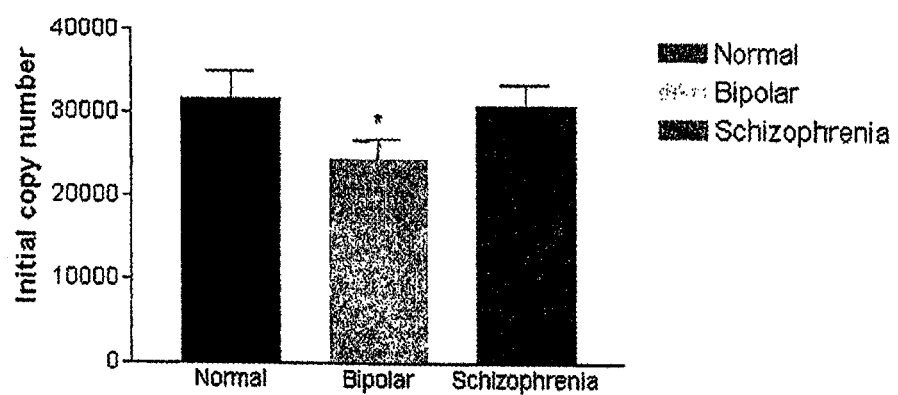
FIG. 14 graphically illustrates RNA expression of CRP40 in human post-mortem RNA of normal individuals, individuals with bipolar disease and individuals with schizophrenia.

Results a) Age, Sex and Post-Mortem Interval Have No Effect on Human CRP40 Expression No significant correlation was found between any pairs of the variables. Thus, ANOVA procedures described in materials section were performed. There were no significant differences in Human CRP40 expression in the PFC with respect to age [F=O142 df(I,34), p>0.05], sex [F=1.56 df(I,34), p>0.05], or post-mortem interval [F=0.3 df(2,34)=, p>0.05] between, control, schizophrenic, and bipolar subjects.

b) Medial Prefrontal Cortex Human CRP40 Expression is Specifically Reduced in Bipolar Patients ANOVA analysis showed significant differences in Human CRP40 expression in the PFC with respect to bipolar disorder [F=8.89, df (2, 104), p<0.01] (see FIG. 14). Post hoc analysis revealed a significant reduction in PFC Human CRP40 expression in bipolar specimens of approximately 31% relative to normal control specimens (n=35).

c) Prefrontal Cortex Human CRP40 Expression is Increased According to the Quantities of Life-Time Antispychotics Administered in Schizophrenic and Bipolar Patients.

ANO VA analysis showed a significant difference was detected in human CRP40 values (F 6.062, df (3, 104), P=0.008) with respect to lifetime cumulative drug-intake dose. Therefore, post-hoc analysis was performed with a Tukey's test. Post-hoc analysis showed a significant difference between the control and the lowest lifetime cumulative antipsychotic drug-intake dose (P<0.001). Furthermore, a definite trend was also found between the lowest treated group and the highest-treated antipsychotic group (>150K), displaying an increased normalizing effect of human CRP40 expression with increased antipsychotic use; however, not statistically significant.

Discussion

Post-mortem Brain RNA brain samples of the PFC region were generously donated from the Stanley Foundation Neuropathology Consortium (SFNC) in a coded fashion. Real-Time PCR was performed on 105 PFC RNA samples using the QIAGEN one-step method and 50 ng DNase-treated RNA. The present study showed that ANOVA examination indicated age, sex and PMI had no significant effects on the PFC Human CRP40 expression among the SFNC. However, a significant decrease in Human CRP40 mRNA copy numbers was seen in bipolar patients (n=35), relative to control specimens (n=35) (see FIG. 14). Furthermore, dividing the groups according to amounts of lifetime antipsychotic treatment, showed that a significant decrease in human CRP40 mRNA copy numbers were seen between control specimens and specimens that had a history of consuming the lowest doses of neuroleptics (0-50K). In addition, an increased trend in Human CRP40 mRNA expression was seen in patients that consumed the largest lifetime dose of antipsychotics (>150K) versus specimens with the lowest antipsychotic use (0-50K), showing a human CRP40 mRNA normalizing effect with larger antispsychotic use (see FIG. 14). The above results demonstrate that Human CRP40 mRNA expression behaves dysfunctionally in both schizophrenic and bipolar patients within the PFC brain region and this novel protein is differentially modulated by DA-activity.

Figure 15:
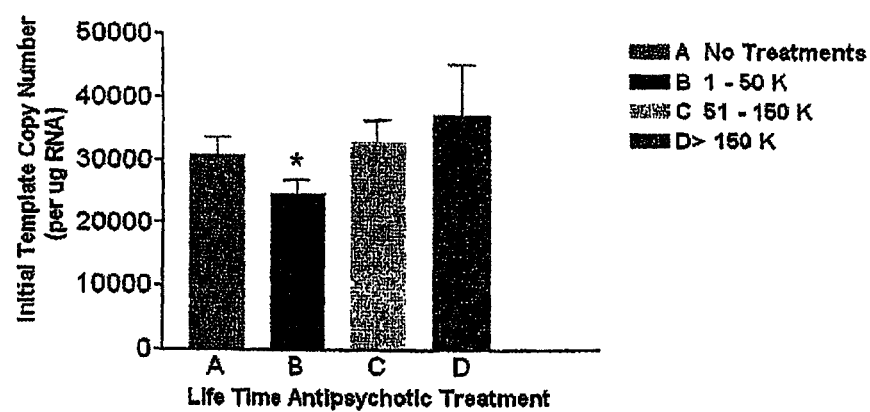
FIG. 15 graphically illustrates RNA expression of CRP40 in human post-mortem RNA of individuals with no drug treatment, and individuals with varying ranges of anti-psychotic drug treatment.

Since both schizophrenia and bipolar disorder are known to have hypo-DA function in the PFC, and the fact that CRP40 is modulated by DA-activity, may explain why there was a significant decrease of Human CRP40 mRNA copy numbers, evidenced by Real-Time PCR in the bipolar specimen samples. Furthermore, the bipolar group consisted of 1 patient out of 35 that was treated with a substantial lifetime amount of neuroleptics, explaining the low CRP40 copy numbers in these DA-depleted PFC brain specimens. In contrast, the entire schizophrenic patient profile had a broad administration of antipsychotic use, from less than 5OK to >400K. The increased antipsychotic use in the schizophrenic specimens are known to cause increased DA release, which may explain the normalizing effect of Human CRP40 mRNA copy numbers in the schizophrenic group (see. FIG. 15).

To further assess the observed decrease in CRP40 expression levels in these patients, the entire patient profile was separated according to ranges of lifetime antipsychotic administration and the mRNA copy numbers were used for statistical analysis. The results showed that patients administered low doses of antipsychotic drugs (0-50 K) displayed a significantly lower initial copy number expression of Human CRP40 than controls (see FIG. 15). These results correlate well with the original hypothesis that human CRP40 expression is directly related to the amount of antipsychotic use and increased DA release. A normalized effect was seen with the increased lifetime antipsychotic treatment.

Example #3

Affect of Reduced CRP40 Expression

This experiment was conducted to determine whether or not reduced CRP40 in the prefrontal cortex is linked to the development of schizophrenia-like behavioural abnormalities or whether reduction in CRP40 in patients with schizophrenia is a consequence of the disease process.

To establish whether reduced expression of CRP40 in the medial prefrontal cortex leads to the development of behavioural abnormalities in a putative animal model, the following experimental approach was used.

Five groups of rats each consisting of 4 subgroups (n=12/subgroup, totaling 240 rats) were implanted with bilateral 26-gauge stainless steel guide cannulae (Plastics One Cat#3280PD-2.0) above the prefrontal cortex (stereotaxic coordinates: 3.0 mm anterior to bregma, 0.7 mm lateral to midline and 2.5 mm below the surface of the skull). ADONS solutions were infused continuously for 3 weeks via S.C. implanted osmotic mini-pumps (Alzet model #2004) connected by separate catheters (PVC60 cannula tubing, Plastics One Cat#C312VT) to respective cannulae. Group A (Subgroups: Ai, A2, A3, A4; n=12/subgroup) received Human CRP40 antisense deoxyoligonucleotides, 5'-tcg ttc ctt ctt tgg ccg gtt ttt t-3' (SEQ ID NO: 4). Group B (Subgroups: Bi, B2, B3, B4; n=12/subgroup) received sense deoxyoligonucleotide, 10 nmol/day via osmotic pump. Group C (Subgroups: Ci, C2, C3, C4; n=12/subgroup) received ADONS 10 nmol/day via osmotic pump. Group D (Subgroups: Di, D2, D3, D4; n=12/subgroup) received missense (random) deoxyoligonucleotides similar to Group B. Group E (Subgroups: Ei, E2, E3, E4; n=12/subgroup) served as a normal control. At the end of the infusion period, all groups of rats were monitored for development of behavioural abnormalities: 1. PPI of acoustic startle response (76). These behavioural abnormalities were recorded on a weekly basis, up to 4 weeks, without challenge with any dopaminergic drug (since schizophrenia patients display abnormalities at baseline as well as in response to pharmacological challenges (6;76;80;81)). One subgroup from each group was sacrificed every week (up to 4 weeks) so that CRP40 mRNA levels could be estimated by Real-Time RT-PCR and protein levels by western blotting. The percent reduction of prefrontal cortex CRP40 levels was correlated with the intensity of behavioural abnormalities displayed by various groups of rats at weekly intervals.

Determination of Prepulse Inhibition:

This technique measures the sensorimotor gating deficit observed in patients with schizophrenia by assessing a reflex startle response to a brief stimulus as a behavioural measure in rats. In this model, a weak sub-threshold acoustic stimulus (prepulse) was presented to a rat before a strong acoustic or tactile stimulus (pulse) and functions to inhibit the startle to the latter one. A disruption of PPI was found in schizophrenic patients and in animals by dopaminomimetics and antagonized by APDs. PPI in all groups was recorded using the SR-Lab Startle Response System (San Diego Instruments) as described by Term et al. in 2003 (64). Briefly, rats were placed in the startle apparatus and allowed to acclimatize for 10 minutes with a background noise [65 dB]. The rats were then presented with a series of 5 startle pulses without any prepulse to control for habituation of the startle response. This series of stimuli was followed by 60 randomized trials consisting of no pulse [0 dB], a startle pulse [110 dB, 40 ms] or three prepulse intensities [70, 75 and 80 dB, 20 ms] presented alone or 100 ms preceding the startle pulse. At the end, another series of five startle pulse-alone trials was presented. The startle response was measured every 1 ms for a 100 ms period from the onset of the startle stimulus. The % PPI was calculated as 100-[(P+S)/S]100. P+S is the mean response amplitude for prepulse trials and S is the mean response amplitude for the startle pulse-trial alone (64).

Figure 16:
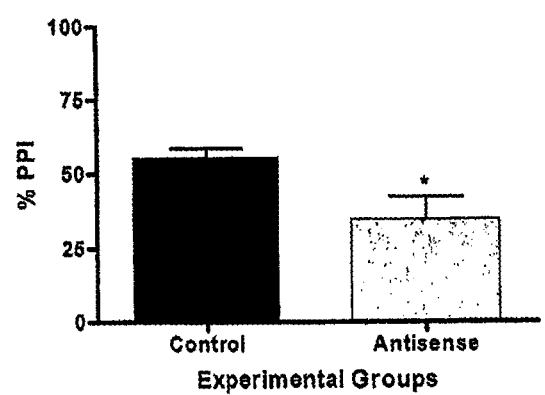
FIG. 16 graphically illustrates prepulse inhibition in CRP40 knock-down animal study.

As shown in FIG. 16, significant pre-pulse inhibition (PPI) resulted from the foregoing CRP40 knock-down study. PPI is a standard test used to identify schizophrenia.

Example #4

Platelet Aggregation by CRP40

CRP40 was also determined to cause aggregation of platelets. The following protocol was followed to study this affect:
1) isolated platelets from whole blood using established methodology;
2) washed platelets (500000/µl) with F agonist;
3) stopped reaction in 1% paraformaldehyde-50 µl Rx mixture+200 µl PF;
4) washed cells with boton (4.5 ml), then centrifuged at 2200 rpm for 15 minutes; resuspended cells in isoton+1 mg/ml BSA 250 µl;
5) Staining-50 µl platelets+20 µl CD62 PE (1/10 dilution)-incubated 30 minutes in dark at room temperature;
6) washed with 4.5 ml isoton and centrifuged 2200 rpm for 15 minutes; and
7) resuspended in 250 µl isoton.

Flow cytometry was then conducted.

The results showed that the addition of 10 µl pure CRP40 fusion protein caused a 80% increase in platelet aggregation relative to control platelets.

This activity of CRP40 as a platelet aggregator renders CRP40 a target in the treatment of cardiovascular disease.

Example #5

Diagnostic Blood Test for Neurological Disease

Isolation of Platelets 2.0 ml of fresh rat blood was collected in eppendorf tubes. The blood was centrifuged at 1000 rpm (190 g) (Beckman TJ-6 bench centrifuge) for 10 min. Platelet rich plasma (PRP) was carefully transferred to a 15 ml conical tube (carefully transferred 0.75% of the supernatant to avoid contamination). The platelets were centrifuged 2750 rpm (1600 g) for 7 min. and the supernatant was decanted. The platelet button was resuspended in 1 ml of PBS (GIBCO) with 1% Na2+EDTA, 0.1% BSA. Platelet suspension was then transferred to a 20 ml Falcon tube and filled completely with PBS buffer (pipette mix) and centrifuged at 2750 rpm (1600 g) for 7 min. The supernatant was decanted and washing repeated one more time.

Isolation of Lymphocytes from Rat Blood 2.0 ml fresh rat blood was obtained, transferred to a sterile 50 ml Falcon tube and 15 ml 1×PBS was added. Next, 5 ml Ficoll Paque sample was added to the mixture through a Pasteur pipette. The sample was centrifuged in a Beckman TJ-6 centrifuge at 1700 rpm for 20 min. Immediately following, the buffy coat was removed and transferred to a new 50 ml Falcon tube. The tube was filled to the 50 ml mark and centrifuged at 1800 rpm for 12 min. Following centrifugation, the aqueous layer was removed. Isopropyl alcohol (0.5 ml) was added to remaining suspension and incubated at room temperature for 10 min. Again, the solution was centrifuged at max. speed for 15 min and the pellet was retained. The pellet was resuspended with 1 ml 75% ethanol and centrifuged at 4° C. for 8 min. The supernatant was then drawn off and the pellet was allowed to dry for 5 min. The dried pellet was resuspended in 30 ml DEPC H2O. RNA was isolated by TRIzol method and reverse transcribed into cDNA. Real-time PCR was performed as previously described.

Preparation of RNA Using Qiagen RNeasy Mini Kit

To the platelet pellet, 300 µl of RLT buffer was added and the mixture was homogenized well by passing the lysate through a 21 gauge needle fitted to an Rnase-free syringe (5 times). The suspension was transferred to a 1.5 ml eppendorf tube. An equal volume of 70% ethanol was added and mixed by pipetting. The full amount was applied to the QIAGEN RNeasy mini-column, placed in a 2 ml collection tube. The tube was closed gently and centrifuged at 10000 rpm (8000 g) for 15 sec. The flow-through was discarded and the same collection tube used again. 700 µl of RWI buffer was then added. The tube was closed gently and centrifuged at 10000 rpm (8000 g) for 15 sec. Flow-through was again discarded. 500 µl of RPE was added onto QIAGEN RNeasy mini-column and centrifuged at 10000 rpm (8000 g) for 15 sec. Flow-through was discarded, another 500 µl of RPE was added on QIAGEN RNeasy mini-column and centrifuged for 2 min at 10000 rpm (8000 g). The QIAGEN RNeasy mini-column was placed over a new collection tube and centrifuged at maximum speed for 1 min to ensure that no ethanol was carried over during elution. To elute, the QIAGEN RNeasy mini-column was transferred to a new 1.5 ml collection tube and 30 µl RNase free H2O was pipetted directly on to the RNeasy silica-gel membrane. The tube was closed gently and centrifuged at 10000 rpm (8000 g) for 1 min. To increase RNA yield, the column with re-eluted with the first eluate. Check OD at 260 and 280. The platelet RNA was reverse transcribed into cDNA, and Realtime PCR was performed as previously described.

Results

Following Real-time PCR using specific human CRP40 primers (as identified in Experiment #2 above), the product was run on a 1% agarose gel, the band was cut out and sent for sequencing to MOBIX at McMaster University. The sequence results for both the platelets and lymphocytes were identical to the brain tissue RNA previously reported.

Example #6

Diagnostic Blood Test for Neurological Disease

The blood test described above was also conducted using human blood. Platelets and lymphocytes were collected in the manner described in Example 5 from 20 ml human blood, and CRP40 DNA quantified as described.

Figure 17:
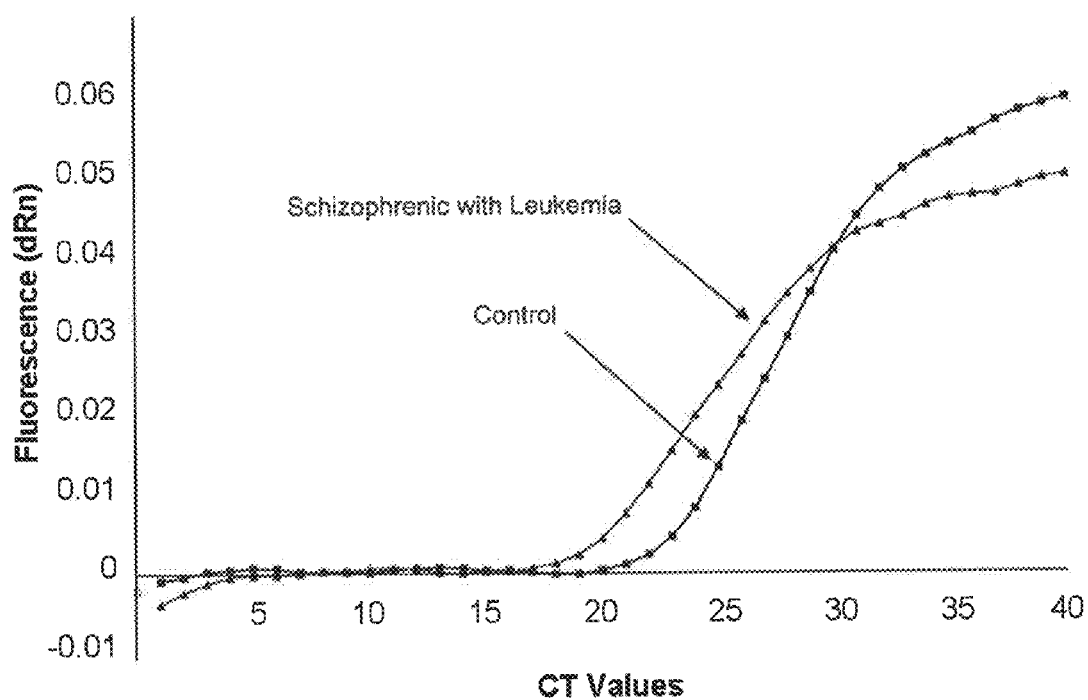
FIG. 17 graphically illustrates the real time PCR significant difference between schizophrenic patients (n=6) and controls (n=4) with respect to CRP40 levels.
Figure 18:
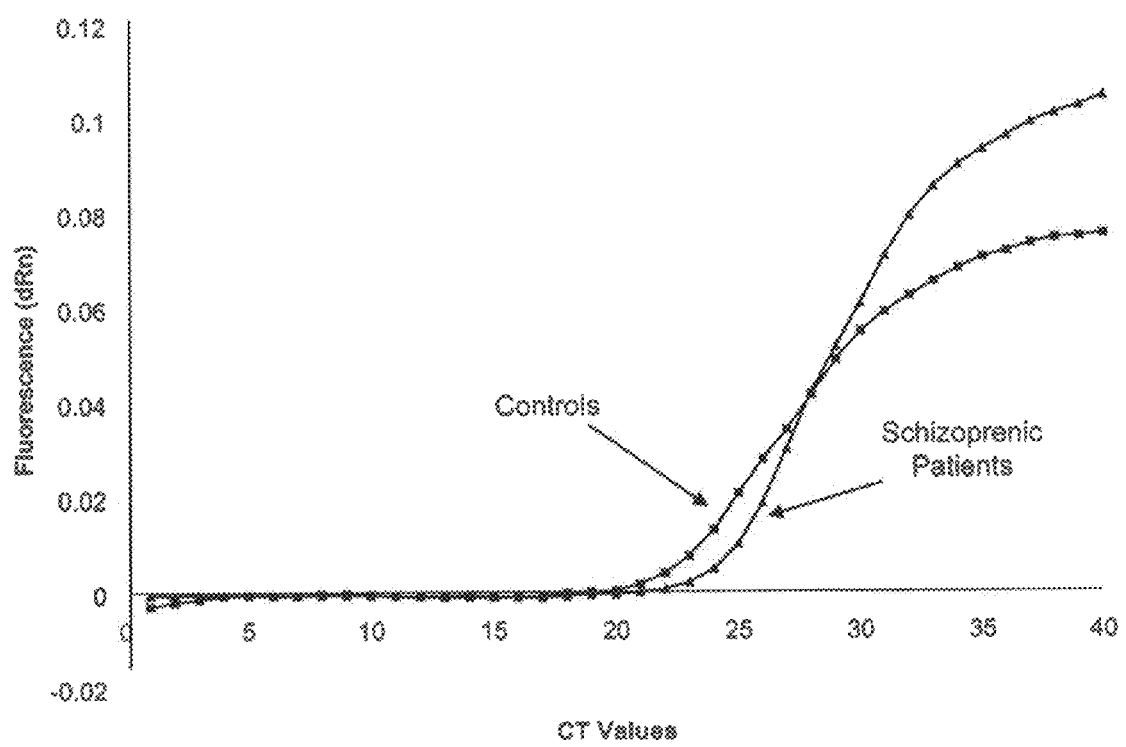
FIG. 18 graphically illustrates the real time PCR significant difference between schizophrenic patients (n=4) and controls (n=2) with respect to CRP40 levels.
Figure 19:
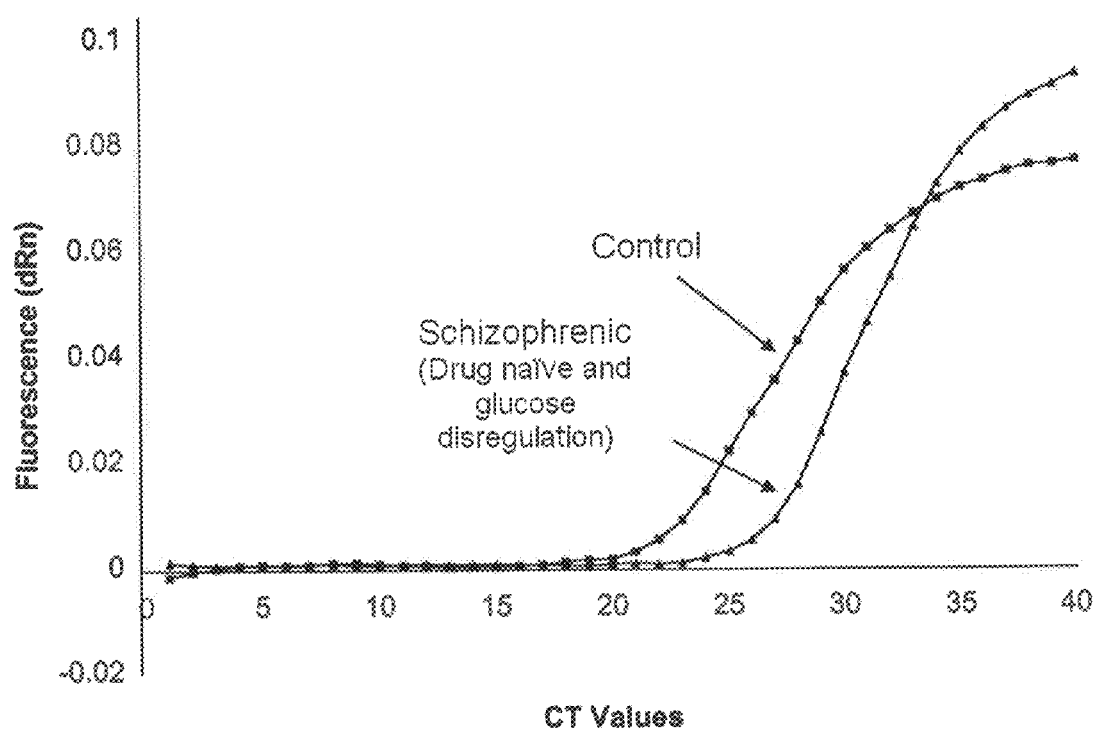
FIG. 19 graphically illustrates the real time PCR significant difference between a drug naïve schizophrenic patient and a control with respect to CRP40 levels.
Figure 20:
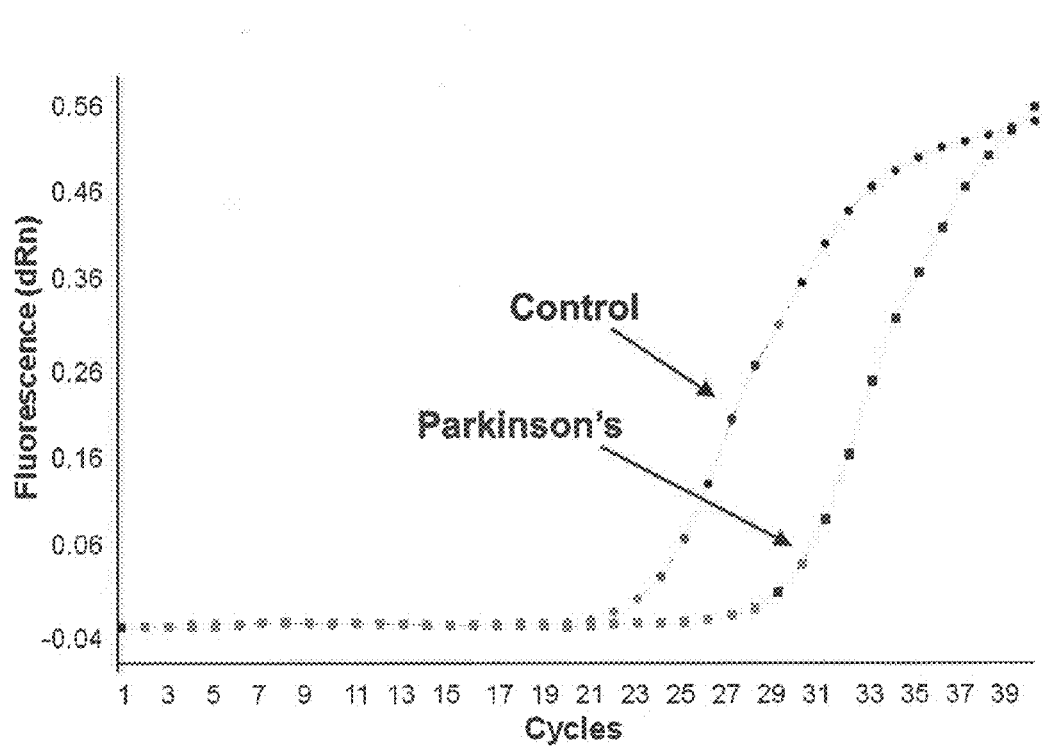
FIG. 20 graphically illustrates the real time PCR significant difference between a Parkinson's patient and a control with respect to CRP40 levels.

The results of the real time PCR CRP40 quantitation are shown in FIGS. 17-19 and each illustrate statistically significant differences between patients with neurological disease and control patients without neurological disease. Specifically, FIG. 17 graphically illustrates the detection of reduced CRP40 levels in schizophrenic patients (n=6) versus non-schizophrenic control patients (n=4). cDNA was obtained from lymphocytes. FIG. 18 graphically illustrates reduced CRP40 levels between schizophrenic patients (n=4) and controls (n=2) using cDNA obtained from platelets. FIG. 19 graphically illustrates reduced CRP40 levels between a drug naive schizophrenic patient with symptoms of glucose disregulation and a control. cDNA was obtained from platelets. FIG. 20 graphically illustrates reduced CRP40 levels between patients (n=3) with Parkinson's and controls (n=3) using cDNA obtained from platelets.

Example #7

Preparation of a CRP40 Therapeutic Composition

Previous reports have shown that nanoparticles via nasal delivery reach numerous regions of the brain (Gao et al. 2006; Zhang et al. 2006). Accordingly, the following protocol is used to formulate CRP40 nanoparticles for nasal spray.

Preparation of Nanoparticles: The mortalin gene (human CRP40 alternative splice variant) is cloned in a mammalian expression plasmid, known to induce stable and strong transgene expression (Gomez-Vargas et al. 2004) driven by a ubiquitous promoter (such as #946;-actin which has been shown to be a stable genetic element driving antigen transcription in vivo (Broome et al. 2006). Chitosan nanoparticles, for use in delivering this construct, are synthesized by complexing high-molecular-weight (about 390,000 Da) chitosan with plasmid DNA to obtain uniform particles. Thus, 0.02% chitosan, pH 5.7, at 55° C. is added to plasmid DNA (50 mg/ml in 50 mM sodium sulfate) during high-speed vortexing. Transmission and scanning electron microscopy are run to test that the particle size does not exceed 150-300 nm in size (Roy et al. 1999). The plasmid is partially protected from DNase degradation in this formulation and its gel migration properties are unchanged by the process of forming complexes.

Example #8

Human Blood Study with Schizophrenic Patients

This study examined the role of catecholamine regulated proteins in schizophrenia. Specifically, the study investigated whether the expression of catecholamine regulated protein 40 (CRP40) was reduced in white blood cells of human subjects with a clinical diagnosis of schizophrenia (e.g. drug naïve subjects) as compared to subjects without schizophrenia, as well as subjects already treated with medication for schizophrenia. The study was double-blinded with respect to subject diagnosis and analysis of CRP40 mRNA expression in white blood cells.

CRP40 expression was measured in white blood cells because it has now been found that CRP40 is expressed in white blood cells at both protein and mRNA levels, indicating an application of CRP40 for blood diagnosis of neurological disorders. The goal of this study was to determine whether human subjects with a clinical diagnosis of schizophrenia (e.g. drug naïve subjects) have reduced levels of CRP40 mRNA in white blood cells, and whether treatment with antipsychotic drugs (e.g. schizophrenia group) affected CRP40 levels.

Treatment Groups

The treatment groups were the following: Group 1 (n=18; 8 males, 10 females, aged 24-74 years old) was the control group without schizophrenia; Group 2 (n=8; 6 males, 2 females, aged 24-70) were the "drug naïve" (e.g. first episode) subjects with schizophrenia; Group 3 (n=42; 32 males, 10 females, aged 17-88) (e.g. schizo group) was a group of subjects receiving antipsychotic drugs (APDs) for schizophrenia. For selection to participate in the study, all of the subjects had to undergo a screening process involving a review of the medical history, psychiatric history, alcohol and drug abuse history along with a structured clinical interview. The diagnosis of schizophrenia was confirmed through the administration of the structural clinical interview (SCID). The subjects were selected from a pool of people (>1000) who attended the outpatient service affiliated with St. Joseph's Health Care, Hamilton, Ontario, Canada.

Materials and Methods 20 to 30 mL of blood was collected from subjects and white blood cells were prepared as per the following methods: 10 mL of whole blood was collected in 1.42 mL of acetate citrate dextrose (ACD) BD vacutainers, mixed with 10 mL of warm phosphate saline buffer (PBS) and layered over 15 mL of Ficoll Paque; the gradient was spun at 400 g for 30 minutes (zero brake), the buffy coat was collected and washed twice with 30 mL of PBS by spinning at 110 g for 10 minutes (zero brake); the pellet was re-suspended in 1 mL PBS in an Eppendorf tube spun at 110 g for 10 minutes; finally, the supernatant was removed and the pellet was stored at −80 degrees Celsius until further analysis.

White blood cell RNA preparation was performed with TRIzol according to the manufacturer's protocol. The RNA pellet was dissolved in 20 μl RNase-free water and RNA platelet purity was determined by absorption at 260 nm and 280 nm using a spectrophotometer.

Relative CRP40 mRNA levels in all samples (controls, drug naïve, typical APD treated and atypical APD treated) were analyzed by Real-Time Polymerase Chain Reaction (RT-PCR). In preliminary experiments using CRP40 specific primers to quantify mRNA levels in the white blood cells, no primer-dimers were detected and transcripts showed optimal Real-Time RT-PCR efficiencies. An absolute standard curve was constructed with an external standard in the range of 1 picogram-10 attogram of cDNA. MX3000P Real-Time RT-PCR conditions were optimized to ensure the amplifications were in the exponential phase and the efficiencies remained constant in the course of the Real-Time RT-PCR. Real-Time RT-PCR was performed in triplicate for each sample using MX 3000P Real-Time RT-PCR (Stratgene). Components of the reaction mixture were 10 ng of RNA, 300 nM each of CRP40 primers (forward primer 5' TTG GCC GGC GAT GTC ACG GAT GTG 3' (SEQ ID NO:5); reverse primer 5' ACA CAC TTT AAT TTC CAC TTG CGT 3' (SEQ ID NO:6)), 0.3 μl Rox (reference dye), 10 μl SYBR Green 2× Mix and water to a final volume of 20 μl. The Real-Time RT-PCR products each showed 100% homology with the CRP40 gene regions. All data was normalized against the human cyclophilin housekeeping gene.

Data collected from all groups was subjected to statistical analysis using Graph Pad Prism 5.0 software. The differences in CRP40 mRNA copy numbers between each patient group (e.g. control, first episode, and schizo) were determined using analysis of variance (ANOVA). All statistical tests were two-tailed using a confidence level of $\alpha=0.05$. The post test used to compare the three sets of data was Tukey's test.

Results

Figure 21:
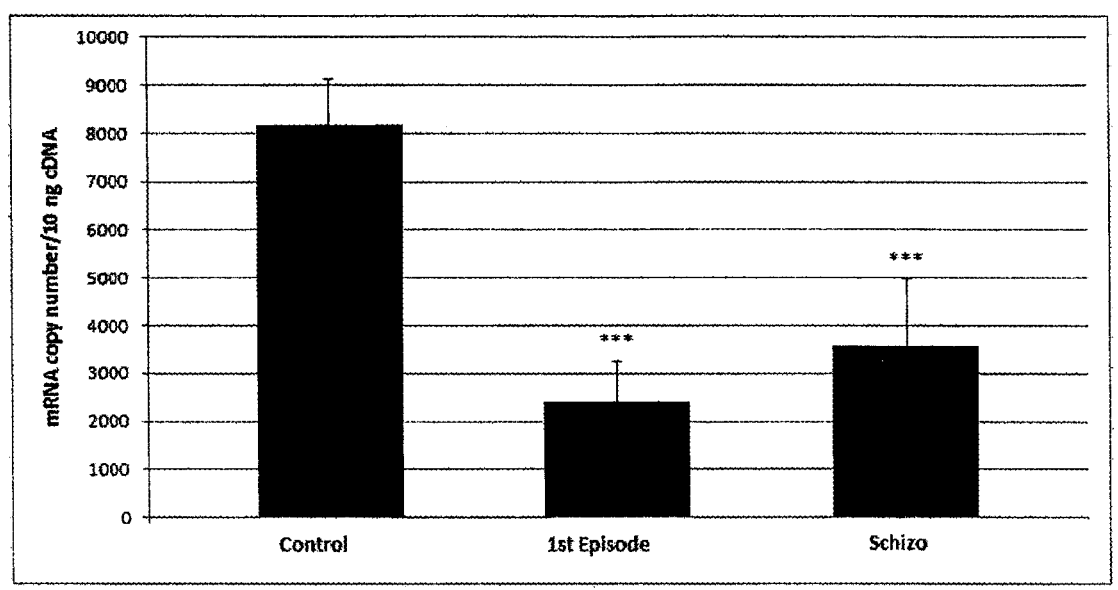
FIG. 21 shows CRP40 mRNA expression in white blood cells of a control group (n=18), a 1st episode drug naïve group (n=8) and subjects with schizophrenia (e.g. schizo group) (n=42) determined by Real-Time PCR.

FIG. 21 shows CRP40 mRNA expression in white blood cells of a control group (n=18), a 1st episode drug naïve group (n=8) and subjects with schizophrenia (e.g. schizo group) (n=42) determined by Real-Time PCR. There are fewer numbers in the drug naïve group as these patients are less prevalent. Following one-way ANOVA analysis, statistically significant differences in CRP40 mRNA copy numbers/10 ng of cDNA were observed between the control and 1st episode group and control group versus schizo group ($p<0.0001$). Thus, CRP40 mRNA was significantly reduced in both schizo groups.

Conclusions

This study examined the expression of CRP40 mRNA levels in white blood cells of subjects with a clinical diagnosis of schizophrenia (e.g. first episode drug naïve subjects) versus normal controls and schizophrenia patients in order to investigate the potential use of CRP40 as a diagnostic tool for schizophrenia ("schizo"). Based on this study, it was determined that CRP40 mRNA copy numbers varied significantly between normal and 1st episode drug naïve schizophrenia patients. As well, it was found that there were statistically significant differences between control CRP40 mRNA levels and schizophrenia patients. The mean CRP40 mRNA levels in the control group were approximately 3 times higher than the mean CRP40 levels in the 1st episode drug naïve group. There was no overlap in the standard error bars. The results indicated a tendency of CRP40 mRNA levels to increase slightly following treatment with ADPs as in the schizophrenia group. However, the differences in copy numbers of CRP40 mRNA between the 1st episode drug naïve group and schizo group were not found to be statistically significant in the samples tested.

Example 9

Human Blood Study with Parkinson's Disease Platelets

This double-blind study was performed in order to investigate the potential use of CRP40 as a biomarker for diagnosis of Parkinson's disease. The levels of CRP40 mRNA were measured using Real-Time Polymerase Chain Reaction (RT-PCR) in blood platelets of control (e.g. normal) subjects versus Parkinson's disease patients. Our laboratory established that CRP40 mRNA and protein is expressed in platelets. Platelets are developmentally related to the brain, making them an interesting target for assessment of neurological disorders such as Parkinson's disease.

Treatment Groups

Subjects with classical symptoms of Parkinson's disease and healthy controls were recruited from McMaster University Medical Centre—Neurology Clinic, Canada. 14 normal subjects (aged 24-58) and 15 Parkinson's disease subjects (aged 44-88) participated in the study. Blood was collected from Aspirin-free subjects. The study was double blinded with respect to subject's diagnosis and analysis of blood platelets for CRP40 mRNA expression.

Materials and Methods 20-30 mL of blood was collected from each subject and the platelets were prepared as follows: platelets were collected from 20-30 mL of blood using Acid Citrate Dextrose anticoagulant cocktail. The blood was centrifuged at 980 g for 2 minutes in an Eppendorf centrifuge 5810R, at 21° C. without brake. Two thirds of the top layer (platelet-rich plasma region) were removed and transferred to a 15 mL polypropylene Falcon tube. The collected platelet-rich plasma was centrifuged at 1200 g for 7 minutes and the supernatant was removed. The pellet was washed twice in 7 mL of Phosphate Buffer Saline-EDTA-BSA (PEB) wash solution and centrifuged again at 1200 g for 7 min. The existing pellet was resuspended in 1 mL of PEB wash solution. The final platelet pellet was then centrifuged at 1200 g for 7 min in an Eppendorf tube and the supernatant was removed and the pellet was stored at −80 degrees Celsius until further analysis. Platelet RNA preparation was performed using TRIzol according to the manufacturer's protocol. The RNA pellet was dissolved in 20 µl RNase-free water and RNA platelet purity was determined by measuring absorption at 260 nm and 280 nm using a spectrophotometer.

RT-PCR was used to analyze CRP40 mRNA levels in all samples. RT-PCR was performed in triplicate for each sample using MX3000P Real-Time PCR (Strategene). In preliminary experiments using CRP40 specific primers to quantify mRNA levels in the platelets, no primer-dimers were detected and transcripts showed optimal Real-Time RT-PCR efficiencies. An absolute standard curve was constructed with an external standard in the range of 1 picogram-10 attogram of cDNA. MX3000P Real-Time RT-PCR conditions were optimized to ensure the amplifications were in the exponential phase and the efficiencies remained constant in the course of the Real-Time RT-PCR. Components of the reaction mixture were 10 ng of cDNA, 300 nM each of CRP40 primers (forward primer 5' TTG GCC GGC GAT GTC ACG GAT GTG 3' (SEQ ID NO:5); reverse primer 5' ACA CAC TTT AAT TTC CAC TTG CGT 3' (SEQ ID NO:6)), 0.3 µl Rox (reference dye), 10 µl SYBR Green 2× Mix and nuclease-free water to a final volume of 20 ul. Representative RT-PCR products each showed 100% homology with the CRP40 gene regions. Data was normalized against a human housekeeping gene, cyclophillin. Statistical analysis of the data was performed utilizing Graph Pad Prism 5.0 software. A two-tailed unpaired t-test with a confidence interval of 95% was utilized to analyze the data.

Results

Figure 22:
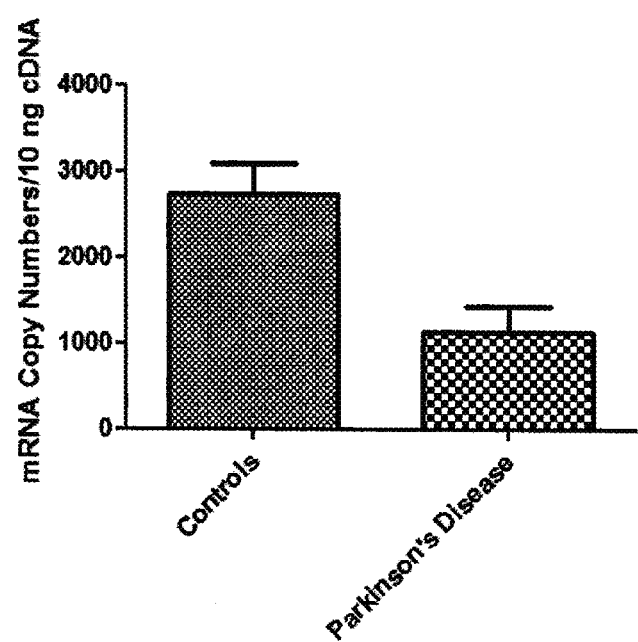
FIG. 22 shows CRP40 mRNA expression in platelets of control group (n=14) versus subjects with Parkinson's disease (n=15) determined by Real-Time PCR.

FIG. 22 shows CRP40 mRNA expression in platelets of control group (n=14) versus subjects with Parkinson's disease (n=15) determined by Real-Time PCR. Following statistical analysis (two-tailed unpaired t-test with confidence interval of 95%), it was determined that there were statistically significant decreases in CRP40 mRNA copy numbers/10 ng of cDNA in the Parkinson's disease group as compared to the normal control group (p=0.0022). The CRP40 mRNA levels were significantly reduced in Parkinson's disease subjects with an average of 1128 mRNA copy numbers of CRP40 per 10 ng cDNA. Normal healthy controls displayed 2737 CRP40 mRNA copy numbers per 10 ng cDNA on average. Thus, a decrease of greater than 50% was seen in the diseased group compared to control.

Conclusions

This study examined the expression of CRP40 mRNA levels in platelets of subjects with Parkinson's disease versus normal controls in order to investigate the potential use of CRP40 as a biomarker for Parkinson's disease. Based on this study, it was determined that platelet CRP40 mRNA copy numbers were significantly reduced in Parkinson's disease subjects when compared to controls. This study demonstrated that there was a strong correlation between Parkinson's disease and decreased CRP40 levels compared to normal.

Example 10

Lewy Body Dementia, Multisystem Atrophy and Newly Diagnosed Parkinson's Study Patients—Using Platelets This double-blind research study was performed in order to investigate the levels of CRP40 in diseases affecting the dopaminergic system, including Parkinson's disease (PD), Lewy Body Dementia (LBD), and Multisystem Atrophy (MSA). LBD and MSA are generally considered to fall within the milieu of PD, although they each have distinct profiles. All three are related to a protein called alpha-synuclein which aggregates to form insoluble fibrils known as Lewy bodies. In this study, CRP40 mRNA levels were measured in blood platelets using Real-Time Polymerase Chain Reaction (RT-PCR). It was established that CRP40 is expressed in platelets at both mRNA and protein levels. Since platelets are developmentally closely related to the brain, the blood component was used as a model to investigate neurological disorders.

Treatment Groups

Subjects were recruited from Toronto Western Hospital. The control subjects (n=8) were normal, healthy subjects. The Parkinson's disease subjects (n=3, all males, aged 40-64 years) were newly diagnosed patients with classical symptoms of Parkinson's disease. Lewy Body Dementia patients (n=4, 2 females and 2 males, aged 80-85 years) and Multisystem Atrophy (n=3, all females aged 59-64) were also included in the study. The study was double blinded with respect to subject's diagnosis and analysis of blood platelets for CRP40 mRNA expression.

Materials and Methods 20-30 mL of blood was collected from each subject and the platelets were prepared as follows: platelets were collected from 20-30 mL of blood using Acid Citrate Dextrose anticoagulant cocktail. The blood was centrifuged at 980 g for 2 minutes in an Eppendorf centrifuge 5810R, at 21° C. without brake. Two thirds of the top layer (platelet-rich plasma region) were removed and transferred to a 15 mL polypropylene Falcon tube. The collected platelet-rich plasma was centrifuged at 1200 g for 7 minutes and the supernatant was removed. The pellet was washed twice in 7 mL of Phosphate Buffer Saline-EDTA-BSA (PEB) wash solution and centrifuged again at 1200 g for 7 min. The existing pellet was resuspended in 1 mL of PEB wash solution. The final platelet pellet was then centrifuged at 1200 g for 7 min in an Eppendorf tube and the supernatant was removed and the pellet was stored at −80 degrees Celsius until further analysis. Platelet RNA preparation was performed using TRIzol according to the manufacturer's protocol. The RNA pellet was dissolved in 20 µl RNase-free water and RNA platelet purity was determined by measuring absorption at 260 nm and 280 nm using a spectrophotometer.

RT-PCR was used to analyze CRP40 mRNA levels in all samples. RT-PCR was performed in triplicate for each sample using MX3000P Real-Time PCR (Strategene). In preliminary experiments using CRP40 specific primers to quantify mRNA levels in the platelets, no primer-dimers were detected and transcripts showed optimal Real-Time RT-PCR efficiencies. An absolute standard curve was constructed with an external standard in the range of 1 picogram-10 attogram of cDNA. MX3000P Real-Time RT-PCR conditions were optimized to ensure the amplifications were in the exponential phase and the efficiencies remained constant in the course of the Real-Time RT-PCR. Components of the reaction mixture were 10 ng of cDNA, 300 nM each of CRP40 primers (forward primer 5' TTG GCC GGC GAT GTC ACG GAT GTG 3'

(SEQ ID NO:5); reverse primer 5' ACA CAC TTT AAT TTC CAC TTG CGT 3' (SEQ ID NO:6)), 0.3 µl Rox (reference dye), 10 µl SYBR Green 2× Mix and nuclease-free water to a final volume of 20 ul. Representative RT-PCR products each showed 100% homology with the CRP40 gene regions. Data was normalized against a human housekeeping gene, cyclophilin. Statistical analysis of the data was performed utilizing Graph Pad Prism 5.0 software. A one-way ANOVA with a confidence interval of 95% was utilized to analyze the data; the post test used was Tukey's test.

Results

Figure 23:
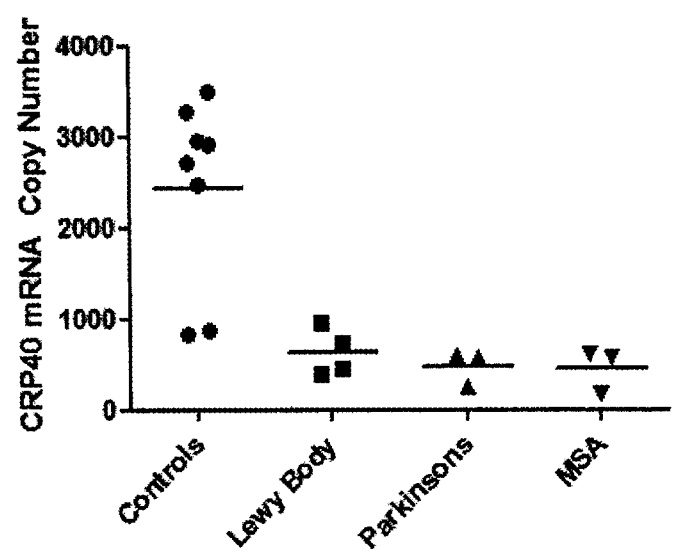
FIG. 23 shows CRP40 mRNA expression in platelets (e.g. per 10 ng of cDNA) of control group (n=8) versus subjects with Lewy Body Dementia (n=4), Parkinson's disease (n=3), and Multisystem Atrophy (MSA) (n=3) determined by Real-Time PCR.

FIG. 23 shows CRP40 mRNA expression in platelets (e.g. per 10 ng of cDNA) of control group (n=8) versus subjects with Lewy Body Dementia (n=4), Parkinson's disease (n=3), and Multisystem Atrophy (MSA) determined by Real-Time PCR. The mean values for CRP40 mRNA copy numbers shown by horizontal bars in graph are the following: Control (2440), Lewy Body Dementia (635), Parkinson's Disease (477), and MSA (449). The results indicated that there were statistically significant differences in platelet CRP40 mRNA copy numbers between controls versus Lewy Body Dementia group, controls versus Parkinson's Disease group, and controls versus Multisystem Atrophy group (FIG. 23). The CRP40 mRNA levels in platelets were significantly reduced in the disease states. The mean CRP40 mRNA copy numbers per 10 ng of cDNA found were the following: Control (2440), Lewy Body Dementia (635), Parkinson's Disease (477), and MSA (449) (FIG. 23).

Conclusions

This study examined the expression of CRP40 mRNA levels in platelets of subjects with dopaminergically driven diseases including Lewy Body Dementia, Parkinson's disease, and Multisystem Atrophy versus healthy, normal controls. The goal of this study was to investigate the link between CRP40 levels and diseases affecting the dopaminergic system.

The results of this study demonstrated close relation in CRP40 mRNA levels in Lewy Body Dementia, Parkinson's disease, and Multisystem Atrophy, which are significantly different from CRP40 levels in normal, healthy control subjects. The findings are useful for establishing a reliable diagnostic test using CRP40 to identify dopaminergically driven neurological diseases.

Example 11

Measuring CRP40 Levels in the Neonatal Ventral Hippocampal (NVH)-Lesioned Animal Model of Schizophrenia-Western Blot Results The objective of this study was to further investigate the role of CRP40 in schizophrenia. A neurodevelopmental animal model for schizophrenia, known as the neonatal ventral hippocampal (NVH)-lesioned model, was used. The bilateral NVH-lesioned rat has been extensively studied as a preclinical animal model of schizophrenia and the NVH-lesioned rats and sham-lesioned controls used in this study were generously donated by Sanjeev Bhardwaj (McGill University). The ventral hippocampus was chosen since this region corresponds to the anterior hippocampal circuitry in human patients with schizophrenia. The NVH-lesioned rats were created by inducing neonatal hippocampus damage by ibotenic acid, which was performed in rats at postnatal day 7 resulting in alterations in the mesolimbic (MLi) and mesocortical (MC) neurotransmission in these animals following puberty. Treatment of these rats with antipsychotic drugs (APDs) resulted in normalization of these pathways.

The NVH-lesion rat has been previously shown to be a robust model for schizophrenia because NVH animals have displayed unique post-pubertal behavioural and neurochemical changes similar to those observed in schizophrenic patients. Behaviourally, these animals displayed: (i) hyperactivity in response to d-amphetamine and stress; (ii) deficit in social interaction; (iii) deficits in prepulse inhibition (PPI). Neurochemically, these animals showed: (i) loss of dendritic spine density and reductions in dendritic length; (ii) excessive firing of cortical pyramidal regions when MC regions were stimulated; (iii) reductions in brain-derived neurotrophic factor (BDNF) and nerve growth factor-1B (NGF-1B).

In this study, Western blotting or immunoblotting was used to measure CRP40 levels in nucleus accumbens tissue of sham-lesioned controls (n=8) versus NVH-lesioned (n=7) rats. It was determined that CRP40 levels were significantly reduced in the NVH-lesioned model when compared to the controls. These results indicate that CRP40 may have distinct and important functions which are altered in schizophrenia. Underexpression of CRP40 may be one of the factors involved in the pathogenesis of schizophrenia and treatment to restore defective CRP40 levels may provide an effective treatment for schizophrenia.

Materials and Methods

NVH-lesion surgery in animals was performed as previously described by Srivastava's group (1). Briefly, young male Sprague-Dawley rats were randomly divided into two groups: group one were the sham-lesioned controls (n=8) and group two were the NVH=lesioned rats (n=7). Surgery to induce neonatal hippocampus damage by ibotenic acid was performed on postnatal day 7. The sham-operated animals received the same amount of phosphate buffer saline instead of ibotenic acid during surgery. 7 days after the surgery, the rats were sacrificed and several brain regions were removed and immediately frozen in dry ice. The nucleus accumbens was used in experiments. Protein isolation from brain regions was performed by the TRIzol manufacturer's protocol. Protein concentration from each fraction was determined using Quick Start Bradford Protein Assay (Bio-Rad laboratories). Western blotting was performed on the protein portion of the nucleus accumbens brain region as per the following protocols: 10 µg of protein was loaded in duplicate from each sample onto a 10% sodium dodecyl sulphate-polyacrylamide (SDS-PAGE) gel (5.5 mL 1.5 M Tris (pH 8.8), 9 mL distilled water, 200 µL 10% ammonium persulfate (APS), and 15 µL Tetramethylethylenediamine (TEMED). To ensure that all samples entered the separating gel simultaneously, a 4% stacking gel was used (5 mL 0.5 M Tris (pH 6.8), 12.2 mL distilled water, 200 µL 10% SDS, 2.6 mL 30% acrylamide, 100 µL APS, and 20 µL TEMED). Gels were loaded onto a Bio-Rad mini-PROTEAN III rig (Bio-Rad, Mississauga, ON) containing 1× running buffer (10× running buffer of 15 g/L Tris, 72 g/L glycine, and 5 g/L SDS, diluted and distilled with water) and run at 60 V through stacking gel and 80 V through separating gel. Samples were prepared using 0.4% bromophenol blue. Gels were equilibrated in transfer buffer (12 mM Tris, 96 mM glycine, and 10% methanol for 20 minutes and transferred onto a 0.45 µm nitrocellulose membrane (PerkinElmer Life Sciences, Boston, Mass.) using the Bio-Rad Wet Transfer Unit (Bio-Rad). Successful transfer was verified using Ponceau S staining (1 g Ponceau S, 50 mL acetic acid, in 950 mL distilled water). Once transferred, the resulting blots were immersed in blocking solution (5% skim milk, 50 mM Tris, 150 mM NaCl, 0.2% Tween-20, pH 8.5) for 1 hour at room temperature and exposed to primary antibody for CRP40 (diluted as per supplier's suggestions) overnight at 4 degrees Celsius. Following primary antibody incubation, membranes were washed and exposed to secondary antibody anti-rabbit antibody. Visualization of the probed protein bands was achieved using enhanced chemiluminescence kit reagents as per manufacturer's instructions (Amersham Biosciences, Pittsburgh, Pa.). Membranes were exposed to Kodak Biomax XAR film (Perkin Elmer Life Sciences, Boston, Mass.) for 1, 2, 5, 10, 20, 30, 45, and 60 seconds. Exposed films were developed and protein bands were scanned onto a computer and optical densities (OD) bands were analyzed using the ImageJ program (NIH, Bethesda, Md.)

A two-tailed unpaired t-test with a confidence interval of 95% was utilized to analyze the data. Statistical analysis of the results was performed utilizing Graph Pad Prism 5.0 software.

Results

Figure 24:
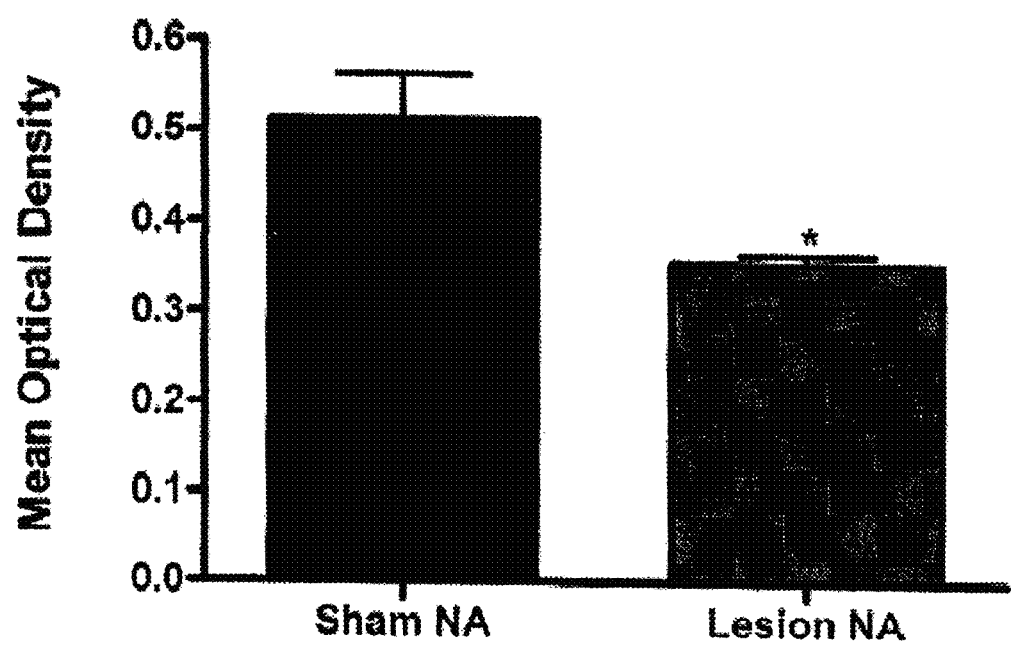
FIG. 24 shows the CRP40 protein concentration from nucleus accumbens tissues of sham-lesioned rats (n=8) versus Neonatal Ventral Hippocampus (NVH)-lesioned rats (n=7) determined by Western Blotting.
Figure 26:
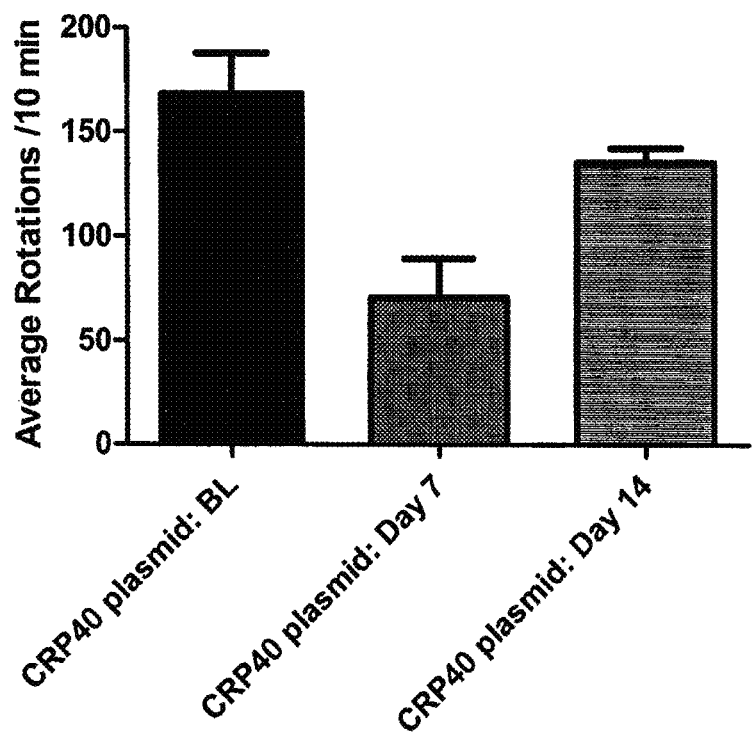
FIG. 26 shows the effect of CRP40 plasmid injection in the striatum on apomorphine-induced turning behaviour in 6-OHDA lesioned hemi-Parkinson's rat model.

FIG. 24 shows the CRP40 protein concentration from nucleus accumbens tissues of sham-lesioned rats (n=8) versus Neonatal Ventral Hippocampus (NVH)-lesioned rats (n=7) determined by Western Blotting. A two-tailed unpaired t-test with a confidence interval of 95% was utilized to analyze the data. Western blot results, measurement of OD, and statistical analysis indicated that CRP40 protein was significantly reduced in NVH-lesioned rats when compared to sham-lesioned controls (p=0.0125) (FIG. 26).

Conclusions

The purpose of this study was to investigate the role of CRP40 in schizophrenia utilizing the well-characterized NVH-lesioned animal model. CRP40 levels were measured in nucleus accumbens of NVH-lesioned rats versus sham-lesioned controls utilizing the technique of western blotting. The results indicated that there were statistically significant decreases in CRP40 levels in the NVH-lesioned model of schizophrenia when compared to the sham-lesioned controls. This study provides evidence for the involvement of CRP40, a novel heat-shock protein, in the pathophysiology of schizophrenia. It was hypothesize that CRP40 may be involved in dopaminergic neurotransmission and protection from oxidative stress which is impaired in schizophrenia. It is believed that restoration of CRP40 levels could provide effective treatment for schizophrenia and other hypo-dopaminergic neurological diseases, such as Parkinson's.

Example 12

Measurement of CRP40 Expression in Relation to Schizophrenia (Post-Mortem)

The objective of this study was to investigate the role of Catecholamine Regulated Protein 40 (CRP40) in human subjects who had schizophrenia. Post-mortem prefrontal cortex samples from patients with schizophrenia (n=16, age 53±22 years (mean±SD), post mortem interval (PMI) 26±22 h) and normal healthy controls (n=16, age 70±18 years, 8 males/8 females, PMI 16±4 h) were used. CRP40 protein expression was measured utilizing the technique of Western blotting or immunoblotting. It was determined that there was a statistically significant decrease in CRP40 protein levels in the schizophrenia post-mortem brains when compared to the brains of normal, healthy controls. The results indicate that CRP40 is implicated in schizophrenia and may be involved in the pathogenesis of schizophrenia and further support the hypothesis that restoration of the CRP40 deficit in the brain could provide a useful new treatment of schizophrenia.

Treatment Groups

Post-mortem prefrontal cortex samples from patients with schizophrenia (n=16, age 53±22 years (mean±SD), post mortem interval (PMI) 26±22 h) and normal healthy controls (n=16, age 70±18 years, 8 males/8 females, PMI 16±4 h) were obtained from the Human Brain and Spinal Fluid Resource Center (Los Angeles, Calif.). Post-mortem samples were organized according to class of anti-psychotic drug (APD) treatment. The classes of APD treatment were the following: typical APDs, atypical APDs and control (no APDs). Patients who received a combination of typical and atypical APDs were excluded from the study to avoid potential confounds of drug class interactions (n=3). As well, those patients whose antipsychotic drug history was not available were also excluded from the study (n=4).

Materials and Methods

Prefrontal cortex brain samples were homogenized in Tris-EDTA (50 Mm Tris, 1 mM EDTA, pH 7.4) with a protease inhibitor cocktail (Mini complete tablet EDTA-free, Roche Applied Science, Laval QC).

Protein isolation from brain regions was performed by the TRIzol manufacturer's protocol. Protein concentration from each fraction was determined using Quick Start Bradford Protein Assay (Bio-Rad laboratories). Protein expression was analyzed using western blotting techniques according to the following protocols: 10 µg of protein from each sample was loaded in duplicate onto a 10% sodium dodecyl sulphate-polyacrylamide (SDS-PAGE) gel (5.5 mL 1.5 M Tris (pH 8.8), 9 mL distilled water, 200 µL 10% ammonium persulfate (APS), and 15 µL Tetramethylethylenediamine (TEMED). To ensure that all samples entered the separating gel simultaneously, a 4% stacking gel was used (5 mL 0.5 M Tris (pH 6.8), 12.2 mL distilled water, 200 µL 10% SDS, 2.6 mL 30% acrylamide, 100 µL APS, and 20 µL TEMED). Gels were loaded onto a Bio-Rad mini-PROTEAN III rig (Bio-Rad, Mississauga, ON) containing 1× running buffer (10× running buffer of 15 g/L Tris, 72 g/L glycine, and 5 g/L SDS, diluted and distilled with water) and run at 60 V through stacking gel and 80 V through separating gel. Samples were prepared using 0.4% bromophenol blue. Gels were equilibrated in transfer buffer (12 mM Tris, 96 mM glycine, and 10% methanol for 20 minutes and transferred onto a 0.45 µm nitrocellulose membrane (PerkinElmer Life Sciences, Boston, Mass.) using the Bio-Rad Wet Transfer Unit (Bio-Rad). Successful transfer was verified using Ponceau S staining (1 g Ponceau S, 50 mL acetic acid, in 950 mL distilled water). Once transferred, the resulting blots were immersed in blocking solution (5% skim milk, 50 mM Tris, 150 mM NaCl, 0.2% Tween-20, pH 8.5) for 1 hour at room temperature and exposed to primary antibody for CRP40 (diluted as per supplier's suggestions) overnight at 4 degrees Celsius. Following primary antibody incubation, membranes were washed and exposed to secondary antibody, anti-rabbit antibody. Visualization of the probed protein bands was achieved using enhanced chemiluminescence kit reagents as per manufacturer's instructions (Amersham Biosciences, Pittsburgh, Pa.). Membranes were exposed to Kodak Biomax XAR film (PerkinElmer Life Sciences, Boston, Mass.) for 1, 2, 5, 10, 20, 30, 45, and 60 seconds. Exposed films were developed and protein bands were scanned onto a computer and analyzed using the ImageJ program (NIH, Bethesda, Md.).

A two-tailed unpaired t-test with a confidence interval of 95% was utilized to analyze the data. Statistical analysis of the results was performed utilizing Graph Pad Prism 5.0 software.

Results

Figure 25:
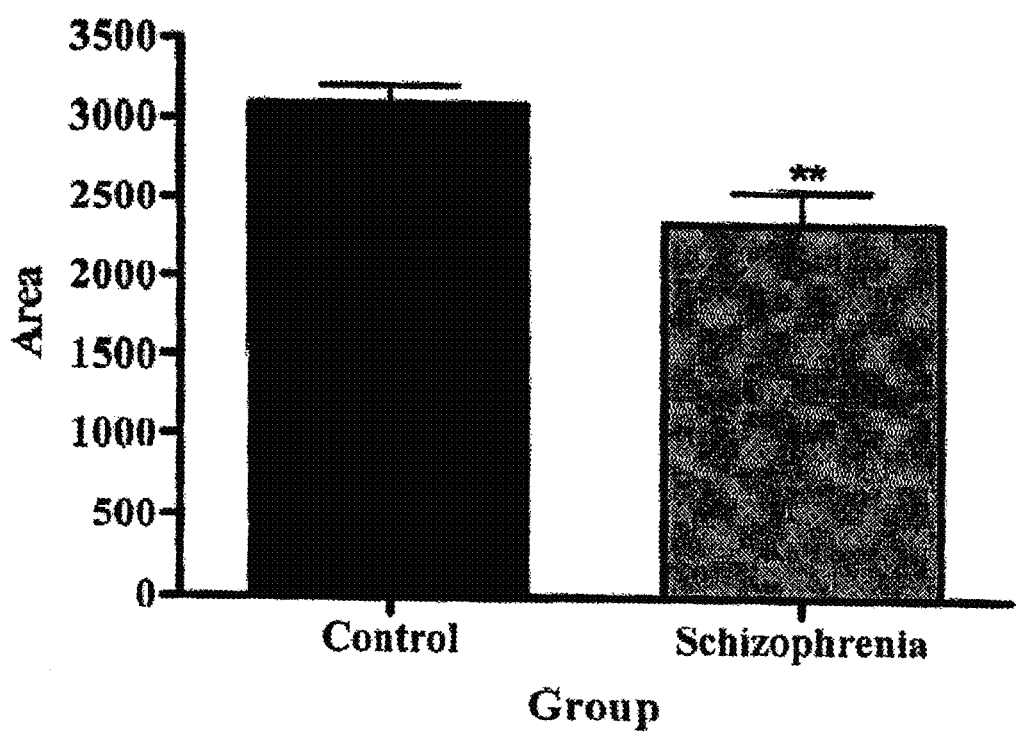
FIG. 25 shows CRP40 expression in post-mortem prefrontal cortex samples from patients with schizophrenia (n=16, age 53±22 years (mean±SD) post mortem interval (PMI) 26±22 h) versus normal healthy controls (n=16, age 70±18 years, 8 males/8 females, PMI 16±4 h), determined by Western Blotting.
Figure 27:
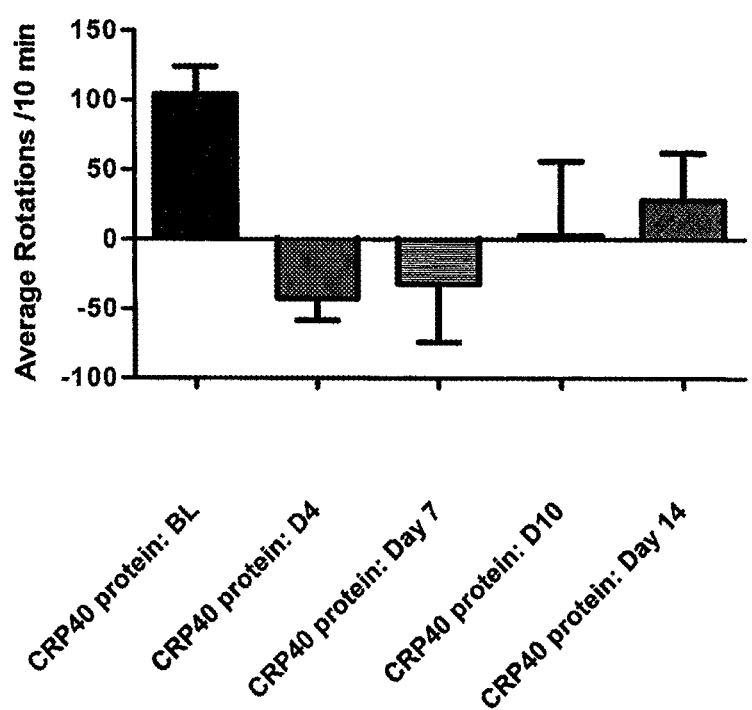
FIG. 27 shows the effect of CRP40 protein injection in the striatum on apomorphine-induced turning behaviour in 6-OHDA lesioned hemi-Parkinson's rat model.

FIG. 25 shows CRP40 expression in post-mortem prefrontal cortex samples from patients with schizophrenia (n=16, age 53±22 years (mean±SD) post mortem interval (PMI) 26±22 h) versus normal healthy controls (n=16, age 70±18 years, 8 males/8 females, PMI 16±4 h), determined by Western Blotting. A two-tailed unpaired t-test with a confidence interval of 95% was utilized to analyze the data. Western blot results and statistical analysis indicated that CRP40 protein was significantly reduced in schizophrenia subjects when compared to normal, healthy controls (p=0.0047) (FIG. 27). These results indicate that reduced expression of CRP40 may play an important role in schizophrenia.

Conclusions

The purpose of this study was to investigate the role of CRP40 in schizophrenia in humans. CRP40 levels were measured in prefrontal cortex of post-mortem brain samples of schizophrenia subjects versus healthy, normal controls. The results indicated that there were statistically significant decreases in CRP40 levels in the schizophrenia group when compared to controls. This study provides evidence that CRP40 may play an important role as a biomarker of schizophrenia and further supports that hypothesis that CRP40 is a useful treatment for schizophrenia.

Example 13

Measurement of CRP40 Expression-Parkinson's Disease Post-mortem Results

The objective of this study was to investigate the role of CRP40 in post mortem samples from human subjects who had Parkinson's disease (PD) to determine if CRP40 levels were altered in these brain samples. Post-mortem prefrontal cortex samples from patients who had Parkinson's disease (n=10) and normal healthy controls (n=10) were used. PD seems to impair cognitive prefrontal cortex functions. Striatum samples (PD group n=4, age range 53-70; normal control group n=5) and substantia nigra samples (PD group n=4, age range 53-70; normal control group n=5) were also obtained. Samples from the striatum were used to examine CRP40 levels because this area of the brain is responsible for balance and movement which are impaired in PD. The substantia nigra was also examined for CRP40 levels because this area is responsible for the production of dopamine and deteriorates in PD. CRP40 protein expression was measured in samples utilizing the technique of Western blotting or immunoblotting.

Treatment Groups

Post-mortem prefrontal cortex samples from patients with PD (n=10) and normal healthy controls (n=10), striatum samples (PD group n=4, age range 53-70; normal control group n=5), and substantia nigra samples (PD group n=4, age range 53-70; normal control group n=5) were obtained from the Human Brain and Spinal Fluid Resource Center, University of California Los Angeles (UCLA).

Materials and Methods

Prefrontal cortex brain samples, striatum samples, and substantia nigra samples as well as normal controls were homogenized in Tris-EDTA (50 Mm Tris, 1 mM EDTA, pH 7.4) with a protease inhibitor cocktail (Mini complete tablet EDTA-free, Roche Applied Science, Laval QC). Protein isolation from brain regions was performed by the TRIzol manufacturer's protocol. Protein concentration from each fraction was determined using Quick Start Bradford Protein Assay (Bio-Rad laboratories). Protein expression was analyzed using western blotting techniques according to the following protocols: 10 µg of protein from each sample was loaded in duplicate onto a 10% sodium dodecyl sulphate-polyacrylamide (SDS-PAGE) gel (5.5 mL 1.5 M Tris (pH 8.8), 9 mL distilled water, 200 µL 10% ammonium persulfate (APS), and 15 µL Tetramethylethylenediamine (TEMED). To ensure that all samples entered the separating gel simultaneously, a 4% stacking gel was used (5 mL 0.5 M Tris (pH 6.8), 12.2 mL distilled water, 200 µL 10% SDS, 2.6 mL 30% acrylamide, 100 µL APS, and 20 µL TEMED). Gels were loaded onto a Bio-Rad mini-PROTEAN III rig (Bio-Rad, Mississauga, ON) containing 1× running buffer (10× running buffer of 15 g/L Tris, 72 g/L glycine, and 5 g/L SDS, diluted and distilled with water) and run at 60 V through stacking gel and 80 V through separating gel. Samples were prepared using 0.4% bromophenol blue. Gels were equilibrated in transfer buffer (12 mM Tris, 96 mM glycine, and 10% methanol for 20 minutes and transferred onto a 0.45 µm nitrocellulose membrane (PerkinElmer Life Sciences, Boston, Mass.) using the Bio-Rad Wet Transfer Unit (Bio-Rad). Successful transfer was verified using Ponceau S staining (1 g Ponceau S, 50 mL acetic acid, in 950 mL distilled water). Once transferred, the resulting blots were immersed in blocking solution (5% skim milk, 50 mM Tris, 150 mM NaCl, 0.2% Tween-20, pH 8.5) for 1 hour at room temperature and exposed to primary antibody for CRP40 (e.g. anti-CRP40 antibody) diluted as per supplier's suggestions and left overnight at 4 degrees Celsius. Following primary antibody incubation, membranes were washed and exposed to secondary antibody (e.g. anti-rabbit antibody). Visualization of the probed protein bands was achieved using enhanced chemiluminescence kit reagents as per manufacturer's instructions (Amersham Biosciences, Pittsburgh, Pa.). Membranes were exposed to Kodak Biomax XAR film (PerkinElmer Life Sciences, Boston, Mass.) for 1, 2, 5, 10, 20, 30, 45, and 60 seconds. Exposed films were developed and protein bands were scanned onto a computer and optical densities (OD) bands were determined using the ImageJ program (NIH, Bethesda, Md.).

A two-tailed unpaired t-test with a confidence interval of 95% was utilized to analyze the data. Statistical analysis of the results was performed utilizing Graph Pad Prism 5.0 software.

Results

Western blot results, measurement of OD, and statistical analysis indicated that CRP40 protein levels were decreased in PD post-mortem brains in all samples (e.g. prefrontal cortex, striatum, and substantia nigra) when compared to the brains of healthy controls. Although the results did not reach statistical significance, previous studies from the inventor's laboratory have provided evidence for CRP40 involvement in PD. These studies have shown that CRP40 is capable of coupling to dopamine (DA), a catecholamine which is dysregulated in PD, as well as co-localizing with tyrosine hydroxylase (TH), a rate limiting enzyme in DA biosynthesis. A larger sample size of PD post-mortem brains is likely needed to achieve statistical significance in post mortem brain samples.

Example 14

Treatment Study Using CRP40 in an Animal Model of Parkinson's Disease

This research study examined the potential of CRP40 as a therapeutic in Parkinson's disease (PD). It has been shown herein that dopamine (DA) can modulate CRP40 expression. Further, knockdown of CRP40 in the medial prefrontal cortex (mPFC) caused deficits in DA-dependant behaviours related to human disease. This study investigated whether the introduction of CRP40 into the lesioned region of a rat model of PD would reduce or reverse symptoms associated with PD compared to control animals. This model is a well-established one in which the nigrostriatal system is hemi-laterally lesioned by injection of the cytotoxin 6-hydroxydopamine (6-OHDA). These animals show phenotypic rotating behaviour as a result of the hemi-lesion. The goal of this study was to establish whether lesioned animals would exhibit reduced rotation after treatment with CRP40 protein or plasmid.

Treatment Groups

The treatment groups were the following: Group 1 (n=3; males) were hemi-lesioned animals treated with a sham injection (CSF) to the Striatum; Group 2 (n=3; males) were hemi-lesioned animals treated with Mortalin2 plasmid injection to the Striatum; Group 3 (n=3; males) were hemi-lesioned animals treated with CRP40 plasmid injection to the Striatum; Group 4 (n=2; males) were hemi-lesioned animals treated with Mortalin2 protein injection to the Striatum; Group 5 (n=2; males) were hemi-lesioned animals treated with CRP40 protein injection to the Striatum; Group 6 (n=3; males) were controls, non-lesioned, and received a CSF injection to the Striatum.

Materials and Methods

Once the animals were comfortable with the experimenter, they were subjected to a series of behavioural tests for baseline measures. In addition to the apomorphine-induced rotation, other tests included prepulse inhibition (PPI) and locomotor activity tests. The apomorphine-induced rotations test involves giving each animal a subcutaneous injection of apomorphine according to body weight. Since the animals are lesioned hemi-laterally at the nigrostriatal pathway, they show compulsive turning behaviour in a direction contralateral to the lesion. For this project, there was interest in the number of rotations each animal made in a ten minute testing period. PPI is a test of sensorimotor gating where animals are exposed to a startling acoustic pulse. This pulse, however, follows a subtle pre-pulse which allows for inhibition of the startle response. Locomotor activity test involves cubic chambers lined with infrared sensors that detect any and all movements made by the animal over a three hour testing period. For this experiment "total distance travelled" measurements were of interest.

Once all baseline data was collected, the rats were placed under gaseous anaesthesia and injected, via cannulae, with one of the five following treatments: CSF sham (Striatal n=3), CRP40 plasmid DNA (Striatal n=3), MOT-2 plasmid DNA (Striatal n=3), CRP40 protein (Striatal n=2), MOT-2 protein (Striatal n=2).

After recovery from surgery, all animals were again tested using the same behavioural methods for post-intervention measures. PPI and locomotor activity were tested at 7 and 14 days post-injection, and apomorphine-induced rotation was tested at various time points between days 2 and 14 post-injection. On day 15 post-injection, all rats were sacrificed. Fresh brain tissue was sliced using razor blades and a brain mould, then micro-punched for specific brain area samples, and flash frozen on dry ice.

Results

FIG. 26 shows the effect of CRP40 plasmid injection in the striatum on apomorphine-induced turning behaviour in 6-OHDA lesioned hemi-Parkinson's model. Injection of CRP40 plasmid into the striatum on the lesioned side of PD rats showed a reduction of rotational symptoms at day 7 post-injection. The rotational symptoms were increasing again by day 14.

FIG. 27 shows the effect of CRP40 protein injection in the striatum on apomorphine-induced turning behaviour in 6-OHDA lesioned hemi-Parkinson's model. Injection of CRP40 protein into the striatum on the lesioned side of PD rats showed a reversal of rotational symptoms at days 4 and 7 post-injection, likely indicating a need for titration of the dose. By day 10, rotational symptoms were alleviated. The behavioural correction was astonishing. The rotational symptoms were beginning to increase again by day 14.

MOT-2 injection showed the same trend as CRP40, but these results were not significant. No other groups showed significant differences on this behavioural test. No groups showed significant differences on either of the PPI or locomotor behavioural tests at baseline or post-treatment, however larger n's would likely be required to achieve significance. HPLC revealed significant increase in the levels of DA in the SN & striatum of the striatal-injected rats.

CONCLUSIONS

This study examined the effect of CRP40 protein and plasmid injection on the behavioural phenotypes seen in the 6-OHDA model of PD in rats in order to explore the use of CRP40 as a therapeutic for PD. Based on this study, it was determined that injection of CRP40 plasmid into the striatum partially alleviated the apomorphine-induced rotational symptoms. Further, injection of CRP40 protein into the striatum completely reversed these symptoms. It was found that CRP40 caused an increase in dopamine concentration at both the SN and the striatum when injected into the striatum. The results indicate that CRP40 has good potential for therapeutic applications in PD patients. Delivery systems can be optimized for human applications.

The foregoing description and examples describe embodiments of the disclosure. As will be appreciated by one of skill in the art, other embodiments of the disclosure exist which are encompassed by the appended claims.

All references referred to herein are incorporated by reference.

REFERENCE LIST

Benes, F. M., 2000. Emerging principles of altered neural circuitry in schizophrenia. Brain Res Brain Res Rev. 31, 251-269

Ben Zvi, A. P. and Goloubinoff, P., 2001. Review: mechanisms of disaggregation and refolding of stable protein aggregates by molecular chaperones. J Struct Biol. 135, 84-93.

Bradford, M. M., 1976. A rapid and sensitive method for the quantitation of microgram quantities of protein utilizing the principle of protein-dye binding. Anal Biochem. 72, 248-254.

Crowe, R. R. and Vieland, V., 1999. Report of the Chromosome 5 Workshop of the Sixth World Congress on Psychiatric Genetics. Am J Med. Genet. 88, 229-232.

Gabriele, J., Culver, K., Sharma, S., Zhang, B., Szechtman, H., and Mishra, R., 2003. Asymmetric modulation of a catecholamine-regulated protein in the rat brain, following quinpirole administration. Synapse. 49, 261-269.

Gabriele J., Rajaram, M., Zhang, B., Sharma, S., and Mishra, R. K., 2002. Modulation of a 40-kDa catecholamine-regulated protein following D-amphetamine treatment in discrete brain regions. Eur J. Pharmacol. 453, 13.

Gabriele J., Culver K, Zhang B, Szechtman H, and Mishra R. K. Asymmetric modulation of a catecholamine regulated protein in rat brain following quinpirole treatment. Synapse (accepted with revisions). 2003.
Ref Type: Unpublished Work Gabriele, J. P., Chong, V. Z., Pontoriero, G. F., and Mishra, R. K., 2005. Decreased expression of a 40-kDa catecholamine-regulated protein in the ventral striatum of schizophrenic brain specimens from the Stanley Foundation Neuropathology Consortium. Schizophr Res. 74, 111-119.

Giffard, R. G., Xu, L., Zhao, H., Canico, W., Ouyang, Y., Qiao, Y., Sapolsky, R., Steinberg, G., Hu, B., and Yenari, M. A., 2004. Chaperones, protein aggregation, and brain protection from hypoxic/ischemic injury. J Exp Biol. 207, 3213-3220.

Goto, A., Doering, L., Nair, V. D., and Mishra, R. K., 2001. Immunohistochemical localization of a 40-kDa catecholamine regulated protein in the nigrostriatal pathway. Brain Res. 900, 314-319.

Graveley, B. R., 2001. Alternative splicing: increasing diversity in the proteomic world. Trends Genet. 17, 100-107.

Grover, A., 2002. Molecular biology of stress responses. Cell Stress Chaperones. 7, 1-5.

Hong, K. S., McInne SjL. A., Service, S. K., Song, T., Lucas, J., Silva, S., Foiirnier, E., Leon, P., Molina, J., Reus, V. L, Sandkuijl, L. A., and Freimer, N. B., 2004. Genetic mapping using haplotype and model-free linkage analysis supports previous evidence for a locus predisposing to severe bipolar disorder at 5q31-33. Am J Med Genet B Neuropsychiatr Genet. 125, 83-86.

Kaul, S. C, Taira, K., Pereira-Smith, O. M., and Wadhwa, R., 2002. Mortalin: present and prospective. Exp Gerontol. 37, 1157-1164.

Kaul, S. C, Yaguchi, T., Taira, K., Reddel, R. R., and Wadhwa, R., 2003. Overexpressed mortalin (mot-2)/mthsp70/GRP75 and hTERT cooperate to extend the in vitro lifespan of human fibroblasts. Exp Cell Res. 286, 96-101.

Knable, M. B., 1999. Schizophrenia and bipolar disorder: findings from studies of the Stanley Foundation Brain Collection. Schizophr Res. 39, 149-152.

Knable, M. B., Torrey, E. F., Webster, M. J., and Bartko, J. J., 2001. Multivariate analysis of prefrontal cortical data from the Stanley Foundation Neuropathology Consortium. Brain Res Bull. 55, 651-659.

Lewis, C. M., Levinson, D. F., Wise, L. H., DeLisi, L. E., Straub, R. E., Hovatta, L, Williams, N. M., Schwab, S. G., Pulver, A. E., Faraone, S. V., Brzustowicz, L. M., Kaufmann, C. A., Garver, D. L., Gurling, H. M., Lindholm, E., Coon, H., Moises, H. W., Byerley, W., Shaw, S. H., Mesen, A., Sherrington, R., O'Neill, F. A., Walsh, D., Kendler, K. S., Ekelund, J., Paunio, T., Lonnqvist, J., Peltonen, L., O'Donovan, M. C, Owen, M. J., Wildenauer, D. B., Maier, W., Nestadt, G., Blouin, J. L., Antonarakis, S. E., Mowry, B. J., Silverman, J. M., Crowe, R. R., Cloninger, C. R., Tsuang, M. T., Malaspina, D., Harkavy-Friedman J. M., Svrakic, D. M., Bassett, A. S., Holcomb, J., Kalsi, G., McQuillin, A., Brynjolfson, J., Sigmundsson, T., Petursson, H., Jazin, E., Zoega, T., and Helgason, T., 2003. Genome scan meta-analysis of schizophrenia and bipolar disorder, part II: Schizophrenia. Am J Hum Genet. 73, 34-48.

MacariOj A J. and Conway, d. M., 2002. Sick chaperones and ageing: a perspective. Ageing Res Rev. 1, 295-311.

Matsumoto, M., Weickert, C. S., Beltaifa, S., Kolachana, B., Chen, J., Hyde, T. M., Herman, M. M., Weinberger, D. R., and Kleinman, J. E., 2003. Catechol O-methyltransferase (COMT) mRNA expression in the dorsolateral prefrontal cortex of patients with schizophrenia. Neuropsychopharmacology. 28, 1521-1530.

Modi, P. I., Kashyap, A., Nair, V. D., Ross, G. M., Fu, M., Savelli J. E., Marcotte, E. R., Barlas, C, and Mishra, R. K., 1996. Modulation of brain catecholamine absorbing proteins by dopaminergic agents. Eur J. Pharmacol. 299, 213-220.

Modrek, B. and Lee, C. J., 2003. Alternative splicing in the human, mouse and rat genomes is associated with an increased frequency of exon creation and/or loss. Nat. Genet. 34, 177-180.

Muchowski, P. J. and Wacker J. L., 2005. Modulation of neurodegeneration by molecular chaperones. Nat Rev Neurosci. 6, 11-22.

Nair, V. D. and Mishra, R. K., 2001. Molecular cloning, localization and characterization of a 40-kDa catecholamine-regulated protein. J. Neurochem. 76, 1142-1152.

Ohtsuka, K. and Suzuki, T., 2000. Roles of molecular chaperones in the nervous system. Brain Res Bull. 53, 141-146.

Perlman, W. R., Weickert, C. S., Akil, M., and Kleinman, J. E., 2004. Postmortem investigations of the pathophysiology of schizophrenia: the role of susceptibility genes. J Psychiatry Neurosci. 29, 287-293.

Pira, L., Mongeau, R., and Pani, L., 2004. The atypical antipsychotic quetiapine increases both noradrenaline and dopamine release in the rat prefrontal cortex. Eur J. Pharmacol. 504, 61-64.

Ross, G. M., McCarry, B. E., and Mishra, R. K., 1995. Covalent affinity labeling of brain catecholamine-absorbing proteins using a high-specific-activity substituted tetrahydronaphthalene. J. Neurochem. 65, 2783-2789.

Ross, G. M., McCarry, B. E., Thakur, S., and Mishra, R. K., 1993. Identification of novel catecholamine absorbing proteins in the central nervous system. J Mol. Neurosci. 4, 141-148.

Seamans, J. K. and Yang, C. R., 2004. The principal features and mechanisms of dopamine modulation in the prefrontal cortex. Prog Neurobiol. 74, 1-58.

Seeman, P. and Kapur, S., 2000. Schizophrenia: more dopamine, more D2 receptors. Proc Natl Acad Sci USA. 97, 7673-7675.

Selemon, L. D. and Rajkowska, G., 2003. Cellular pathology in the dorsolateral prefrontal cortex distinguishes schizophrenia from bipolar disorder. Curr Mol. Med. 3, 427-436.

Sharan, N., Chong, V. Z., Nair, V. D., Mishra, R. K., Hayes, R. J., and Gardner, E. L., 2003.

Cocaine treatment increases expression of a 40 kDa catecholamine-regulated protein in discrete brain regions. Synapse. 47, 33-44.

Sharan, N., Nair, V. D., and Mishra, R. K., 2001. Modulation of a 40-kDa catecholamine regulated protein by dopamine receptor antagonists. Eur J. Pharmacol. 413, 73-79.

Sherman, M. Y. and Goldberg, A. L., 2001. Cellular defenses against unfolded proteins: a cell biologist thinks about neurodegenerative diseases. Neuron. 29, 15-32.

Sklar, P., Pato, M. T., Kirby, A., Petryshen, T. L., Medeiros, H., Carvalho, C, Macedo, A., Dourado, A., Coelho, I., Valente, J., Soares, M. J., Ferreira, C. P., Lei, M., Verner, A., Hudson, T. J., Morley, C. P., Kennedy, J. L., Azevedo, M. H., Lander, E., Daly, M. J., and Pato, C. N., 2004. Genome-wide scan in Portuguese Island families identifies 5q31-5q35 as a susceptibility locus for schizophrenia and psychosis. Mol. Psychiatry. 9, 213-218.

Stip, E., Tranulis, C, Legare, N., and Poulin, M J., 2003. [Antipsychotic drugs. Risk factors for diabetes]. Presse Med. 32, 1612-1617.

Soti, C. and Csermely, P., 2002a. Chaperones and aging: role in neurodegeneration and in other civilizational diseases. Neurochem Int. 41, 383-389.

Soti, C. and Csermely, P., 2002b. Chaperones come of age. Cell Stress Chaperones. 7, 186-190.

Svensson, T. H., 2003. Alpha-adrenoceptor modulation hypothesis of antipsychotic atypicality. Prog Neuropsychopharmacol Biol Psychiatry. 27, 1145-1158.

Wadhwa, R., Kaul, S. C, Ikawa, Y., and Sugimoto, Y., 1991. Protein markers for cellular mortality and immortality. Mutat Res. 256, 243-254.

Wadhwa, R., Taira, K., and Kaul, S. C, 2002. An Hsp70 family chaperone, mortalin/mthsp70/PBP74/Grp75: what, when, and where? Cell Stress Chaperones. 7, 309-316.

Weinberger, D. R., 1988. Schizophrenia and the frontal lobe. Trends Neurosci. 11, 367-370.

Weinberger, D. R., Egan, M. F., Bertolino, A., Callicott, J. H., Mattay, V. S., Lipska, B. K., Berman, K. F., and Goldberg, T. E., 2001. Prefrontal neurons and the genetics of schizophrenia. Biol Psychiatry. 50, 825-844.

Xie, H., Hu, Z., Chyna, B., Horrigan, S. K., and Westbrook, C. A., 2000. Human mortalin (HSPA9): a candidate for the myeloid leukemia tumor suppressor gene on 5q31. Leukemia. 14, 2128-2134.

Linninger et al. Drug Delivery into the Human Brain.

Bobo R. H., Laske D. W., Akbasak A., Morrison P. F., Dedrick R. L., Oldfield E. H., Convection-enchanced delivery of macromolecules in the brain, Proc. Natl. Acad. Sci. USA, 91(3), 2076-2080, 1991.

Pardridge, W. M., Non-invasive drug delivery to the human brain using endogenous blood-brain barrier transport systems, Research Focus, 2, 2, 49-59, 1999.

Pardridge, W. M., Drug and Gene Delivery to the Brain, The Vascular Route. Neuron, 36, 555-558, 2002.

Kalyanasundaram, S., Calhoun, D. V., Leong, W. K, A finite element model for predicting the distribution of drugs delivered intracranially to the brain, American Physiological Society, R1810-R1821, 1997.

Materialise, Inc., (Mimics), (accessed May 30, 2005) http://www.materialise.be/mimics/main_ENG.html.

Morrison, P. F., Laske, D. W., Bobo, H., Oldfield, E. H., Dedrick, L. R., High-flow microinfusion: tissue penetration and pharmacodynamics, American Journal of Physiology, 266, R292-R305, 1994.

Reisfeld, B., Kalyanasundaram, S., Leong, K., A mathematical model of polymeric controlled drug release and transport in the brain, Journal of Controlled Release, 36, 199-207, 1995.

Sarntinoranont M., Iadarola M. J., Lonser R. R. and Morrison P. F., Direct interstitial infusion of NK1-targeted neurotoxin into the spinal cord: a computational model, Am J Physiol Regul Integr Comp Physiol, 285, R243-R254, 2003.

Wang, C. H., Lee, T., Tan, Wang, F., Tan, W H. K., Simulation of Intratumoral Release of Etanidazole, Effects of the Size of Surgical Opening, Journal of Pharmaceutical Sciences, 92, 4, 773-789, 2003.

---

What is claimed is:

1. A method of treating Parkinson's disease in a patient in need thereof, comprising administering to the patient a therapeutically effective amount of human catecholamine regulated protein (CRP40) comprising the amino acid sequence as defined in SEQ ID NO: 8, or a functionally equivalent variant thereof exhibiting at least about 98% sequence homology with the amino acid sequence of SEQ ID NO: 8, wherein administering comprises direct injection of the CRP40 protein to the striatum area of the brain.

2. The method of claim 1, wherein the step of administering comprises administering to the patient a therapeutically effective amount of CRP40 protein comprising an amino acid sequence as set out in SEQ ID NO:8 or a functionally equivalent variant thereof having at least 99% sequence homology with the amino acid sequence of SEQ ID NO: 8.

3. The method of claim 2, wherein the step of administering comprises administering to the patient a therapeutically effective amount of CRP40 protein comprising an amino acid sequence as set out in SEQ ID NO:8.

4. The method of claim 1, wherein the patient is human.

* * * * *